(12) United States Patent
Schmitz

(10) Patent No.: US 12,127,737 B1
(45) Date of Patent: Oct. 29, 2024

(54) SYSTEM AND METHOD FOR OPERATING A HIGHLY MANEUVERABLE SURGICAL CATHETER AND BRONCHOSCOPE

(71) Applicant: Gregory P. Schmitz, Los Gatos, CA (US)

(72) Inventor: Gregory P. Schmitz, Los Gatos, CA (US)

(73) Assignee: Syncrobotix, Inc., Los Gatos, CA (US)

( * ) Notice: Subject to any disclaimer, the term of this patent is extended or adjusted under 35 U.S.C. 154(b) by 0 days.

(21) Appl. No.: 18/422,454

(22) Filed: Jan. 25, 2024

Related U.S. Application Data

(63) Continuation-in-part of application No. 18/324,493, filed on May 26, 2023, now Pat. No. 11,950,765.

(60) Provisional application No. 63/618,832, filed on Jan. 8, 2024, provisional application No. 63/603,757, filed on Nov. 29, 2023, provisional application No. 63/499,218, filed on Apr. 29, 2023.

(51) Int. Cl.
| | |
|---|---|
| *A61B 1/00* | (2006.01) |
| *A61B 17/00* | (2006.01) |
| *A61B 34/30* | (2016.01) |
| *A61M 25/01* | (2006.01) |

(52) U.S. Cl.
CPC ........ *A61B 17/00234* (2013.01); *A61B 34/30* (2016.02); *A61B 2017/00292* (2013.01); *A61B 2017/00398* (2013.01); *A61B 2034/301* (2016.02); *A61B 2034/303* (2016.02); *A61M 25/0113* (2013.01)

(58) Field of Classification Search
CPC . A61B 1/0057; A61B 1/0011; A61B 1/00149; A61B 1/0055; A61B 1/0125; A61B 1/018; A61B 1/05; A61B 1/2676; A61B 1/00147; A61B 1/00156; A61B 1/005; A61B 2090/3966; A61M 25/0138
USPC .......................................................... 600/102
See application file for complete search history.

(56) References Cited

U.S. PATENT DOCUMENTS

| | | | |
|---|---|---|---|
| 11,033,342 | B2 | 6/2021 | Schmitz |
| 2021/0100627 | A1 | 4/2021 | Soper et al. |
| 2021/0137620 | A1 | 5/2021 | Wallace et al. |
| 2022/0087755 | A1 | 3/2022 | Romo et al. |
| 2022/0304550 | A1 | 9/2022 | Romo et al. |
| 2022/0313375 | A1 | 10/2022 | Zhang et al. |

*Primary Examiner* — Timothy J Neal
*Assistant Examiner* — James Edward Boice
(74) *Attorney, Agent, or Firm* — Stephen E. Zweig

(57) ABSTRACT

System and method for using processor-controlled actuators to drive multi-stage catheter devices configured to navigate through complex narrow tissue openings such as lung bronchi pathway openings. The device comprises a proximal catheter portion containing a hollow torque shaft, with a distal catheter portion connected to the proximal portion by a rotatable coupler connected to this hollow shaft. The distal position of the proximal catheter can be controlled by independently controlled proximal stage steering cables positioned outside of the shaft, and the shaft itself can be used to rotate the distal catheter about the rotatable coupler. The position of the distal end of the distal catheter can be further controlled by distal stage steering cables positioned inside of the hollow shaft. The device is tipped by a tool plate, which can be equipped with various sensors and other instruments, connected to the outside via other conduits.

20 Claims, 55 Drawing Sheets

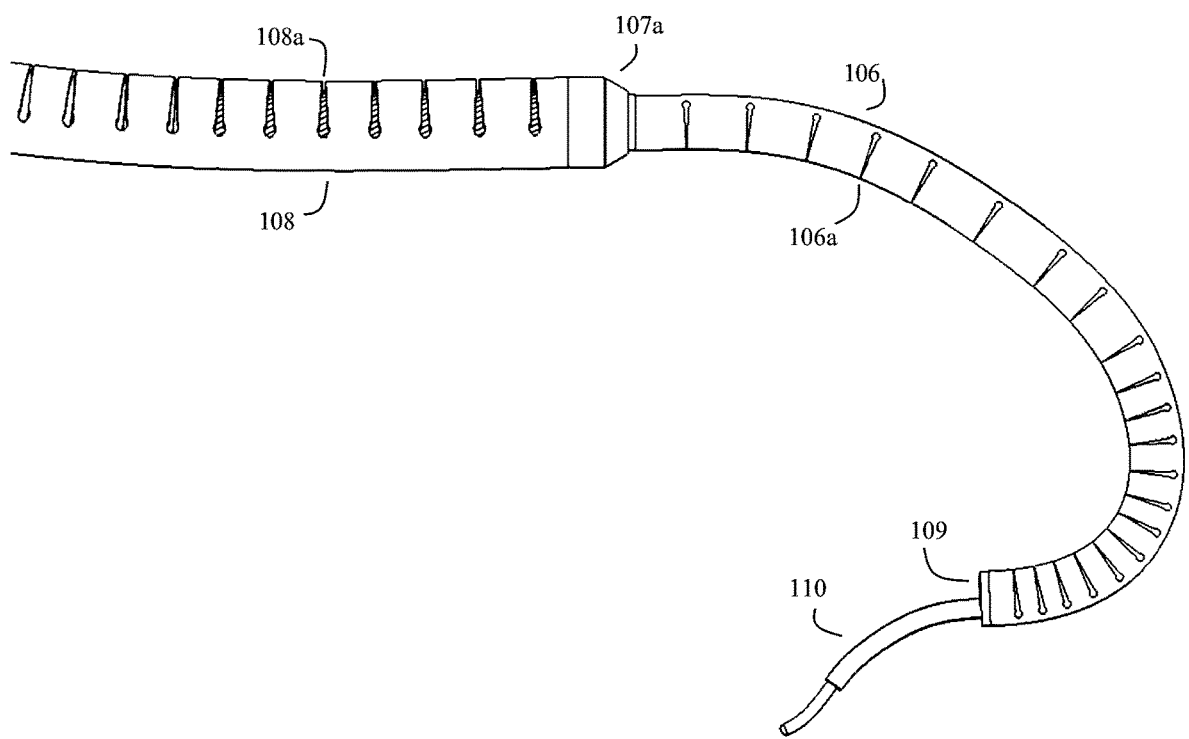

Fig. 12A
Fig. 12B
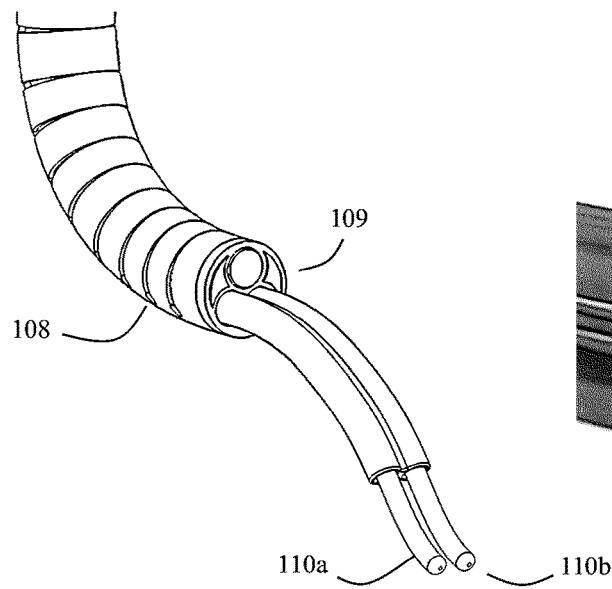
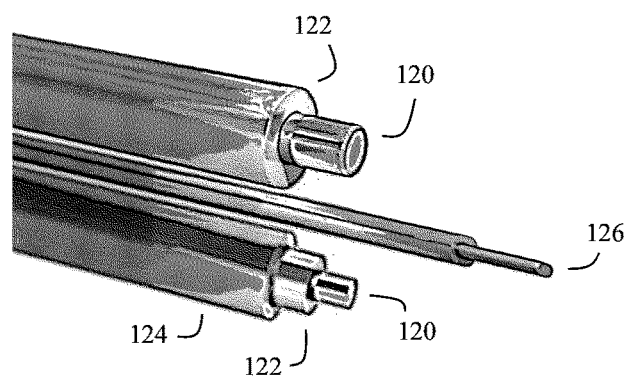

Fig. 38A
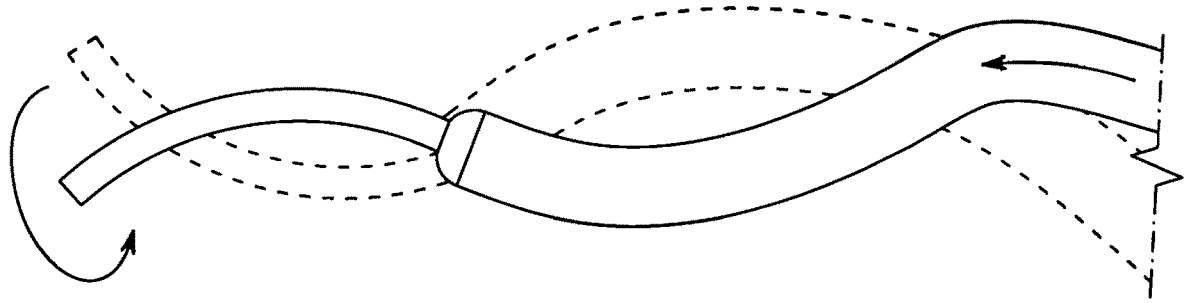
Fig. 38B
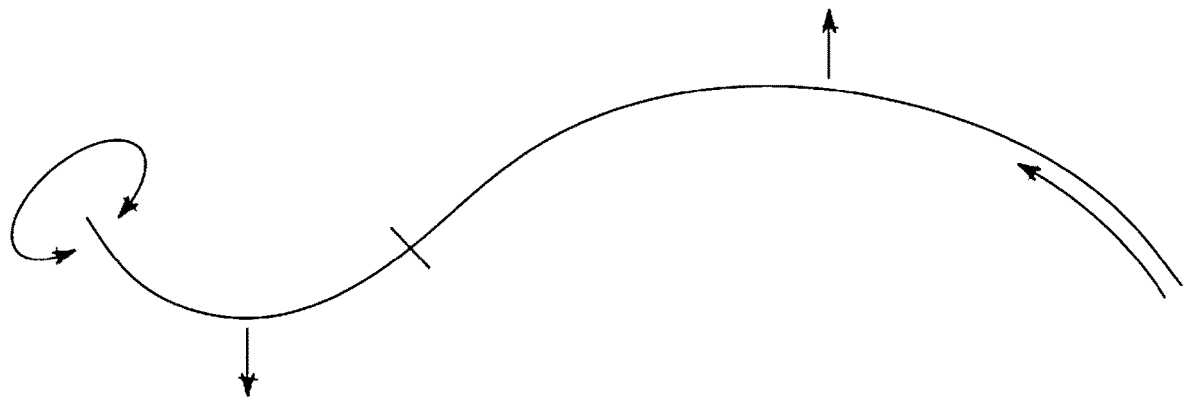
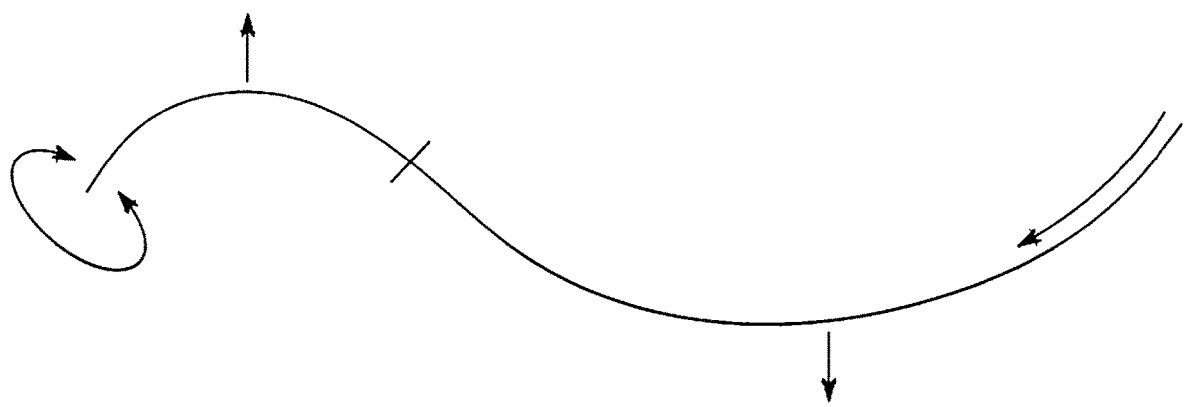

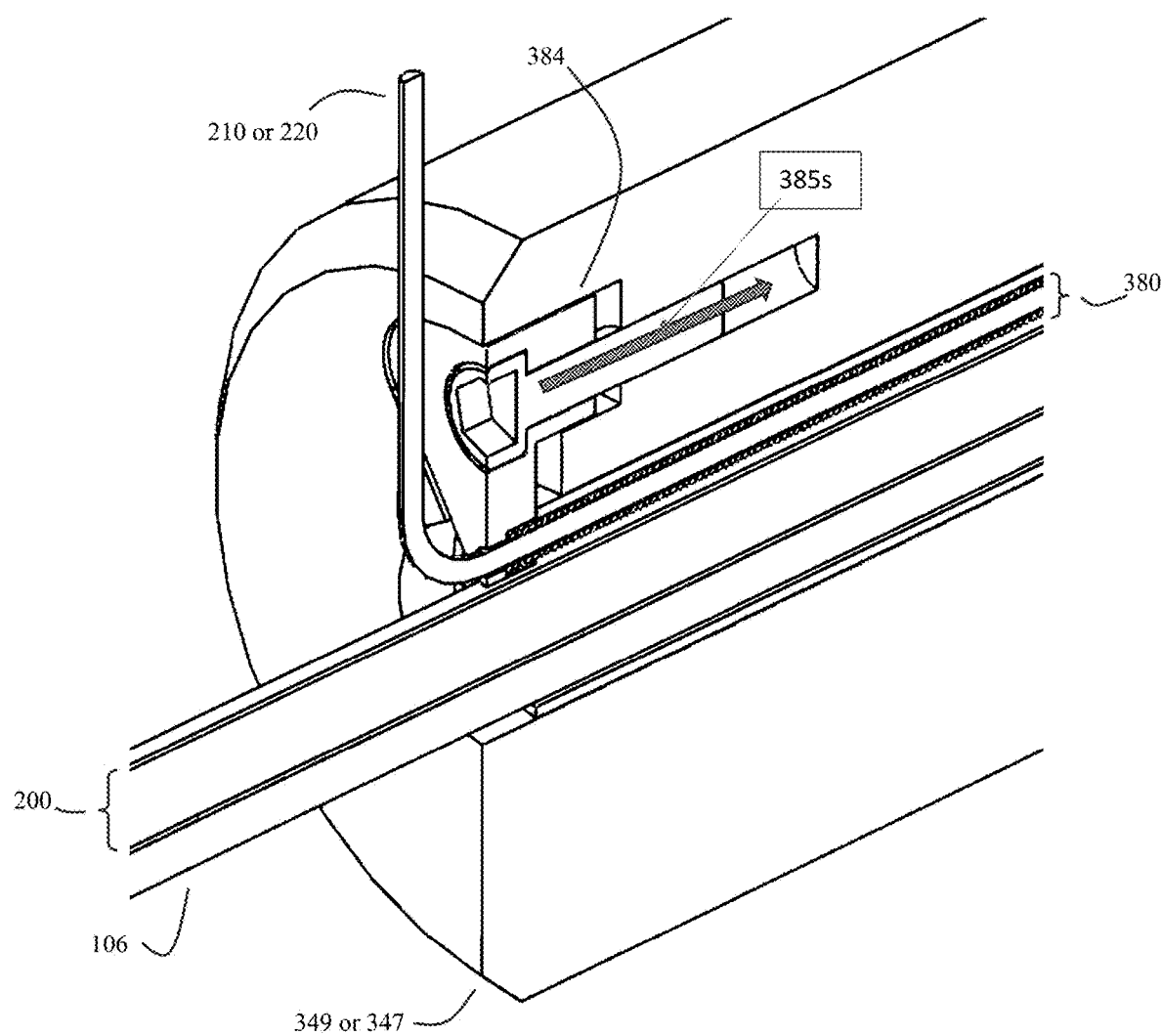

SYSTEM AND METHOD FOR OPERATING A HIGHLY MANEUVERABLE SURGICAL CATHETER AND BRONCHOSCOPE

CROSS-REFERENCE TO RELATED APPLICATIONS

This application is a continuation in part of U.S. patent application Ser. No. 18/324,493, filed May 26, 2023; this application also claims the priority benefit of U.S. provisional application 63/603,757 filed Nov. 29, 2023, and U.S. provisional application 63/618,832, filed Jan. 8, 2024; application Ser. No. 18/324,493 claimed the priority benefit of U.S. provisional application 63/499,218, filed Apr. 29, 2023. The entire contents of these applications are incorporated herein by reference.

BACKGROUND OF THE INVENTION

Field of the Invention

This invention is in the field of robotic surgery, as well as robotic systems and methods for operating surgical catheters and bronchoscopes.

Description of the Related Art

Medical and surgical catheters, and more specialized versions of such catheters such as bronchoscopes, are medical devices that are commonly used for purposes of medical diagnosis and treatment. Such "snake like" devices are designed to traverse various body lumens, such as arteries, veins, portions of the urinary, gastrointestinal, and reproductive systems, as well as various portions of the respiratory system and lungs. These devices are frequently used for other surgical applications as well.

Some of these medical devices are formed from long continuous tubes, often formed from medical grade polymers. Other such devices may comprise articulated sections formed from a plurality of smaller components that are often linked together by flexible joints. Such articulated devices themselves may often then be covered with an optional flexible medical plastic grade polymer as well.

Some of these medical devices are intended for direct manipulation by the surgeon or other healthcare professional. Other such devices may also have various motorized, processor controlled, and even robotically driven accessories. These are often used for greater precision and control.

Examples of such devices include various US patents and patent applications, such as Wallace, US 20210137620 A1; Romo, US 20220087755 A1 and US 20220304550 A1; Zhang US US20220313375A1; Souper US 20210100627 A1; and Schmitz, U.S. Ser. No. 11/033,342 B2.

Other prior art techniques include electroporation. Electroporation is an energy modality of pulsed electric fields in micro and nanosecond domain that if delivered through a micro-bronchoscope, could be used to deliver genes for immune response, initiate necrosis or initiate an immunogenic response.

Despite these advances, further advances in this art would be desirable.

BRIEF SUMMARY OF THE INVENTION

Although the systems and methods disclosed herein can be used for many different medical purposes, the present invention was inspired, in part, by a consideration of difficult-to-treat lung diseases, and the inadequacies of prior art manual and robotic bronchoscopes.

Thus, this disclosure will discuss both the structure of the lungs, and the utility of these improved methods for lung disease, in some detail. Note however, that this extensive discussion of lung structure and improved bronchoscopes is not intended to be limiting. The improved medical devices disclosed herein may be given different names, and may be used for a wide variety of medical and veterinary diagnostic and surgical purposes.

About the structure of the lung, and the limitations of prior art bronchoscopes

The bronchus of the lungs can be viewed as following a natural Fibonacci pattern of a typical tree where the branches divide and reduce in size as they get further out for the main trunk or, in this case, the Trachea. FIG. 1, which shows the lung bronchus system, illustrated shows the size reduction of the bronchial tree as the air moves from the larynx (10), down the Trachea (12), and divides into the Primary Bronchus (14), the Secondary Bronchus (16), the Tertiary Bronchus (18), and lastly the many Bronchiole (20).

The diameter of the bronchus pathways reduces in diameter as the branches move outward and downward away from the Trachea. For example, going from Subsegmental (Tertiary) to Terminal Bronchi (before the Bronchiole), the diameter usually steps down from about 5 mm (milimeter) down to about 1 mm. This results in about a thousand terminal bronchi that are located in in the outer third of the lungs (22). Many lung disorders, such as lung tumors, can occur in this region.

Unfortunately, this outer third portion of the lungs (22) is largely inaccessible to prior art bronchoscopes. This is because prior art bronchoscopes, including robotically driven bronchioscopes, typically have a minimum diameter of 3.5 to 4.2 mm Such devices are also difficult to maneuver through the many twisting of the bronchial tree, because such devices have limited flexibility (e.g. a limited or large articulation radii).

Prior art bronchoscopes and robotic bronchoscopes have about a 4 mm diameter and an 18-20 mm articulation radius. These prior art bronchoscopes are typically single stage catheters, often of continuous diameter, which are introduced into the lung with the aid of an introducer sheath. Occasionally medical practitioners attach a 19-22 gauge (~1 mm) flexible nitinol needle to the distal tip of the bronchoscope, and use this wire tip to reach still further into the lungs for lesion biopsy. However, such wire tips have limited flexibility and maneuverability (limited articulation), and are thus often unsatisfactory for this purpose. At a bronchial diameter of 4 mm, there are roughly 50 bronchi that can be accessed with prior art robotic bronchoscopes. As the bronchial diameter reduces to 3 mm, there are roughly 100 bronchi that can be accessed with with a 3 mm robotic bronchoscope, if one existed.

The invention is based, in part, on the insight that improved bronchoscopes with diameters below 3 mm can provide a 6 to 20 fold greater opportunity to detect and treat currently unaccusable cancerous lesions in the outer third of the lung. So at 3 mm, we in effect have a "biometric transition point" where prior art bronchioscopes fail, to proceed further along the ever smaller diameter lung bronchi.

3 mm diameter bronchioscope could access about 100 currently inaccessible bronchi 2.5 mm diameter bronchioscope could access about 300 currently inaccessible bronchi 1 mm diameter bronchioscope could access about 1000 currently inaccessible bronchi The invention is based on the further insight that using prior art flexible needles to extend the range is not adequate because such needles are not actively steerable. Such needles have a high risk of tearing through delicate vascular structures, because their trajectory will be approximately a straight path when they exit the prior art bronchoscope.

The invention is also based, in part, on the insight that what is needed is an improved bronchioscope, such as a two (or more) stage broncoscope, capable of extremely narrow distal diameters, as well as an ability to be precision driven. In some embodiments, this improved device may also utilize an introducer sheath, and be capable of having both stages that are robotically driven along the same axis.

FIG. 2 shows a close up of the various lung bronchus and bronchi pathways, showing the path transition points (104) where a second, narrower, stage of a two stage bronchoscope (100) can extend out from a wider first stage (See FIG. 3). The wider first stage (106) can guide the device through the larger diameter bronchus pathways, and position the narrower second stage (108) to then proceed further through the ever narrowing segmental bronchi and into the appropriate bronchiole nearest the target (often a potential lesion or tumor).

The challenges of such an improved device should be appreciated. As can be seen from FIG. 2, the bronchi branches take many sharp turns. For best performance, the improved bronchioscope device needs to articulate and navigate these ever smaller diameter paths. Thus again, at the Tertiary or Subsegmental Bronchi (3-6 mm diameter, 18), there are about 38 branches. But when the device is traversed beyond the 3 mm Tertiary branches, there are potentially a thousand or more 1000 branches in the Terminal Bronchi (the outer $\frac{1}{3}^{rd}$ of the lungs 22). Ideally, the design would allow the operator to articulate or manipulate the tip of the bronchioscope through each branch, without punching through or otherwise damaging the delicate vascular structures and/or bronchus walls.

The invention was also inspired, in part, on the insight that such an improved device should be able to do useful work once it reaches its destination. This includes an ability to robotically position useful sensors, such as cameras and lighting systems, obtain tissue biopsies, and administer effective therapy to tissue targets positioned at such difficult to reach locations.

As will be discussed, in some embodiments, the invention teaches robotic, processor-controlled, systems and methods of flexing and unflexing various portions of a hollow catheter by using tensioning actuators to create and release tension on various catheter steering cables while also rotating these steering cables in a 1:1 ratio with actuator controlled rotation of various portions of the hollow catheter. This enables the catheter to be driven into hard to reach portions of the body, while at the same time ensuring that the various steering cables and rotation operations do not interfere with each other.

BRIEF DESCRIPTION OF THE DRAWINGS

FIG. 11 shows how the flexible sections can be tailored to a patient's particular bronchi where the lesion location may be a more challenging area to reach due to some non-conformity
FIG. 12A and FIG. 12B show the use of optional electrodes

FIG. 38A and FIG. 38B shows an example of a robotic drive algorithm that drives the motors to create a wave between the distal and proximal stages. The distal stage is also rotating/threading itself into the bronchus.

FIG. 52 shows a more detailed cross-section of the device previously shown in FIG. 51.

DETAILED DESCRIPTION OF THE INVENTION

Figure 1:
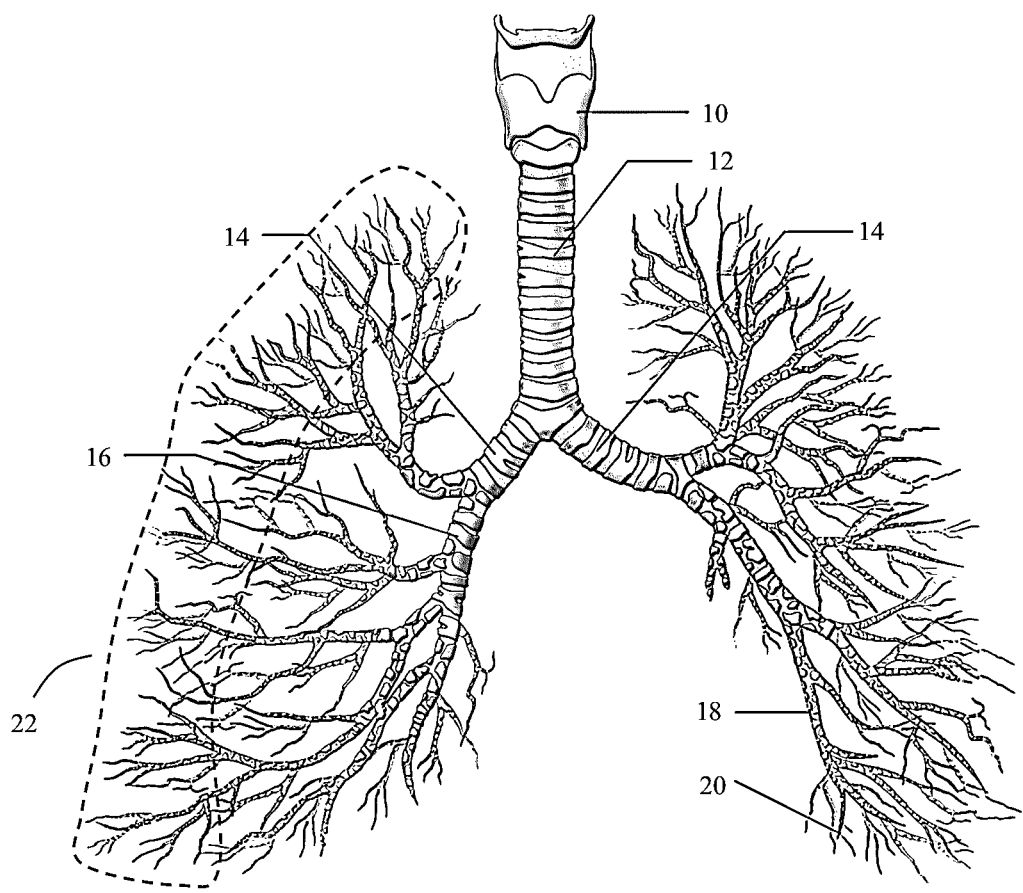
FIG. 1 shows the lung bronchus system.

There is a need to improve surgical procedures by reaching further into a particular area of the body with the most minimally invasive approaches. In all instances, the body's internal pathways follow a sequence of narrowing branches. The further down the branch or vessel, the narrower the internal pathway becomes. This creates many challenges for engineers. It pushes the creative and technological limits.

Catheter development is dependent on efficient implementation of metals, polymers, and semiconductors. Metals provide for higher stress limits and thus smaller parts which enable the production of smaller tools. Stainless and Nitinol metals are used in the skeleton of catheters and micro-mechanical tools. Polymers are used for the skin and insulation of the catheter, allowing smooth interaction between the tool and the body's pathways. Silicon provides the sensing and feedback for producing smart embedded devices at the distal portion of the catheter. Other electronic embedded elements can include video cameras, such CMOS cameras, and LED lighting. The CMOS camera and pico-LEDs provide an important advantage by allowing more flexibility (less resistance) at the distal lead and along the catheter's length. This is due to the braided electrical wires for power, return and communication leads. Whereas fiber optic scopes and fiber optic lighting limit the radius of bend or articulation angle of the catheter due to the higher bending resistance of the glass fibers.

Advances in robotics and visualization systems are creating new opportunities in medicine. These new opportunities create advantages over manual driven instruments. Stability is one of the advantages, and this is something easily recognizable when traditional manual surgical tools are attached to the robot. When catheters are robotically driven, several advantages can be leveraged: semi or full autonomous pathfinding, a locked position, drive methods for traversing further, and tracking position relative to the target with a real time C-arm surgical imaging device (CT or MRI).

Applying robotics to a catheter exhibits many challenges. Cost and performance must be well balanced due to a disposable cost model. New ideas that approach design for manufacturing (DFM) and cost from the initial challenge push both the creative and technological potentials.

The invention described tackles these challenges by exploiting advanced techniques in micro tool development coupled with robotics and visualization technology.

About nomenclature: in this disclosure, the invention will alternately be described as the invention, the device, the catheter, the bronchoscope, and even the robotically driven articulated bronchoscope. These terms are interconvertible, and the use of any given term in a specific context is not intended to be limiting.

Description of Applications (Curing Pulmonary Diseases)

Robotic procedures along with advances in real-time computer visualization of the body have opened entirely new approaches to targeting and curing many diseases. One such area is in the diagnosis and treatment of lung cancer. Most lung lesions are in the periphery of the lungs. Seventy percent of lung lesions are in the outer third of the lungs. This is a huge opportunity for applying micro-invasive technologies due to the narrowing of the bronchus in the periphery.

Current detection and treatment are limited by several shortcomings even with the application of robotics. For robotic bronchoscopy, the catheter technology is limited by cost constraints of the disposable, and this directly impacts the catheter size and mobility. Making devices smaller comes with many challenges which, if not approached carefully, can create cost and performance disadvantages.

These constraints provide a unique opportunity for innovation. It is achievable to reach and treat currently inaccessible lesions in the outer third of the lungs by applying creative methods of manufacturing. It is possible to develop a highly mobile sub 3 mm robotic micro-bronchoscope with the ability to safely target the outer third of the lungs. This is an area of the lungs where a thoracic surgeon must apply a biopsy needle under fluoroscopy by going transthoracic to obtain a tissue sample. Although this is the standard of care for the hard-to-reach areas of the lungs, it comes at a price with a pneumothorax rate of 20%. Additionally, this procedure does not provide a targeted treatment or cure if the lesion is found to be cancerous. It is only a diagnostic method. The cost of treating a 20% pneumothorax rate is a huge issue and a great opportunity for developing better methods of treatment.

The outer third of the lungs (22) is where 70% of lung lesions are located. Going transluminal from the bronchus to the outer third provides the opportunity during the same procedure to biopsy (detect) and treat the lesion if found to be cancerous. In addition to detecting and treating cancer, other illnesses such as chronic bronchitis could be treated with electroporation to illicit an immunogenic response. Another application would be targeted micro-lung-lavage at the Alveoli.

Figure 2:
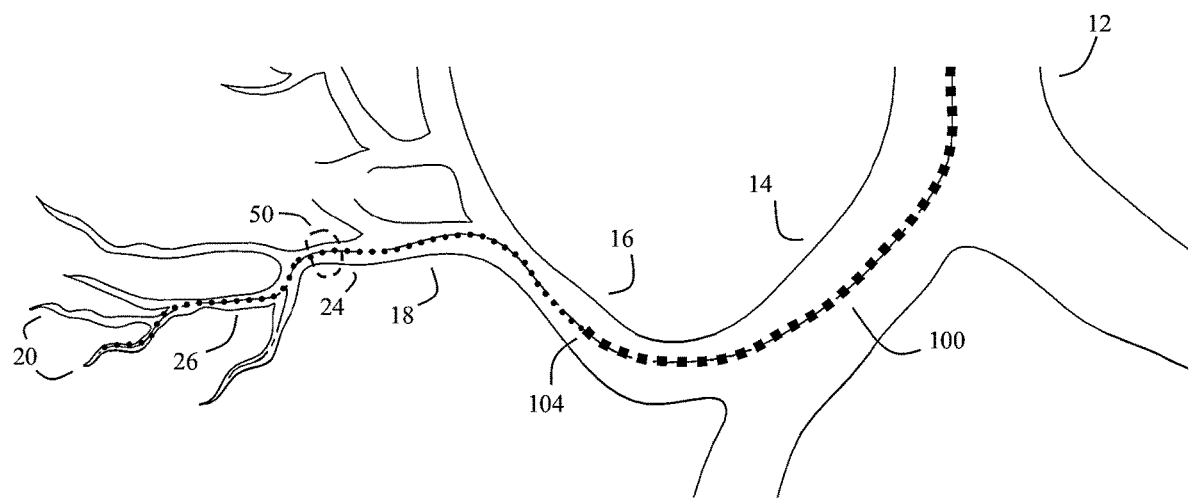
FIG. 2 shows the various bronchi structures and pathways
FIG. 3 a hypothetical path for the invention's bronchoscope reaching the outer ⅓rd of a lung.

FIG. 2 shows the trajectory paths from Primary (14) to Secondary (16) and then at the end of the Tertiary branch (18) where the pathway narrows to <3 mm in the subsegmental Bronchi. This is the transition to Terminal Bronchi. The thick dashed or broken line represents the path of a Bronchoscope (100). Along the scope's path, transition points are labeled. These points are labeled "End of Introducer Path" (104), "End of Proximal Path" (24), "Biometric Transition Point" (50), and "Distal Stage Path" (26). These labels represent some of the key areas along the length of the endoluminal catheter that is disclosed in this application.

As previously discussed, prior art robotic bronchoscopes have a diameter of about 4 mm, and also have about a 18-20 mm articulation radius (turning radius). Although, in some prior art situations, a 19-22 gauge (—1 mm diameter) flexible nitinol needle can be attached to the tip of the bronchoscope for lesion biopsy, such needles are difficult to steer, and tend to be unsatisfactory for many purposes.

Figure 3:
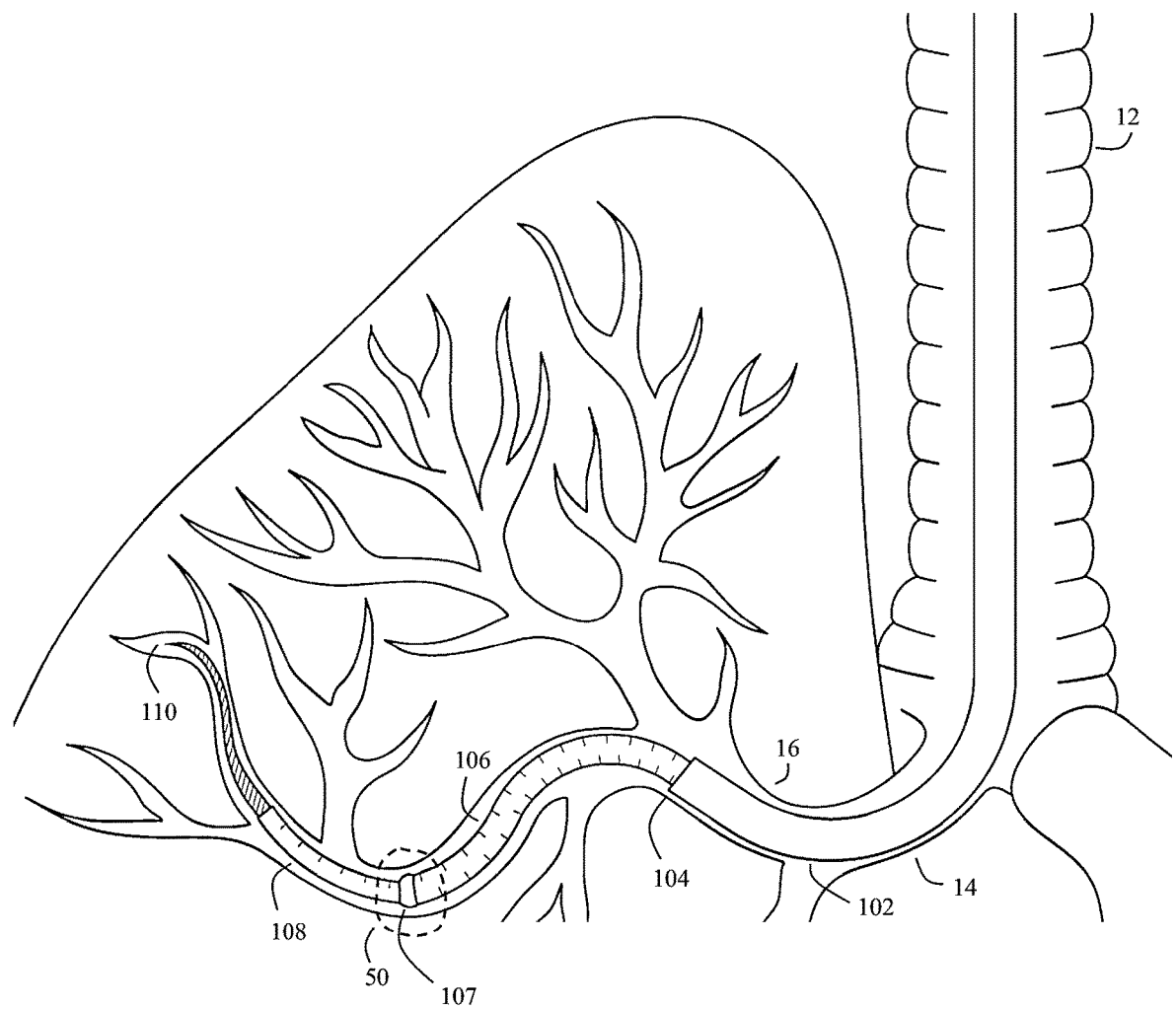

Based on the trajectory path in FIG. 2 and FIG. 3, the "Biometric Transition Point" (50) can be viewed as being the region of the lungs with bronchus and bronchi diameter of 3 mm or less, where prior art bronchoscopes stop.

As previously discussed, in some embodiments, the invention may be a two (or more) stage broncoscope with an introducer sheath (102) where both stages (106) and (108) are robotically driven along the same axis. FIG. 3 shows a close up of the path transition points that show where this two stage bronchoscope is divided (based on biometric data).

This is the challenge, especially where the bronchi branches take sharp turns. The narrowing of pathways below 3 mm diameter (50), creates a huge opportunity for an improved bronchoscope that can articulate and navigate these smaller diameter paths. For Tertiary or Subsegmental Bronchi (3-6 mm), there are 38 branches. When the bronchioscope is traversed beyond the 3 mm Tertiary branches (50), the opportunity rises to 1000 branches in the Terminal Bronchi (the outer third of the lungs 22). Beyond the Tertiary branches, this can be viewed as being biometric transition in the design of the two stage bronchoscope. The improved device and methods disclosed herein are designed to penetrate this (3 mm diameter or less) region of the lungs (22), which is generally maces sable to prior art manual or robotic bronchioscopes.

FIG. 3 shows the four main components of this improved catheter system: These are the introducer sheath (102), the proximal stage (106), the distal stage (108), and the probe or tool (110). At (107), there is a transition point where the proximal stage (106) is coupled to the distal stage (108). As will be discussed in more detail shortly, this coupling allows for the rotation of the distal stage (108) relative to (or about) the proximal stage (106). As can be seen in FIG. 3, the distal stage (108) typically has a much smaller outer diameter (OD) than the proximal stage (106). The device is often configured so that the surgeon or robot can manipulate the primary stage (106) and coupler or transition region (107) near the biometric transition point (50), and then use the distal stage (108) to proceed further into outer third of the lungs (22) or other difficult to access region.

In a preferred embodiment, the surgeon, with or without robotic assistance, will often manipulate (106), (107), and (108) in synchrony to get to a desired location near the target. Then a tool or probe, such as (110), may then slide out and extend to the target.

Figure 4:
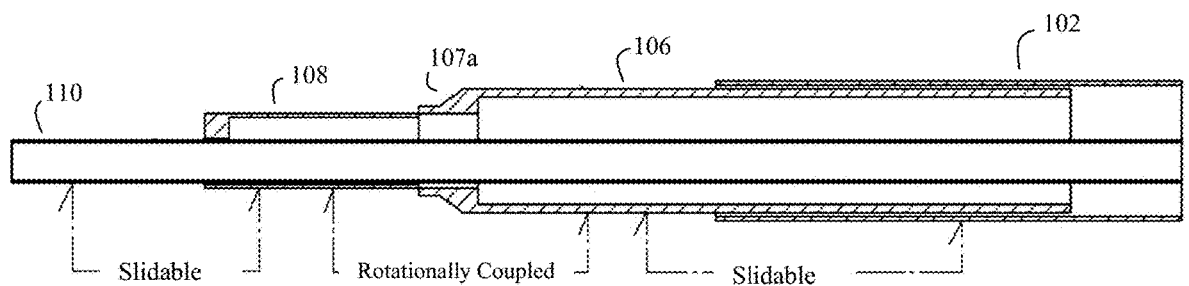
FIG. 4 shows a schematic cross-sectional view of the device's distal and proximal stages, showing where they are coupled, and how the distal stage is driven to rotate and flex relative to the proximal stage.

FIG. 4 shows a schematic cross-sectional view of the distal (108) and proximal stages (106) where they are coupled (107), and where the distal stage can be driven to both rotate and flex (relative to the proximal stage). Both stages can be slid into the lungs or other body lumen through the introducer sheath (102). Various tools and probes (110) can be extended (either manually or robotically) out of the end of the distal stage. The distal and proximal stages are typically configured to be slidable in the steerable introducer sheath (102), and the tools or probe devices are slidable (e.g., can slide in and out of) in the distal and proximal stages.

Figure 5:
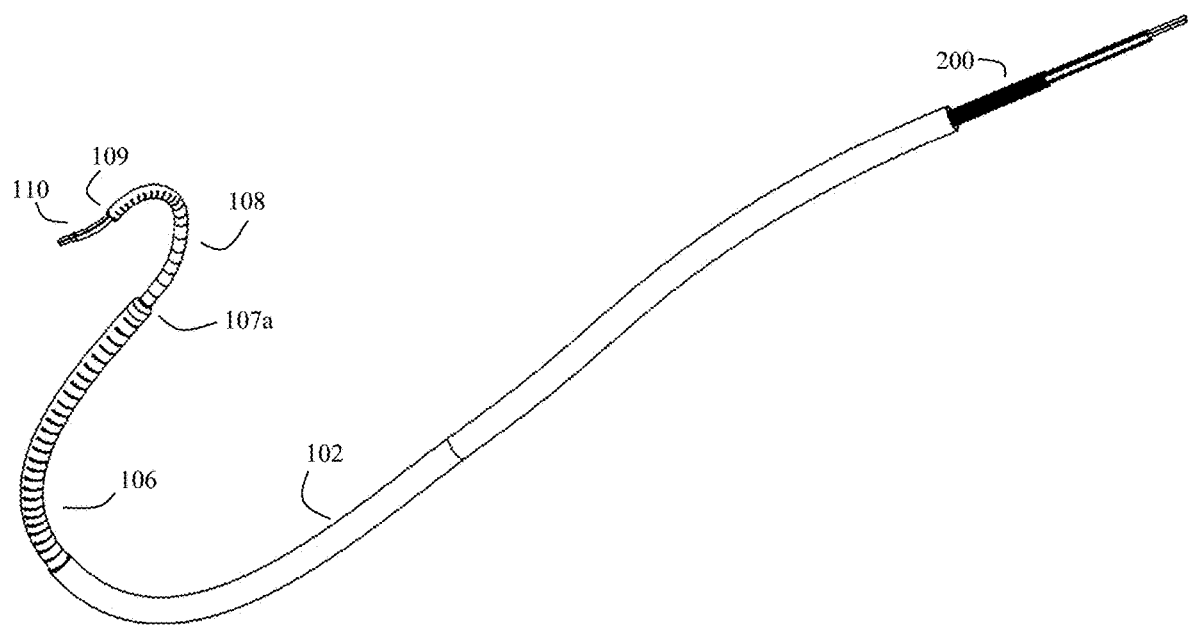
FIG. 5 shows another view of the device.

FIG. 5 shows another view of the dual-stage articulating rotary robotic bronchoscope. The distal stage (108) can rotate about the proximal stage (106). This feature allows a simple single-plane flexible catheter portion to rotate at the distal end, thus giving it a full 3-dimensional range of motion and maximizing the device's inner diameter (ID) for various devices such as camera, lighting, and tools; while minimizing the device's outer diameter (OD).

Other features shown on FIG. 5 will be discussed in more detail shortly.

As will be discussed in more detail shortly, in some embodiments, the invention may be a multi-stage catheter device. This device can comprise a distal stage hollow catheter (108) and a proximal stage hollow catheter (106), one end of this distal stage hollow catheter affixed to an end of the proximal stage hollow catheter by a hollow rotatable coupler (107b, also called a rotary joint) and transition housing (107a) configured to enable the one end of the distal stage hollow catheter (108) to rotate with respect to the end of the proximal stage hollow catheter (106). In some embodiments, the rotary joint (107b) and housing (107a) may be configured to be capable of being moved to at or near the biometric transition point (50).

The device will usually further comprise a hollow torque shaft (200) mounted inside the proximal stage hollow catheter. This hollow torque shaft is configured (200) to convey torque to the distal stage hollow catheter (108).

The device typically further comprises various conduits. These can comprise at least one proximal stage steering cable (210) connected to the transition housing (107a). This at least one proximal stage steering cable (210) is disposed inside the proximal stage hollow catheter (106), but outside the hollow torque shaft (200). This at least one proximal stage steering cable (210) is configured (or enabled) to convey proximal stage steering force on the transition housing (107a). This configuration causes the transition housing (107a) and the distal stage hollow catheter (108) to move according to the proximal stage steering force.

Figure 16:
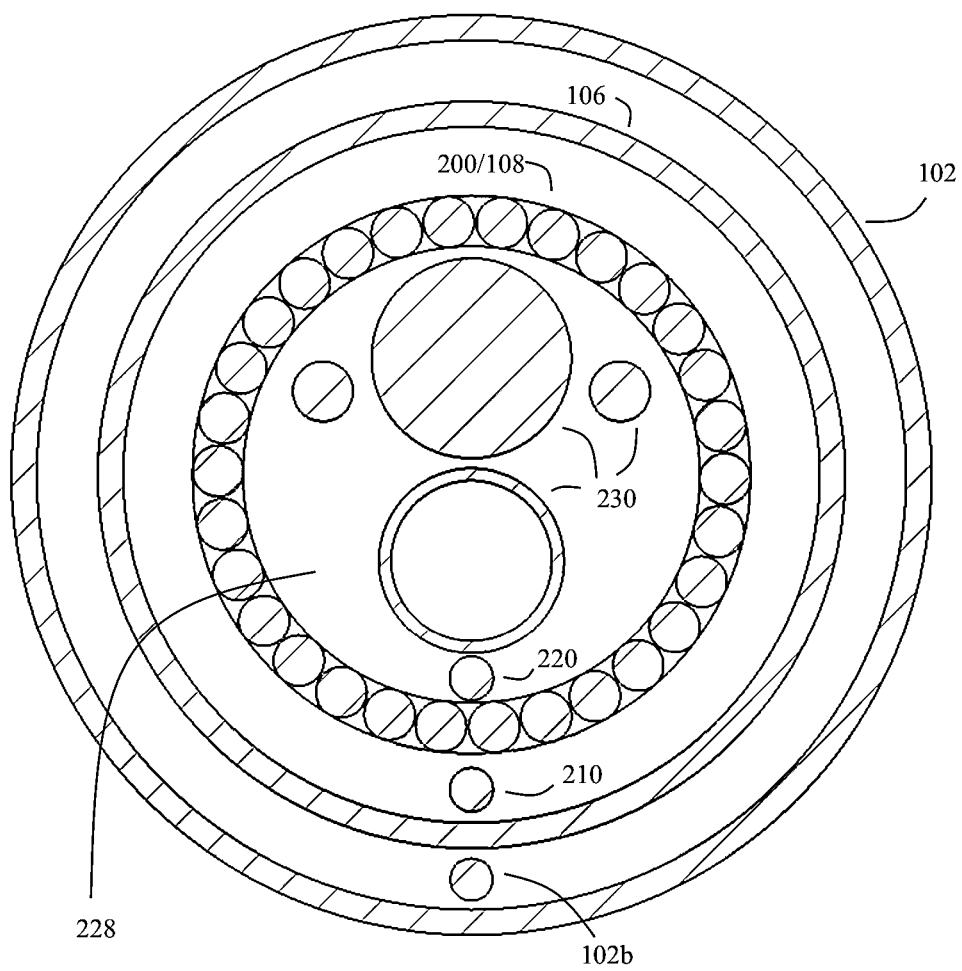
FIG. 16 shows a cross section of the system using a 1-way Steerable Introducer Sheath, 1-way Proximal Stage, 1-Way Distal Stage with Torque Steering.

As shown in FIG. 5, FIGS. 6A and 6B, and FIG. 16, The hollow torque shaft (200), the distal stage hollow catheter (108), the hollow rotatable coupler (107b) and the transition housing (107a) are further configured to comprise a working channel (FIG. 16, 228). This working channel configured to convey a plurality of other conduits through the proximal stage hollow catheter (106) and the distal stage hollow catheter (108) to at least a distal tool plate (109). This plate is mounted on a distal end of the distal stage hollow catheter (108).

Note that in some embodiments, (See FIG. 9B, and FIG. 27) at least some of these other conduits comprise at least one distal stage steering cable (220). These cables are connected to the distal tool plate (109) on the distal end of the distal stage hollow catheter (108). These distal stage steering cables (220, and optionally also 222, 224, and 226) are configured (or enabled) to convey distal stage steering force on (or to) the distal tool plate (109). This configuration causes the distal tool plate (109) and the distal stage catheter (108) to move according to the distal stage steering force.

Figure 6A:
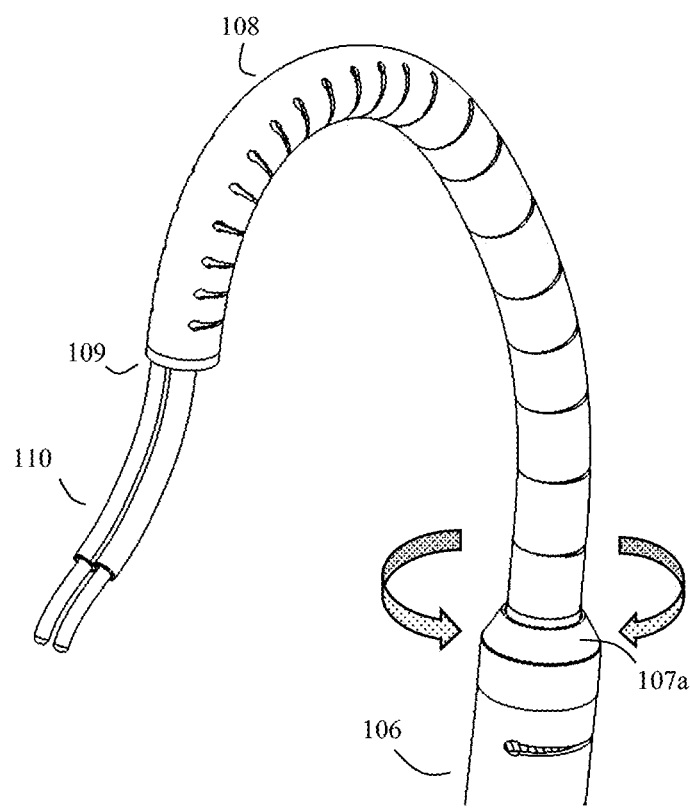
FIG. 6A and FIG. 6B show how the distal stage can rotate via a torque shaft while flexed to a curved position.
Figure 6B:
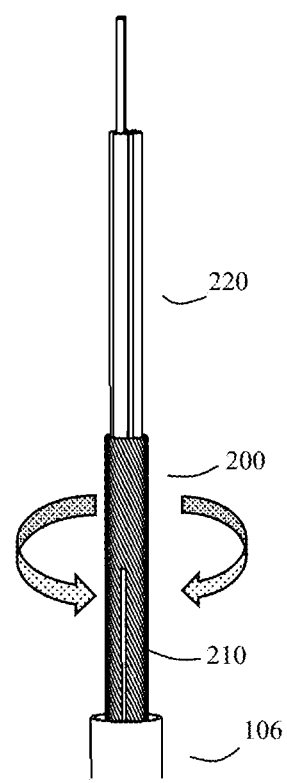

FIG. 6A and FIG. 6B show how the distal stage can rotate via a torque shaft while flexed to a curved position.

The torque shaft is rotated (200) while the proximal stage (106) is constrained from rotation. This torque is transmitted down the flexible shaft (200) with optimal torque transmission properties over long distances. The transmitted torque reaches the transition housing (107a) where it is transmitted to a coupler (107b) which causes the distal stage (108) to rotate.

When actuating the rotational portion of the distal stage (106), motor control can be used to help reduce the friction between coupler (107a, 107b) and the housing and proximal stage by quickly lowering cable tension (210) and pulsing the torque shaft (200) at a high rate of repetition. This force dithering technique is very important in rotating/actuating the small diameter distal stage over long distances as described.

Figure 7:
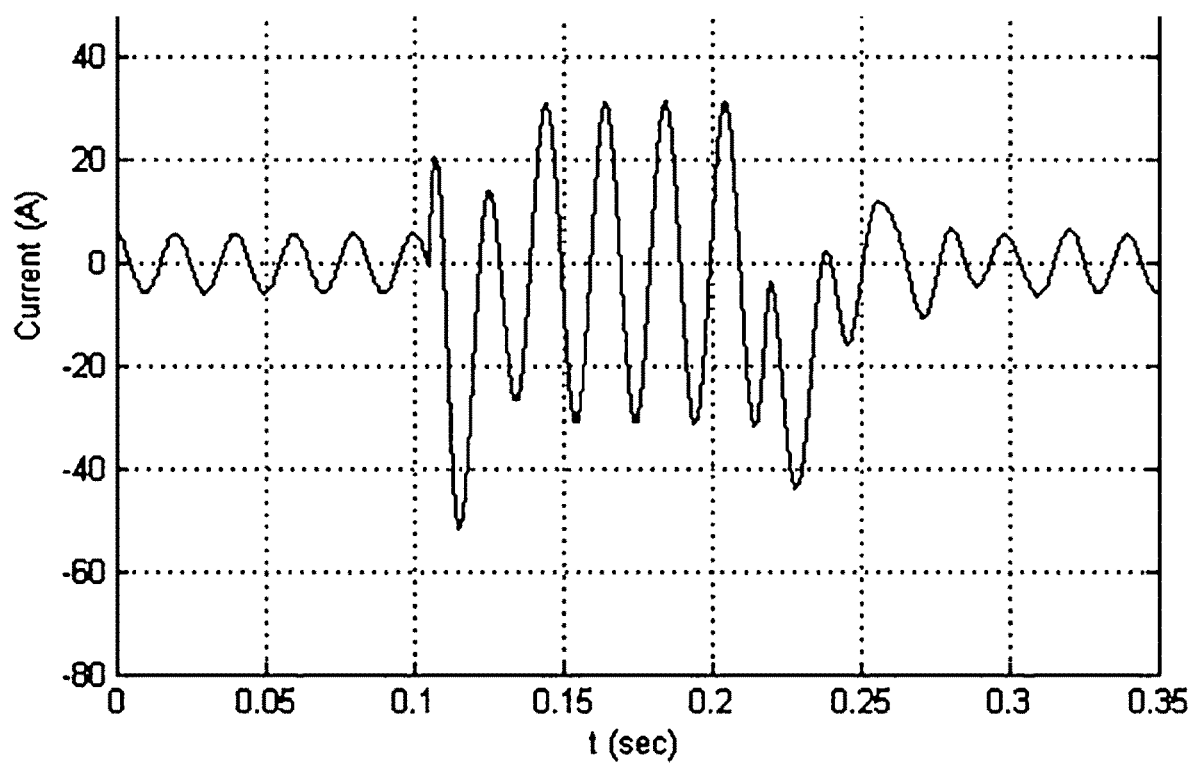
FIG. 7 shows the ripple drive waveform used by the drive amplifiers for breaking the frictional force and rotating/actuating the distal stage torque shaft.

FIG. 7 shows the ripple drive waveform that may be used by the motor/actuator drive amplifiers for breaking the frictional force and rotating/actuating the distal stage torque shaft (200).

Put alternatively, in some embodiments, the device can further comprise a computerized motor actuator system (See FIG. 20-21, 306, M) configured to apply variable torque to the hollow torque shaft (200). This motor actuator system can also be configured to provide variable tension to any of the proximal stage steering cables (210, and optionally also 212, 214, and 216) and/or the distal stage steering cables (220, and optionally 222, 224, and 226). In some embodiments, a given actuator (motorized actuator) can comprise multiple components, such as a drive wheel (306) and a motor (M). Depending on the embodiment, these components may be combined or separated, but for simplicity, here we will usually refer to these components as actuators. In any event, the actuator will usually translate a control signal (often from a computer processor) into a mechanical displacement (often of a conduit such as a steering cable).

FIG. 7 shows the ripple drive waveform that may be used by the drive amplifiers for the actuator system (306, M) for breaking the frictional force and rotating/actuating the distal stage torque shaft (200).

In some embodiments, the computerized motor actuator system (306, M) may operate according to an algorithm configured to reduce friction, while still guiding the catheter to a desired location. This algorithm may operate by repetitively lowering the variable tension (on cables 210 . . . 216 or 220 . . . 226) to first reduce friction. Then the actuator may apply torque (on the shaft (200) to partially rotate the distal stage hollow catheter (108). The algorithm may then reestablish tension (by increasing tension on cables 210 . . . 216 or 220 . . . 226) to guide the catheter to the desired location. In a preferred embodiment, the algorithm is configured to impart a rapid change in tension and torque so as to produce a smooth controlled actuation of the distal stage.

Figure 8:
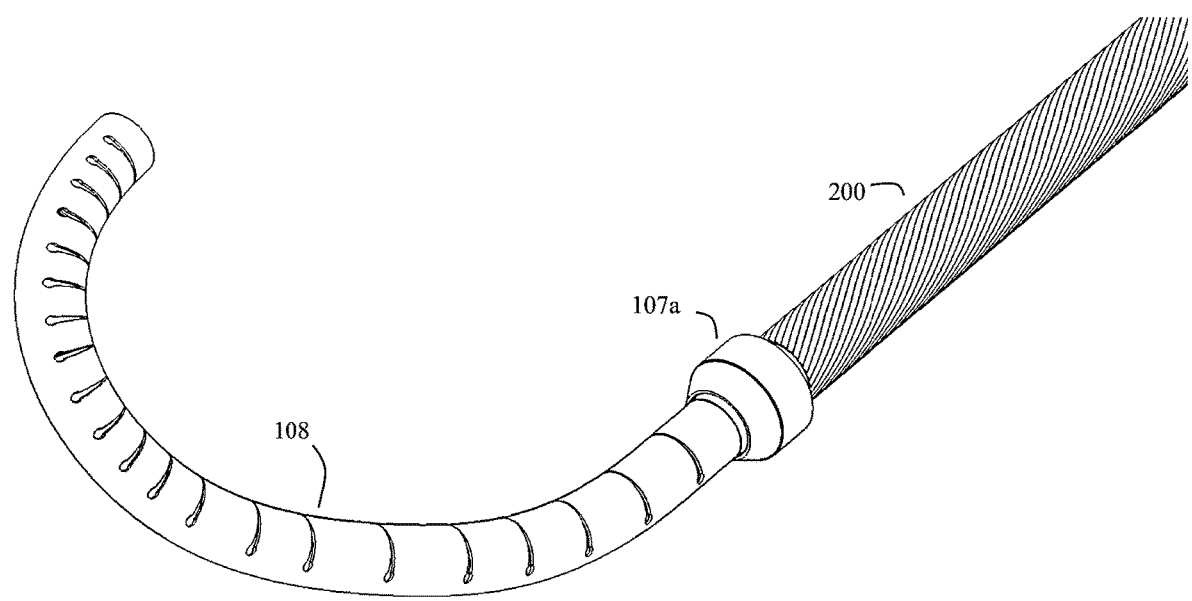
FIG. 8 shows the details of the distal stage with its torque shaft (multi-filar) exposed

FIG. 8 shows the details of the distal stage with its torque shaft (200, here composed of multiple strands) exposed (this would normally be hidden by the proximal stage 106, here not shown). The torsion steering drive tube (also called shaft 200) is made up of an array of wires arranged circumferentially with an angle of twist or spiral where each wire runs the full length of the catheter without interruption. This continuous arrangement of wires transmits torque with the least amount of hysteresis while allowing the shaft to be flexible.

Figure 9A:
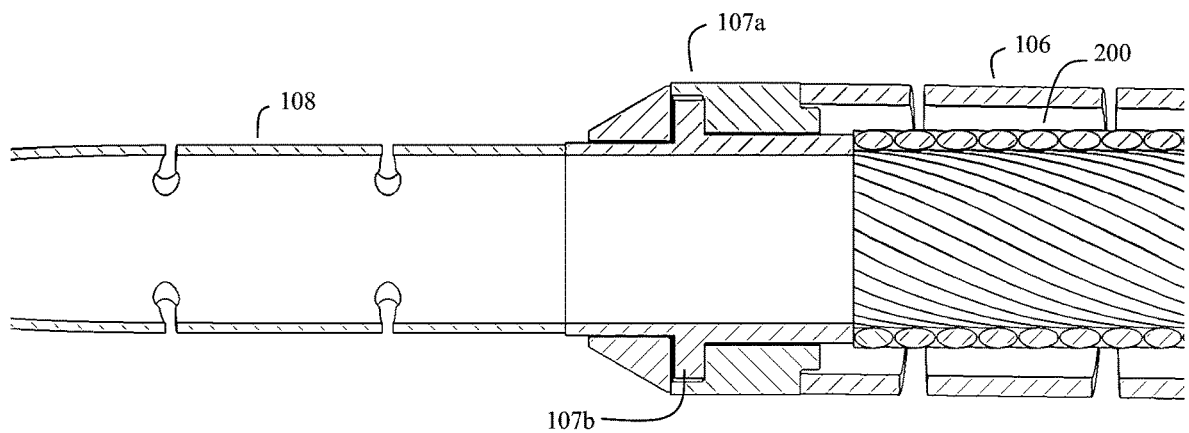
FIG. 9A shows a cut section of the transition housing and how torque is applied to the to the distal stage while the proximal stage remains stationary.

FIG. 9A shows a cut section of the transition housing (107*a*), showing how the drive shaft (200) applies torque to the distal stage (108), while the proximal stage (106) remains stationary. Note that often, the transition housing (107*a*) also comprises a rotating section (107*b*), called the hollow rotatable coupler, that is attached to both the distal stage (108) and the torque shaft (200). In general, unless otherwise specified, assume that the transition housing (107*a*) also includes the hollow rotatable coupler (107*b*).

Note that in some embodiments, the torque shaft (200) can alternatively be made from a laser cut hypo-tube such that is it flexible and also able to transmit torque. As another alternative, the torque shaft (200) can also be made from a metal or plastic fiber braided sheath and covered in a pliable polymer.

Figure 9B:
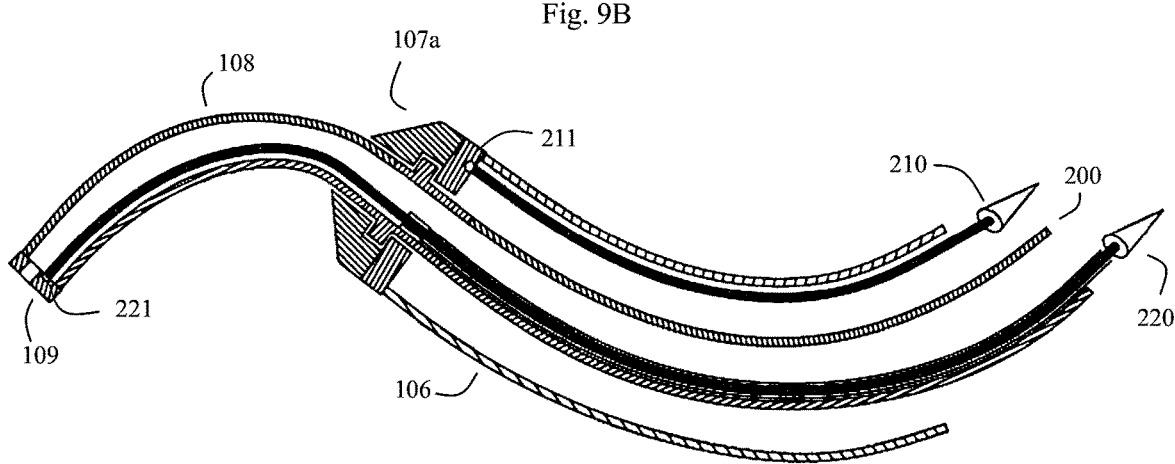
FIG. 9B shows a cut section of the transition housing, also showing how the conduits operate

FIG. 9B shows a cut section of the transition housing, also showing how the conduits (here cables 210 and 220) operate. Here conduit (210) is configured as a proximal stage steering cable. That is, the conduit or steering cable is disposed inside the proximal stage hollow catheter (106), but outside the hollow torque shaft (200). It is configured to convey proximal stage steering force on the transition housing (107*a*), here by attachment point (221). By contrast, conduit (220) is configured as a distal stage steering cable.

Figure 10:
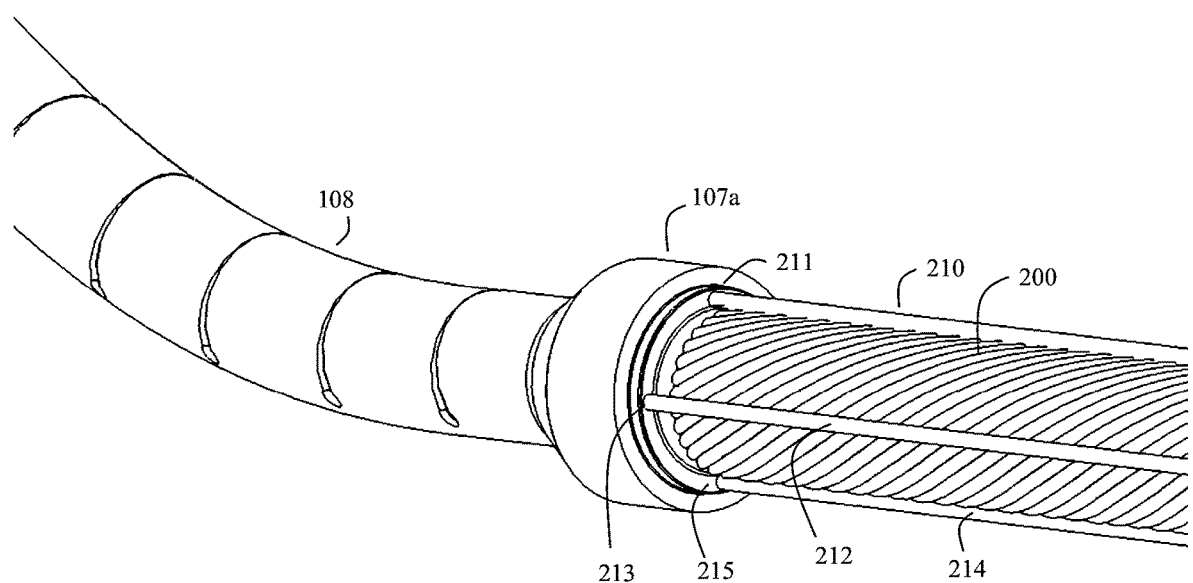
FIG. 10 shows how the proximal steering cables are attached to the transition housing. These cables run the length of the proximal stage all the way up to the drive mechanism.

FIG. 10 shows a further detail of how the conduits may be proximal steering cables (here four cables 210, 212, 214) can be attached to the transition housing (107*a*) at connection points (211, 213, and 214). These cables run the length of the proximal stage (106, not shown) all the way up to the drive mechanism.

FIG. 11 shows how the flexible sections (106 and 108) can be tailored (e.g., custom manufactured) to better fit a patient's particular bronchi where the lesion location (e.g., target) may be a more challenging area to reach due to some pathway non-conformity.

FIG. 11 also shows that any of the distal stage hollow catheter (108) and the proximal stage hollow catheter (106) may further comprise a plurality of slits (such as 108*a*, 106*a*) along at least a portion of their circumference. These slits may have positions and dimensions that are configured to facilitate catheter traversal through a series of branching body lumens of progressively smaller internal diameters.

In some embodiments, the structure of a patient's particular pathway may be obtained by scanning (e.g., by using a C-arm medical imaging scanner or other type scanner to scan the patient, and to create a computed 3D model of the patient). This computed 3D model can be generated before surgery. This pathway data from the model can be used to determine the ideal trajectory of the distal stage (108). This distal stage design could be automatically generated, such as by standard computer processor or AI methods, using current patient scans. (e.g., CT/MRS generated 3D models and historical data/3D scans). This data can be used to determine exactly how to construct the distribution and flexibility of any optional flexure joints (108*a*, 106*a*) along the distal and proximal stages (106, 108), as well as the length of the distal and proximal stages.

FIG. 12A and FIG. 12B show the use of optional electrodes, such as (110*a* and 110*b*), here shown extending out of distal plate (109). In some embodiments, bipolar (e.g., two) electrodes may be used for targeted treatment, and can be used to deliver high frequency electrical energy from a suitable source. These micro electrodes (110*a*, 110*b*) can be isolated from one another by an insulating lumen. In some embodiments, the electrodes may be made from DFT® wire (Drawn Filled Tubing). Such DFT wire may comprise a gold core electrode (120) surrounded by nitinol (122), and often then an insulator (124). This allows for elasticity and conductivity to be optimized in small diameter wire <1 mm More conventional wires, such as insulated copper wires, may also be used (126). In some embodiments, these wires will also have radiopacity for viewing position of electrodes during a real-time C-Arm CT scan or other imaging process.

Thus, although some of the conduits may often comprise tension or steering cables such as (210), and (220), at least some of the conduits may also comprise electrical conduits (such as 110*a*, 110*b*). These electrical conduits may be used to transmit any of electrical power or electrical signals to any of probes, sensors, or other electrically activated devices disposed on or passing through the distal tool plate (109).

Note further that in many embodiments, at least some of the conduits comprise any of optical fibers or hollow tubes configured to convey any of optical, electromagnetic, or radiofrequency (RF) signals or chemicals to or from devices disposed on the distal tool plate (109).

Figure 13:
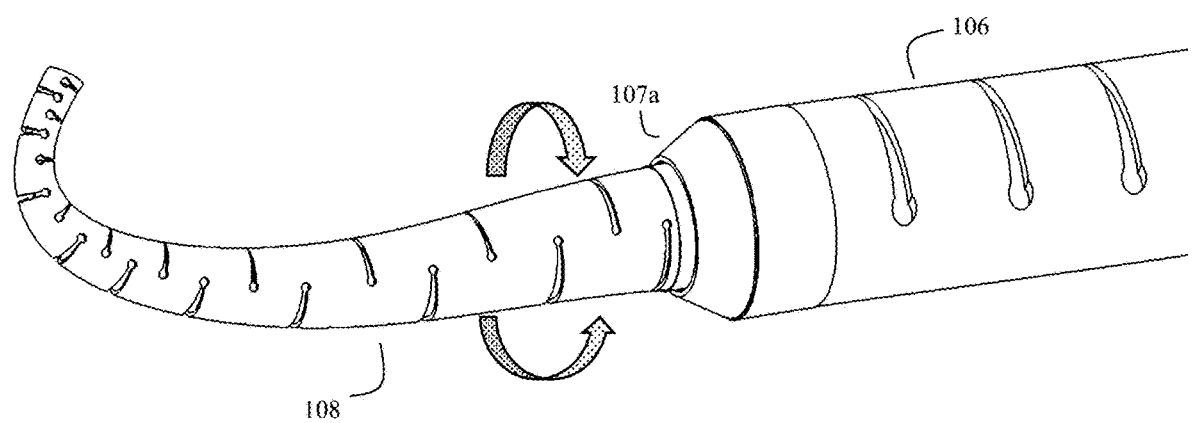
FIG. 13 shows the Distal Stage as 2-way produced from a tapered laser cut tube

FIG. 13 shows that in some embodiments, the distal stage (106) may be produced from a tapered tube, such as a tapered laser cut tube. This embodiment can be useful to help scale the distal stage (108) to a patient's individualized anatomy, both in diameter, length, and shape of curvature.

More specifically, in some embodiments, at least the distal stage hollow catheter (108) may be tapered from a larger external diameter at the hollow rotatable coupler (107*a*, 107*b*) to a smaller external diameter at a distal end (at or near the distal plate 109) of the distal stage hollow catheter. Further, the device may be configured to enable at least distal portions of the distal stage hollow catheter (108) to be maneuvered though body lumens with internal open diameters of 3 millimeters or less (see FIG. 2 and FIG. 3, 50).

Although the device disclosed herein may be used for many medical and veterinary applications, in some embodiments, the body lumens may comprise any of trachea (12), primary or secondary or tertiary bronchus or bronchi, or bronchiole (12, 14, 16, 18, 20). Here the device may be specifically configured as a bronchoscope.

Figure 14:
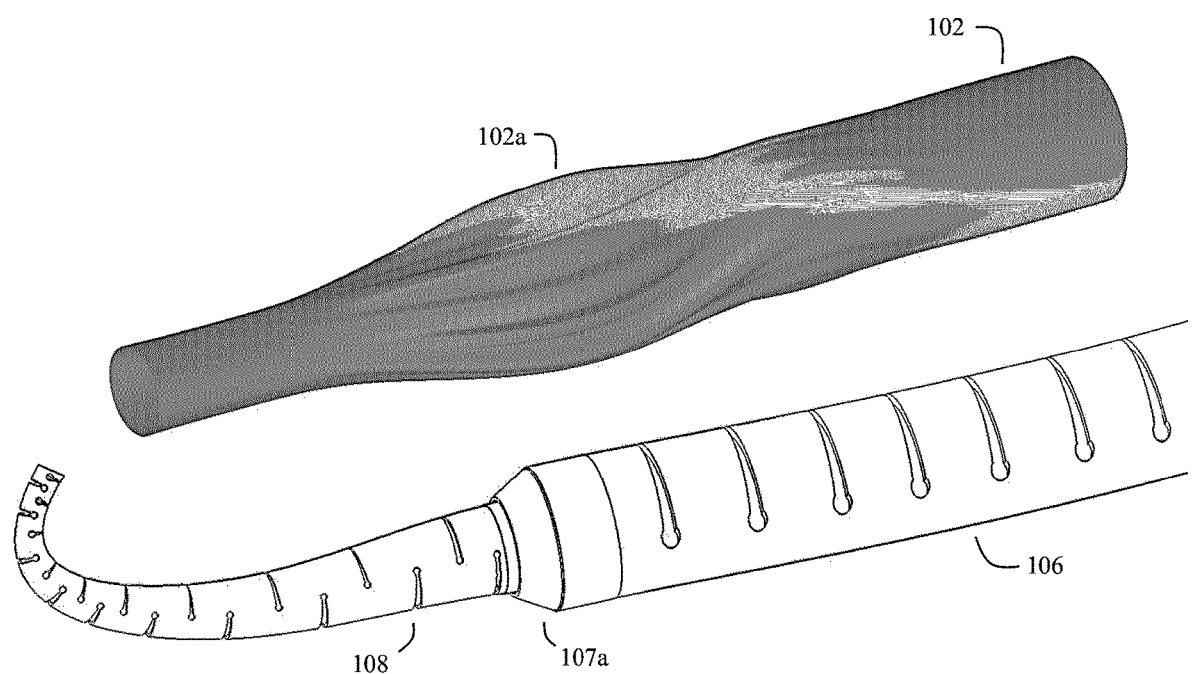
FIG. 14 shows a detail of a flexible sheath that may cover at least portions of the distal and proximal stages.

As shown in FIG. 14, in some embodiments, a flexible sheath or jacket (102) will cover at least portions of both distal and proximal stages (108, 106). This can be used in both bronchioscope applications as well as other applications such as where the device is applied to the blood stream. Other types of flexible coverings, distinct from any introducer sheath, may also be used as desired.

In the application of bronchoscopy, there can alternatively be two sheaths covering stages (106, 108), one sheath for each stage, so the the rotary portion at the transition housing (107a and/or 107b) is free to rotate in either direction without restriction. Depending on the requirements for other locations in the body, i.e. blood vessels, the sheath can be contiguous, and at the area of the transition housing (107a) the sheath is not adhered. This allows for an extended amount of rotation in either direction of at least 360 degrees.

FIG. 14 also shows how, in some embodiments this sheath need not be tightly adhered to the device at the area around the transition housing (107a). Instead, the sheath may have some slack (102a) at this region. This allows some degree of rotation with a single sheath design Put alternatively, in some embodiments, at least proximal portions (such as the 106 region) of the proximal stage hollow catheter may be disposed within at least one hollow sheath (102). As shown in FIG. 4, at least a portion of this at least one hollow sheath can be configured to enable at least portions of the multi-stage catheter device (either 106 or 108) to be slide (e.g., protrude or retreat inside and outside of this at least one hollow sheath (102). This can depend on forces applied to this at least one hollow sheath (102) and at least the proximal stage hollow catheter (106).

Figure 15:
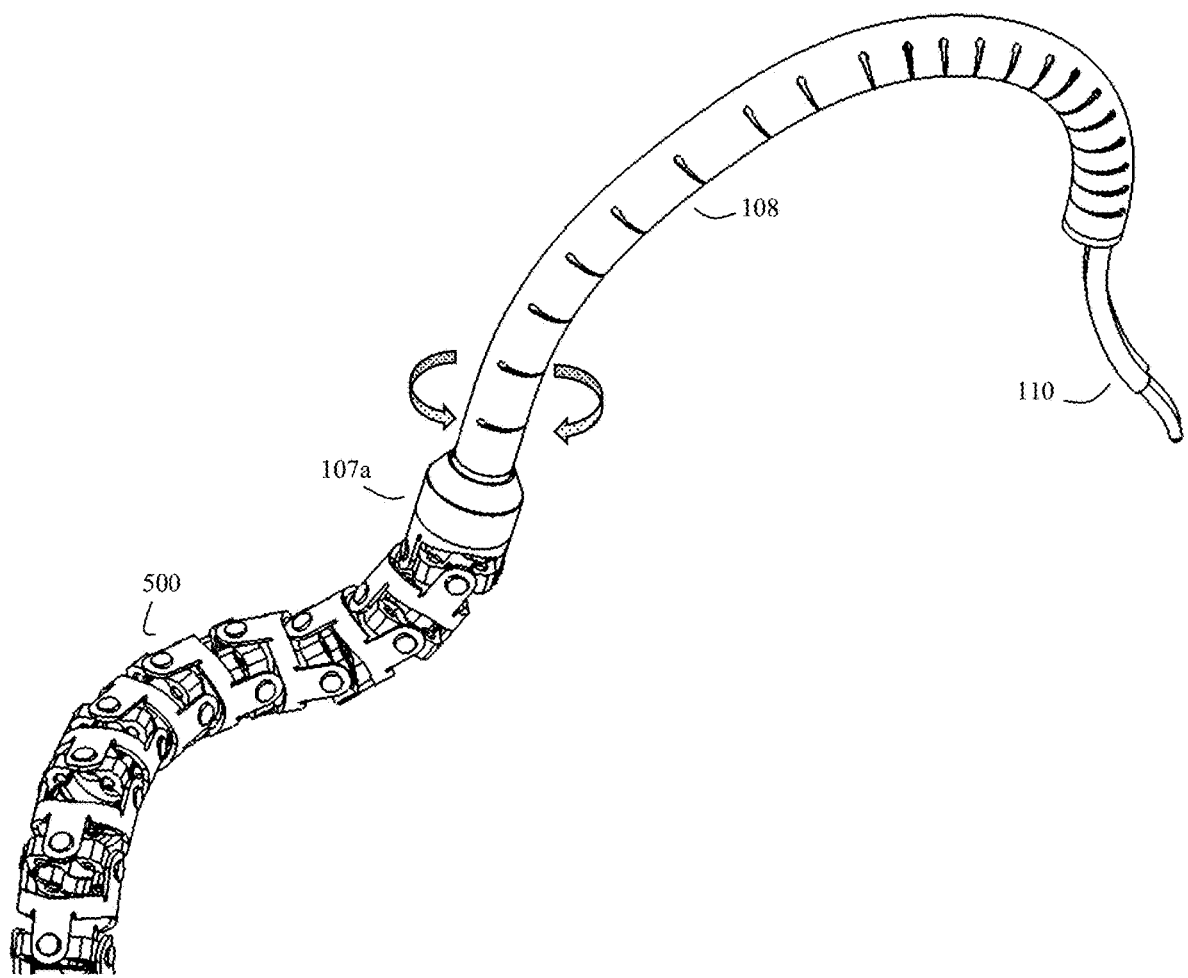
FIG. 15 shows an embodiment where the proximal stage is a 4-way type link system.

There are many combinations of flexure types for either the distal or proximal stages. FIG. 15 shows that in some embodiments, instead of being a catheter, the proximal stage may even be a 4-way link type system (500), such as that taught by Schmitz, U.S. patent application Ser. No. 18/186,176 and/or Schmitz, U.S. Pat. No. 1,103,342) coupled to a rotatable 1-plane/1 direction laser cut (e.g., laser slit, or slit) hypo-tube or other type of tube for the distal stage (108). This allows for full 3D articulation (X, Y, Z axis) from a very simple 1-way device.

For steering the catheter, there can be up to 4-way (e.g. four steering cables) steering in the case of the yoke and link system (or other 4-way links) shown in the previous images. The most simplified method uses all 1-way (e.g., one steering cable) capability with the distal stage (108) having both 1-way (1 steering cable) and distal stage rotational freedom (provided by torque shaft 200) passing through the proximal stage (106).

Here the terms "1-way steering" generally mean that there is one steering cable. Similarly 2-way steering implies two steering cables, 3-way steering means three steering cables, and 4-way steering implies 4-way steering. The use of 1-way steering in some of the figures and examples is not intended to be limiting.

FIG. 16 shows a cross section of the system using a 1-way steerable introducer sheath (102) with its own steering cables (such as 102b), a 1-way proximal stage (106) with steering cables (such as 210) a 1-Way distal stage (108) with a hollow torque shaft (200) and its own steering cables (such as 220). Other types of conduits (230) are also shown. This produces the smallest diameter catheter at the Distal Stage with the least complex design and the most efficient DFM while pushing the performance of the device for reaching the outer third of the lungs.

Figure 17:
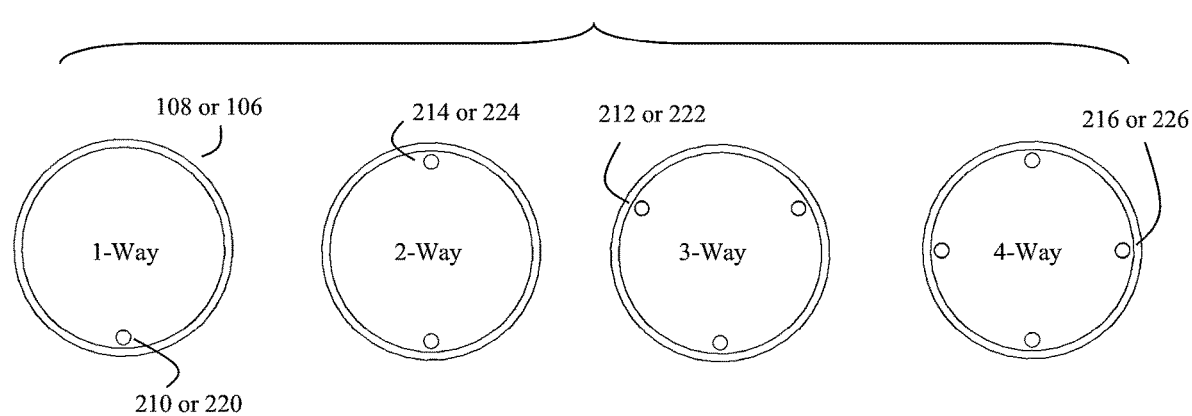
FIG. 17 shows the different pull wire orientations for each type of flexible system: 1 plane/1 direction (1-way), 1 plane/2 direction (2-way), 3 plane 3D (3-way), and 4 plane 3D (4-way).

FIG. 17 shows the different pull wire or steering cable orientations for each type of flexible system, here using either the proximal (106) or distal stage (108) cables as an example: 1 plane/1 direction (1-way), 1 plane/2 direction (2-way), 3 plane 3D (3-way), and 4 plane 3D (4-way). Technically, the 4-way has the highest degree of freedom. The 3-way is least practical. The 1-way and 2-way are most economical, and the 1-way (one steering cable) with the coupled rotational element (e.g., 200, 107a, and 107b) produces the highest performance in the smallest outside diameter where a working channel, camera, and lighting are required.

System Integration Example

Figure 18A:
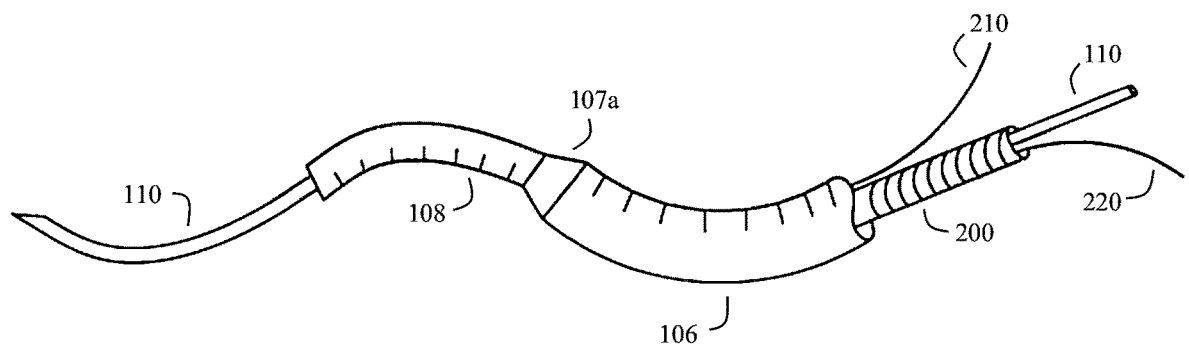
FIG. 18A, FIG. 18B, and FIG. 18C show an example of different steering cable configurations.
Figure 18B:
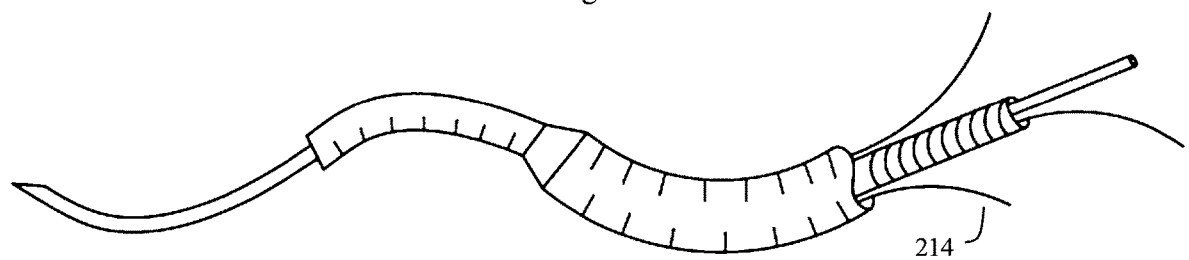
Figure 18C:
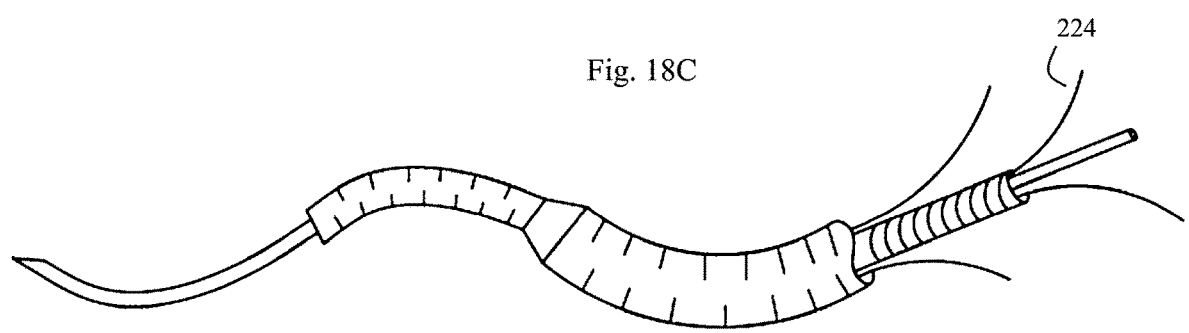

FIG. 18A, FIG. 18B, and FIG. 18C show an example of different steering cable configurations. In FIG. 18A, the proximal portion (106) has 1-way steering due to cable (210), and the distal portion (108) has 1-way steering due to cable (220). In FIG. 18B, the proximal portion has 2-way steering due to cable (210) and additional cable (214), while the distal portion still has 1-way steering. In FIG. 18C, the proximal portion (106) has 2-way steering, and the distal portion (108) now has 2-way steering due to new cable (224).

Figure 19:
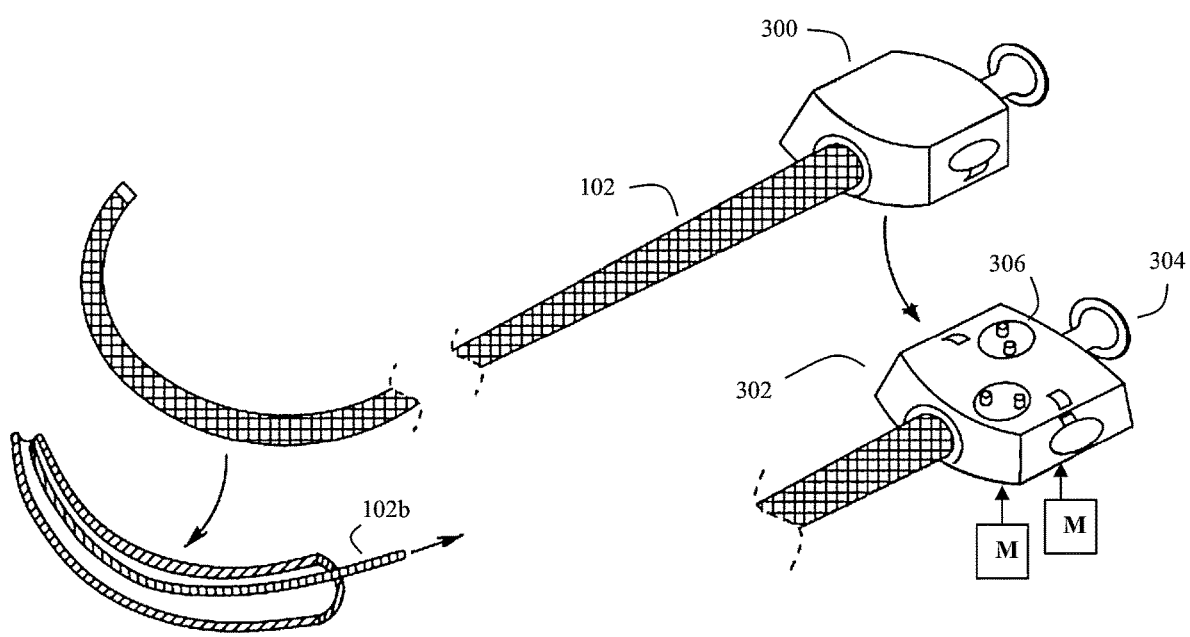
FIG. 19 shows a system example with a steerable introducer sheath control head.

FIG. 19 shows a system example of a steerable introducer sheath attached to drive cartridges for a robotic system. The first cartridge or control head (300) can actuate the introducer sheath (102) to bend/flex or rotate. This hollow sheath can be used for the delivering the rotary articulatable catheter (device). In a preferred embodiment, this sheath and control head arrangement may have at least one plane of articulation (at least 1-way steering) in at least one direction. In other embodiments, the hollow-sheath and control head may have up to full universal articulation (e.g., 4-way steering). In FIG. 19, the top figure shows the outside of the control head/sheath system, while the lower figure shows some of the mechanisms inside the control head/sheath system, such as a sheath articulation cable 102b and various drive wheels (306) and motors (M), often referred to as actuators (306) that can be used to manipulate the one or more sheath articulation cables.

In other embodiments, the "sheath" can comprise a mechanism that collapses but does not buckle.

FIG. 19 also shows that the articulation introducer sheath can have at least one plane and one direction of articulation (here using sheath articulation cable 102b) with an axis of rotation located at the control head housing (300, 302).

Put alternatively, in some embodiments, the multi-stage catheter device can further comprise at least one control head (300,). This at least one control head may comprise a hollow introducer sheath (102) and insertion funnel (304), configured to admit at least portions of the multi-stage catheter device (e.g., 106, 107, 108, 109), through the insertion funnel and hollow introducer sheath, and into a body lumen.

Figure 20:
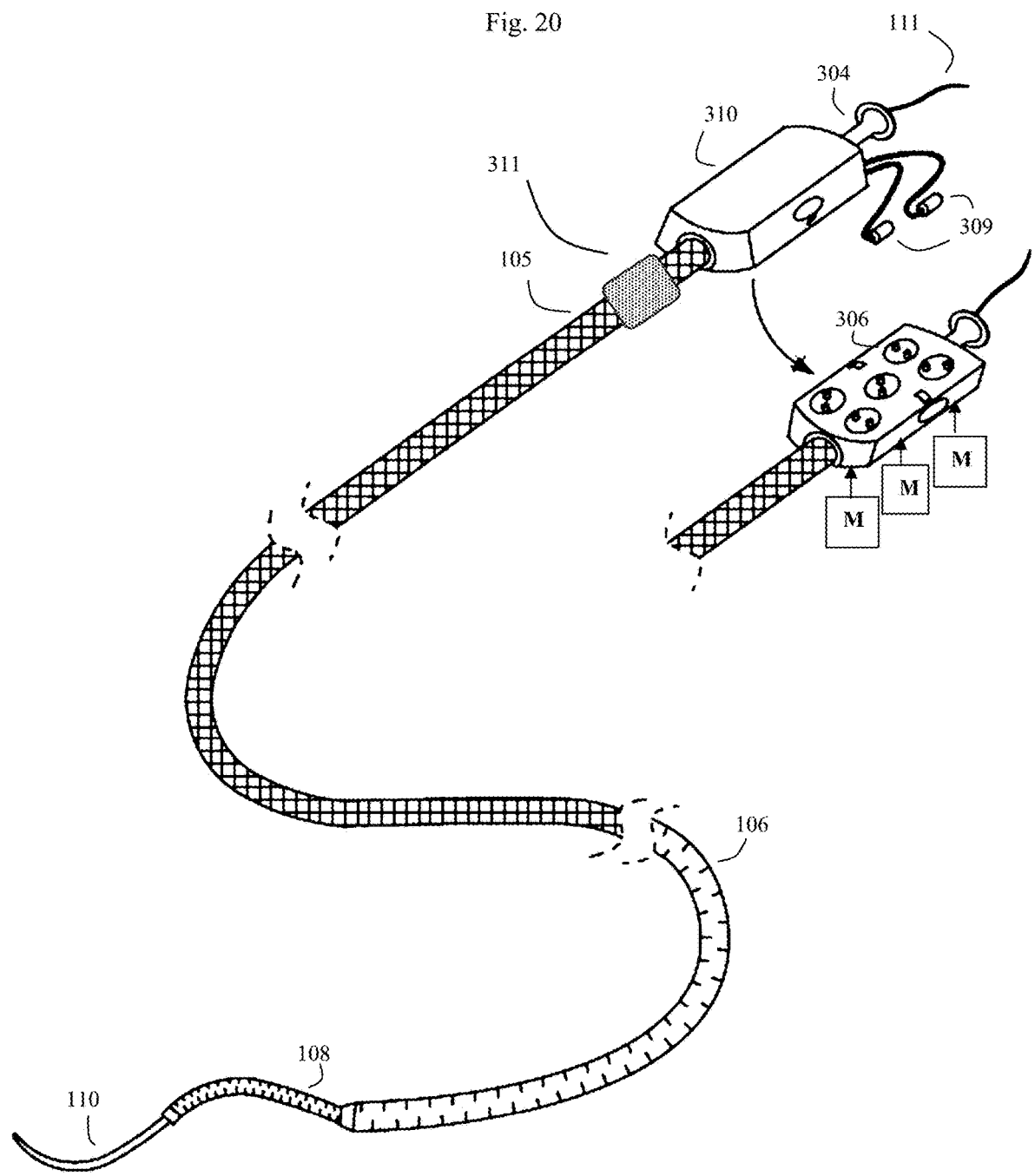
FIG. 20 shows another example of the articulating rotary robotic bronchoscope control head.

FIG. 20 shows an alternative embodiment of the articulating rotary robotic bronchoscope device control head, here designated as (310), showing other portions of the device, such as an extreme proximal portion (105) that connects to the proximal portion (106), the distal portion (108), and other portions. (Here, (105) can be viewed as an extreme proximal portion of the device that may have different flexibility than the proximal region (106), and although configured to be flexible, need not be necessarily be configured to be steerable.) A conduit (111) that connects to the tool tip (110) after passing through insertion funnel (304) is also shown. This control head may also have additional drive wheels (306) and motors (M), often referred to as actuators, which are often processor controlled motorized actuators, which are used to control other articulation/steering cables. Other devices shown (309) are connectors and interfaces to operate and control other conduits, such as cameras controlling cameras, lights, sensors, position indicators, electrodes, tool tips, and the like. Note that for simplicity, the introducer sheath is not shown.

Thus, in some embodiments, the at least one control head (300, 310) may be further configured with at least one computerized drive wheel (306) and motor (M), often called a motor actuator, or sometimes just an actuator. This at least one computerized motor actuator may be configured to perform any of:

Apply variable torque to the hollow torque shaft (200); and/or

Apply variable tension to any of the at least one proximal stage steering cable (210) and/or at least one distal stage steering cable (220); and/or As per the FIG. 19 introducer sheath discussion, also apply variable tension to at least one sheath steering cable (102b) disposed inside the hollow introducer sheath (102).

Although the various actuators, such as the previously discussed drive wheel (306) and motor (M) arrangements, may be part of the control head (300 or 310), in some embodiments, the actuator system may have some actuator components, such as the drive wheels (306) mounted on the control heads (300, 310), and have other components, such as the motors (M), mounted on a robotic system, such as a robotic arm.

In some embodiments, the control head (310) or an optional manual grip structure (311) attached to the sheath (102) may be used to apply manual force to the sheath if this is needed.

Note that in some embodiments, the systems shown in FIGS. 19 and 20 may be configured to be either disposable or reposable (able to be recycled a limited number of times) and will often be delivered pre-sterilized and in sterile packaging. The drive wheels (306) can be part of the disposable or reposable system, and the motors (M) that interface with the drive wheels may be configured as part of the durable medical equipment (such as part of a robotic system). After installation, the motor portions (M) may attach and detach from the drive wheels (306).

Figure 21:
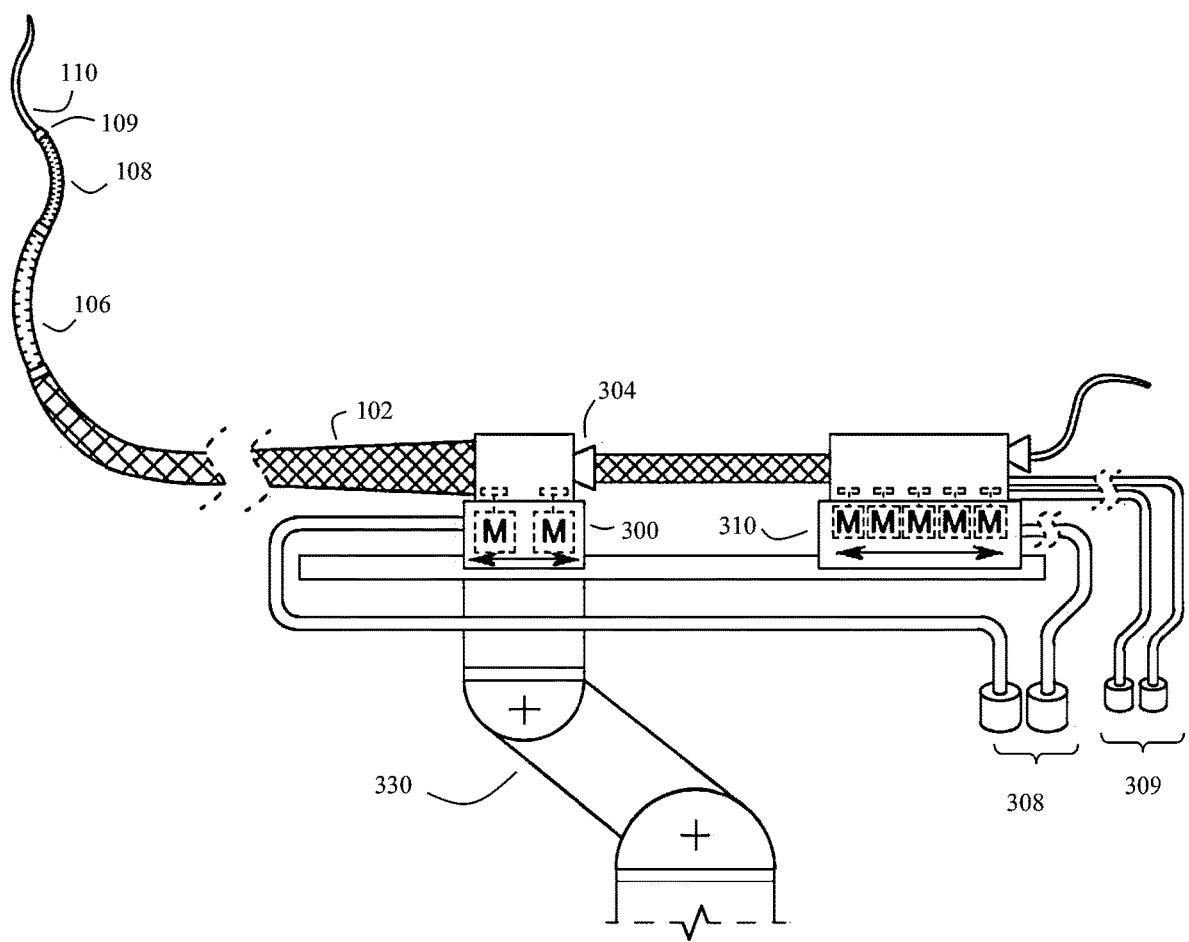
FIG. 21 shows the device implemented on a robotic system where both steerable sheath and steerable bronchoscope control heads are mounted and move independently of each other.

FIG. 21 shows the device implemented on a robotic system where are two control heads (300, 310), both are mounted (here on a robotic arm 330), containing blocks of motors "M" that can interface with the drive wheels (306) on the control heads. In this configuration, both control heads are are configured to move independently of each other, and along the same axis.

In FIG. 21, the computerized motor actuator system comprises two control heads (300, 310). These are mounted on the processor controlled robotic arm (330). This processor controlled robotic arm is further configured to move the catheter/bronchoscope device, and control a computerized motor actuator system (such as previously discussed drive wheels 306, and motors "M) to guide at least the distal tool plate (109) of the distal end of the distal stage hollow catheter (108) to a target location. Here (308) shows the connectors and/or position encoders to control any of motors "M" as well as other motors to control the robotic arm's linear stages. As before, (309) shows the connectors and interfaces to operate and control other conduits, such as cameras controlling cameras, lights, sensors, position indicators, electrodes, tool tips, and the like.

Figure 22:
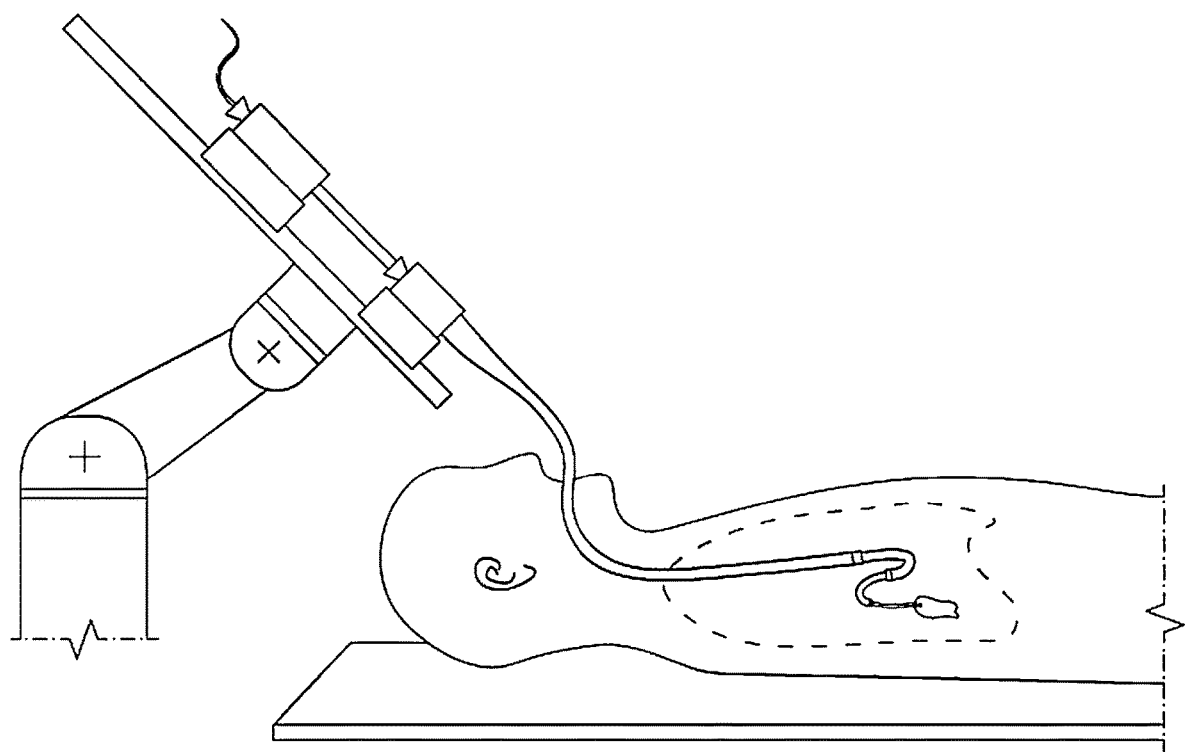
FIG. 22 shows an embodiment where the robotic system is applying the catheter to a patient.

FIG. 22 shows an embodiment where the robotic system is applying the catheter to a patient.

In some embodiments, the at least one control head is mounted on a processor controlled robotic arm. This processor controlled robotic arm is further configured to move the device and control the at least one computerized motor actuator. These are used to guide at least the distal tool plate of the distal end of the distal stage hollow catheter to a target location (inside the patient).

Figure 23A:
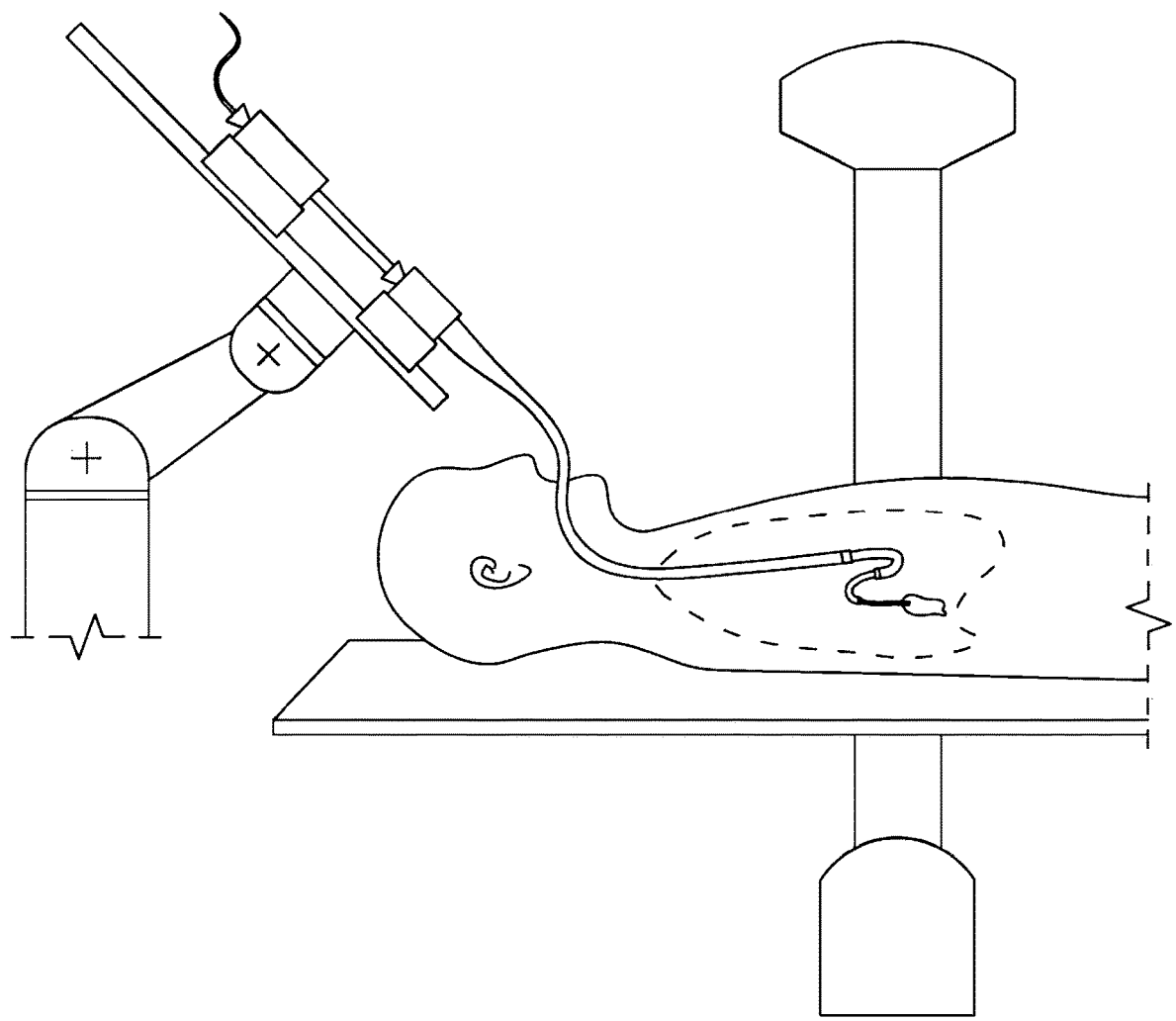
FIG. 23A shows an embodiment where the robotic system is applying the catheter to a patient, using a C-arm type imaging system to visualize progress.

FIG. 23A shows an embodiment where the robotic system is applying the catheter to a patient, here using a C-arm mounted radiologic imaging system to help visualize progress.

Figure 23B:
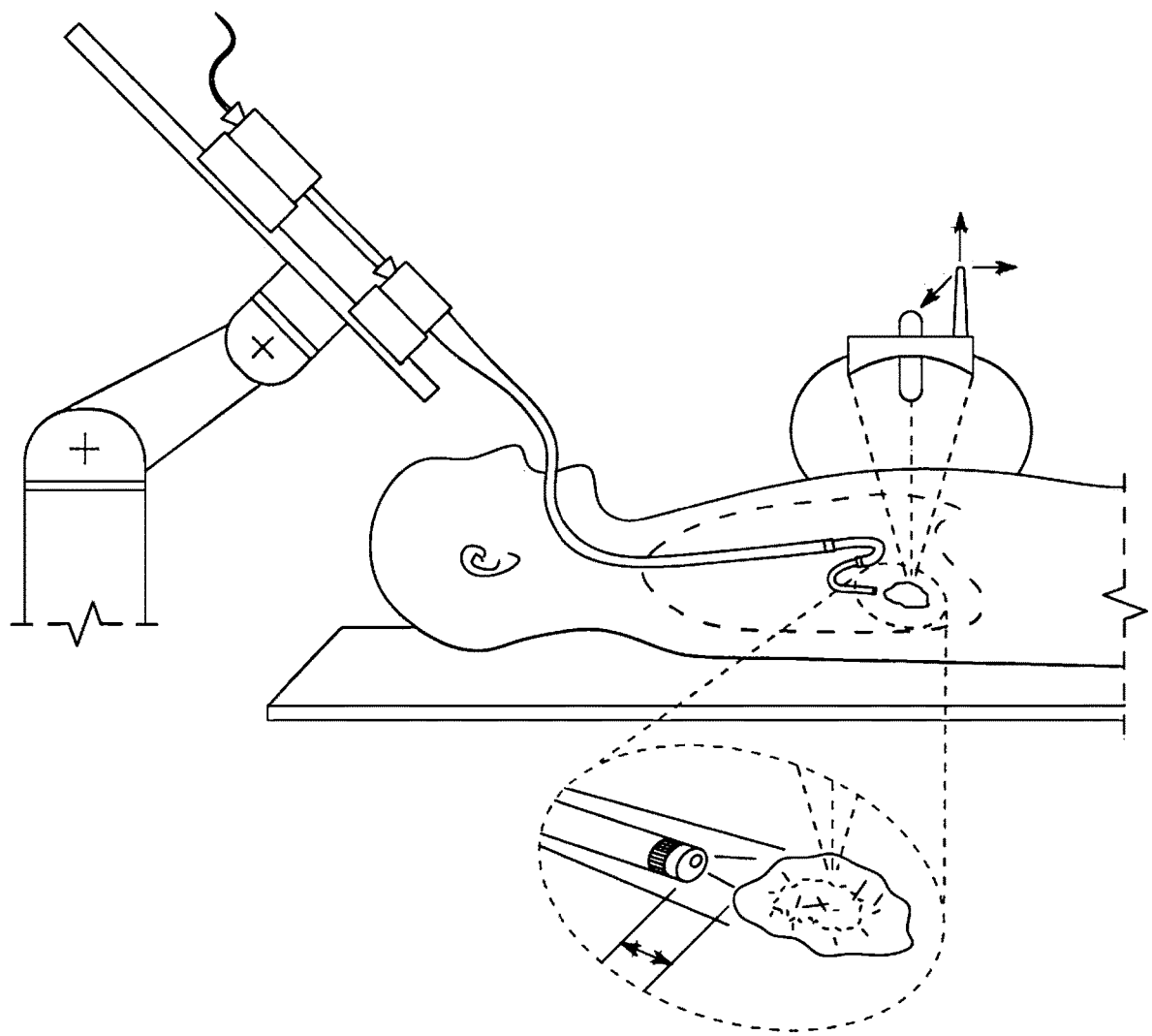
FIG. 23B shows an alternate embodiment where the robotic system is further configured to administer a payload comprising therapeutic energy, such as ultrasonic energy, to a target tissue.

FIG. 23B shows an alternate embodiment where the robotic system is also configured to deliver a payload comprising therapeutic energy, such as ultrasonic, infrared, or other type of energy to a target tissue. Here the device may be used for multiple purposes, such as directing the therapeutic energy, delivering agents to enhance the therapeutic impact of the therapeutic energy, or assess the results of the therapy.

Figure 23C:
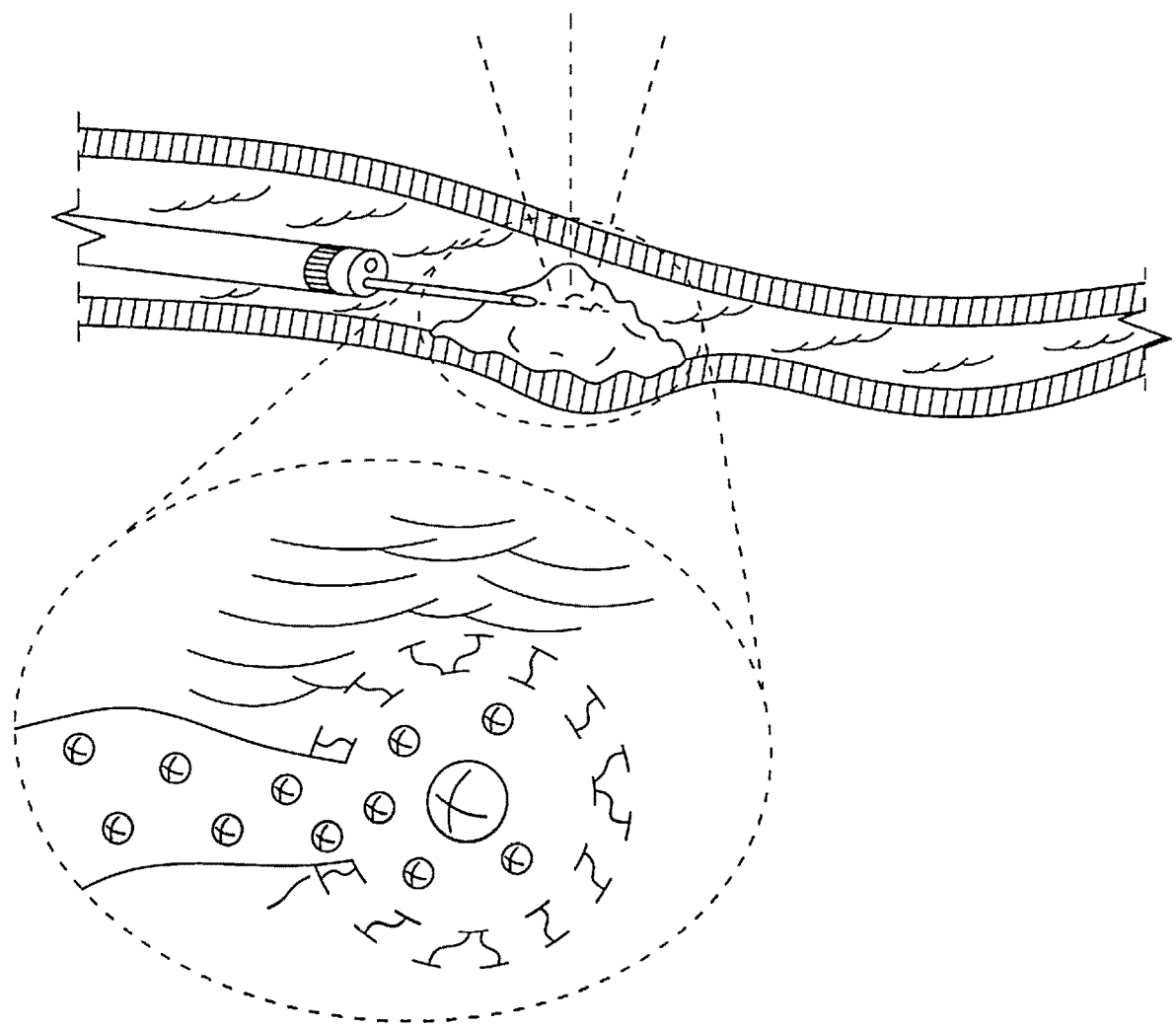
FIG. 23C shows an alternate embodiment where the robotic system is also configured to administer a payload comprising an imaging contrast agent or one or more therapeutic molecules to a target tissue.

FIG. 23C shows an alternate embodiment where the robotic system is also configured to administer a payload comprising an imaging contrast agent or one or more therapeutic molecules to a target.

The Distal Tool Head (Distal Plate)

Figure 24:
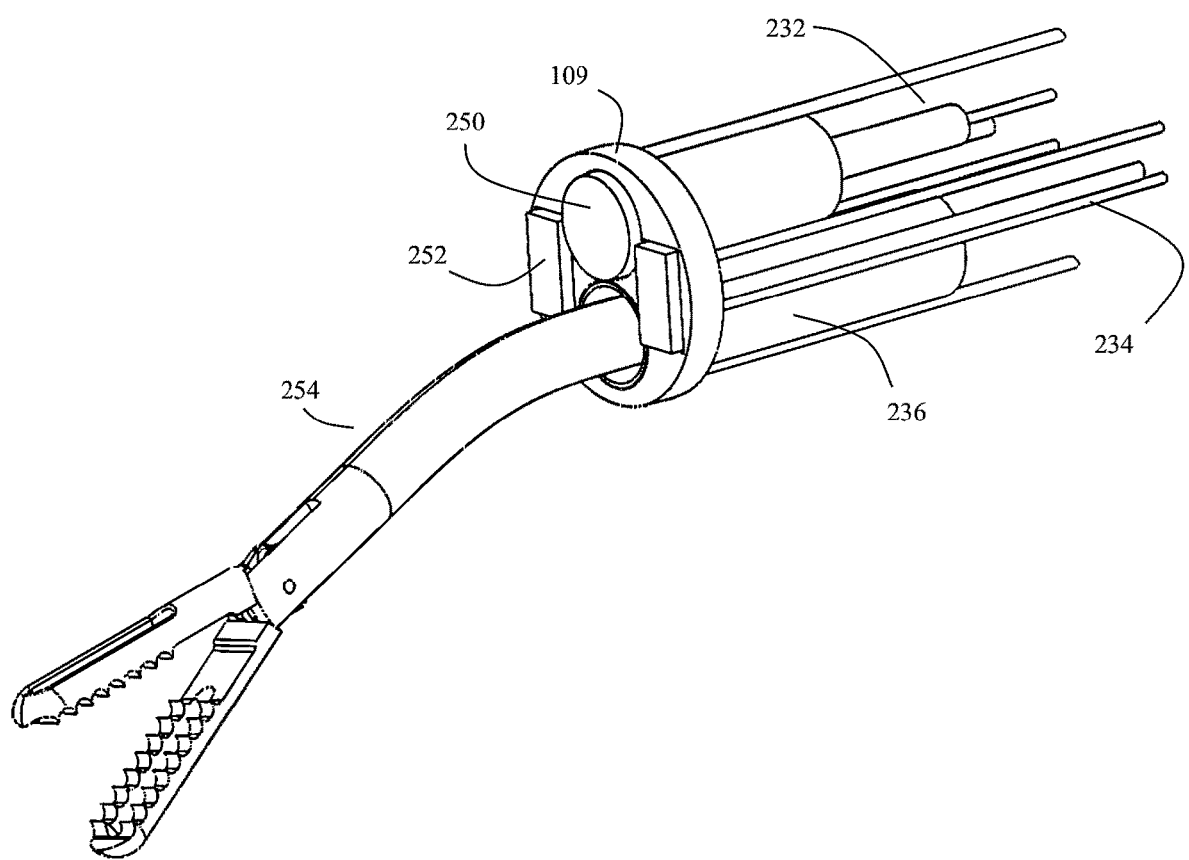
FIG. 24 shows the tool head with camera, lighting and forceps.

The distal stage (distal portion 108) often has a tool head (109) at its distal end. Although the examples so far have mostly just shown electrodes (110) as one type of tool, many alternative tools and configurations are also possible. As shown in FIG. 24, this tool head (109) may be alternatively, or additionally, fitted with other devices such as a camera, lighting and a tube or opening for delivering tools, e.g. forceps, brushes, biopsy needles, electrodes, drug delivery needles, and the like.

Although usually the distal tool plate will obscure at least some part of the distal opening of the distal stage hollow catheter (108), alternative embodiments are possible. In some embodiments, distal tool plate (109) may be configured with a distal tool plate opening diameter that is as large as an inner diameter of the distal stage hollow catheter (108). Note that this large-opening distal tool plate will still be configured to attach to the steering cables (220 . . . 226).

FIG. 24 shows the distal tool plate (aka tool head 109) with camera (250), lighting (252) (such as the two LED lights shown) and forceps. Here the outer wall of the distal portion (108) is not shown (or alternatively it has been made transparent) so that the various components and conduits (210-240) can be seen.

For example, camera (250) may be serviced by a first electrical conduit (232), LED (252) may be served by a second or third electrical conduit (234). The conduits may also include hollow tubes (236), from which various devices, such as forceps (254) may be routed and controlled.

Figure 25:
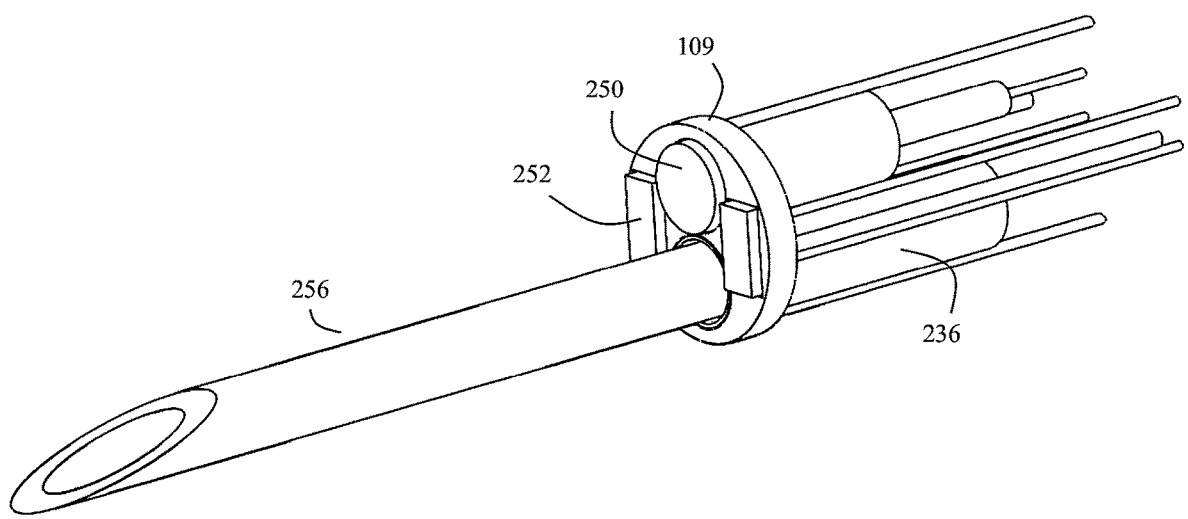
FIG. 25 shows the tool head with a biopsy needle.

FIG. 25 shows the tool head (109) with a biopsy needle (256).

Put alternatively, in some embodiments, at least some of the conduits (such as 236) and the distal tool plate (109) may be configured to obtain any of tissue biopsies from a target tissue, or to administer therapy to a target tissue.

Figure 26:
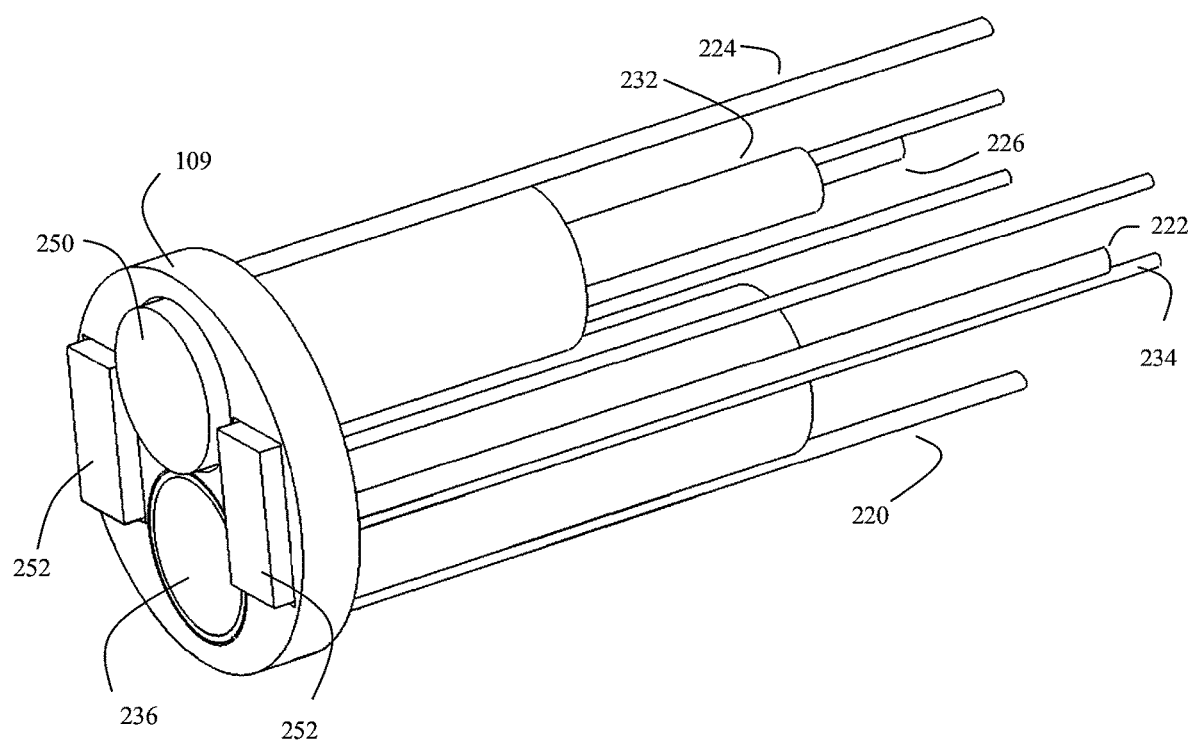
FIG. 26 shows some of the components that may be integrated into the tool head's tool plate.

FIG. 26 shows another view of some of the components and conduits that may be integrated into the tool head's tool plate (109). In here this includes a camera 250), a working channel (which can also be viewed as a hollow tube conduit (236) for delivering tools, and two LED lights (252). Coming off the tool plate (109) are the four previously discussed pull wires, conduits, or cables (220, 222, 224, and 226) for a 4-way distal stage articulation (e.g., X, Y, and Z axis movement, or 3D articulation). The conduit leads (232), (234) for the camera and LEDs are also shown. The camera (250) can be any type of small video camera, including a CMOS, CCD, or fiberscope. The LEDs (252) can be replaced by fiber optics lighting as desired, in which case some of the conduits (such as 234) may be optical fibers.

As previously discussed in FIGS. 22 to 23B, it will often be useful to use various types of location tracking or imaging devices to determine the location of the device, in particular the tool plate (109) and/or associated tools while in use. Thus, in some embodiments, any of the distal tool plate (109) or portions of the conduits may comprise any of optical or radiofrequency detectors or emitters or radio-opaque materials configured to enable a location of the distal tool plate or portions of the conduits to be determined.

As previously discussed, often the optical detector (250) may be a video camera, and the emitter (such as 252) may be configured to emit light for this video camera.

Figure 27:
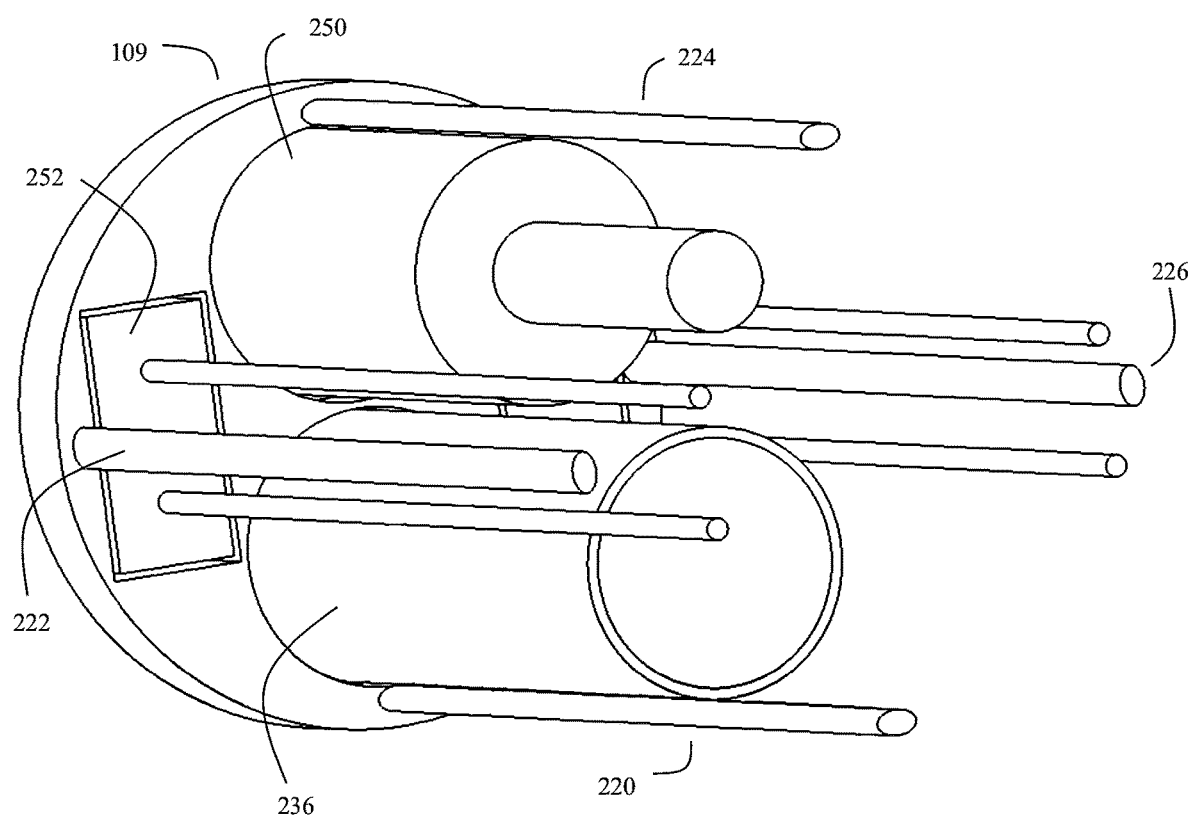
FIG. 27 shows the backside of one embodiment of the the tool head

FIG. 27 shows the backside of one embodiment of the the tool head (109). The pull wires (steering cables, conduits) in this case are for a 4-way, but they can be reduced down to 3, 2, or 1-way steering arrangement.

Distal Plate Features:

The distal plate, also called the distal tool plate (109) is a main structural component, often disk shaped, that is positioned on the distal end of the distal segment (108). The distal tool plate holds various types of conduits that send electrical or chemical signals to and from the distal end of the device and the operator or computer at the proximal end of the device. The distal tool plate can also provide access for tools to reach the area of treatment.

Figure 28:
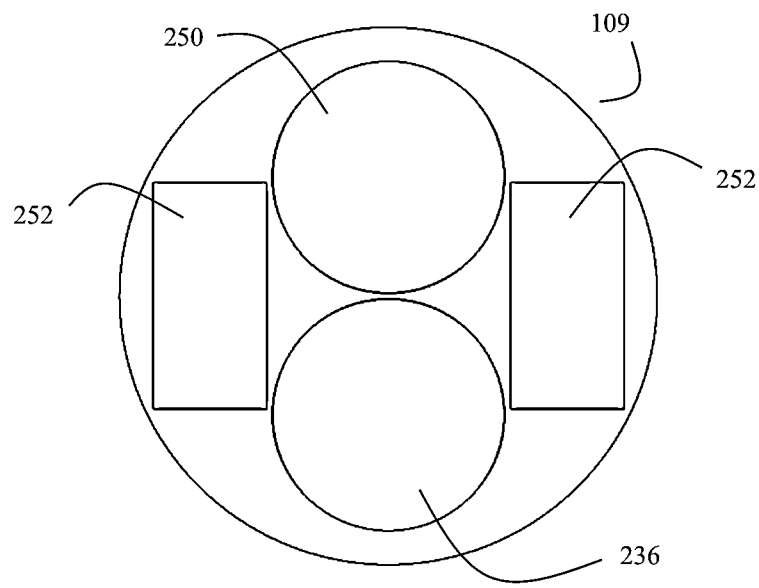
FIG. 28 shows an embodiment of the tool plate that locates and mounts a camera, two LEDs light and a tool port.

FIG. 28 shows an embodiment of the tool plate (109) that locates and mounts a video camera (250), two LEDs to provide light (252), and a hollow tube conduit (236) that can be used as a tool port.

Figure 29:
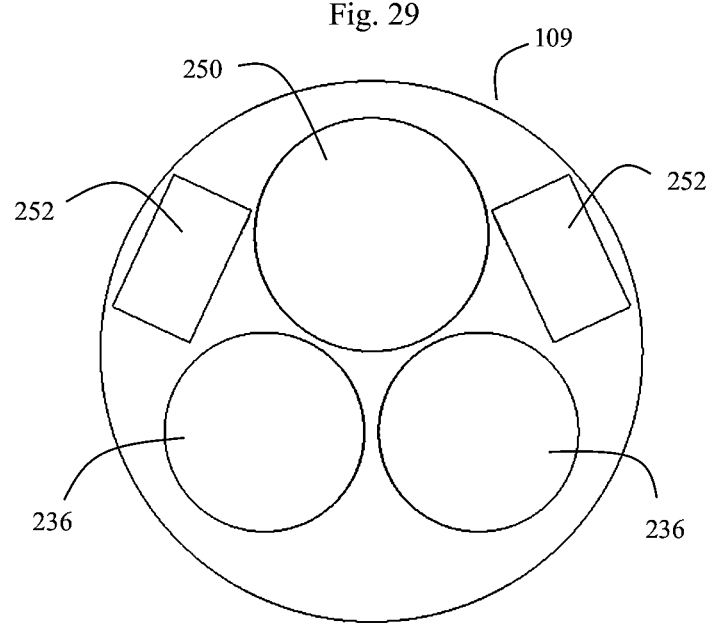
FIG. 29 shows the tool plate with two tool ports, camera and LEDs.

FIG. 29 shows the tool plate (109) with two hollow tube conduits (236) providing two tool ports, a camera (250) and two LEDs (252).

Figure 30:
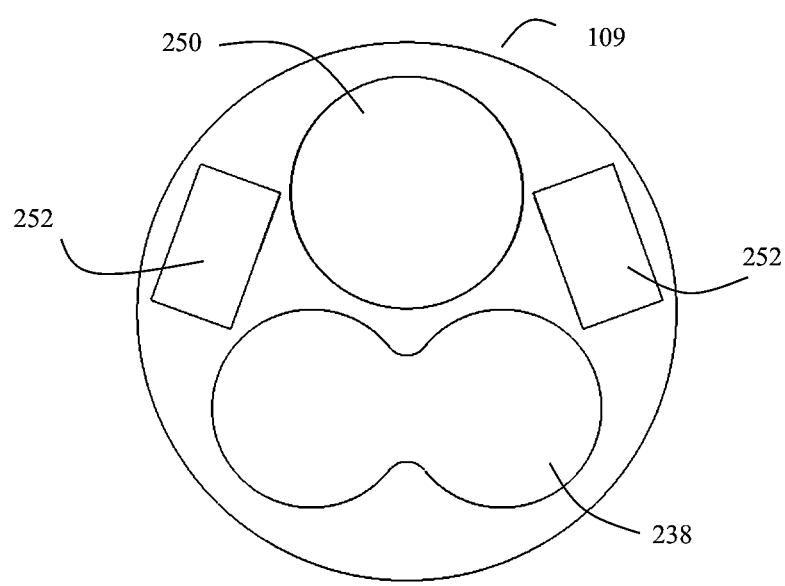
FIG. 30 shows the tool plate with a tool port with guide feature for bipolar electrodes or other tools plus camera and LEDs.

FIG. 30 shows the tool plate (109) with a tool port (238) providing another type of conduit that can provide a guide feature to introduce bipolar electrodes (such as (110*a* and 110*b*), or other tools, plus a camera (250) and LEDs (252).

Methods of Biopsy, and Delivering Therapy at the Tool Head

Figure 31A:
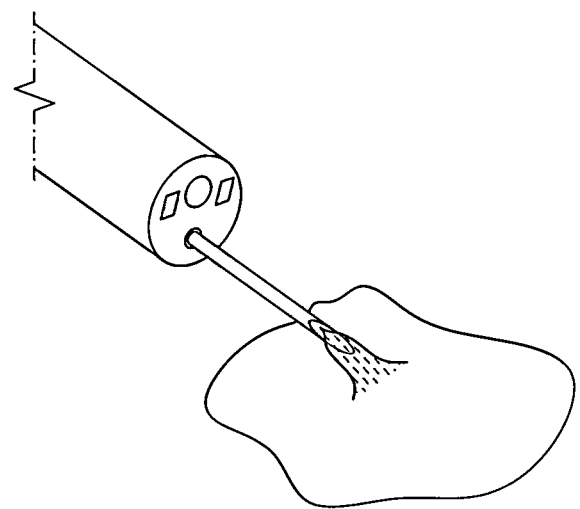
FIG. 31A and FIG. 31B shows that a needle can be used to retrieve a biopsy from a lesion location using the Articulating Rotary Robotic Bronchoscope.
Figure 31B:
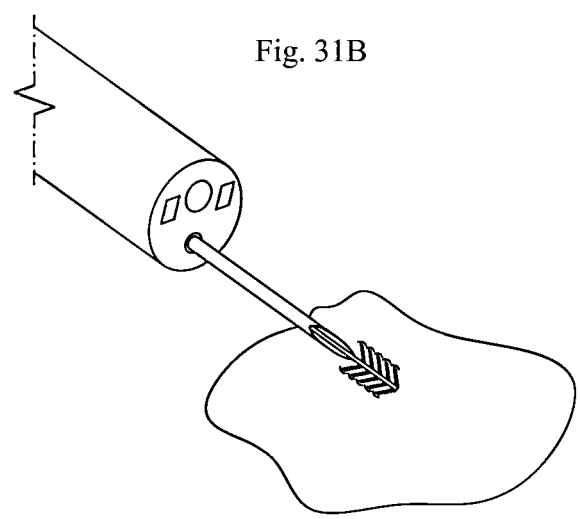

FIG. 31A and FIG. 31B shows how a needle can be used to retrieve a biopsy from a lesion location using the catheter device.

Figure 32:
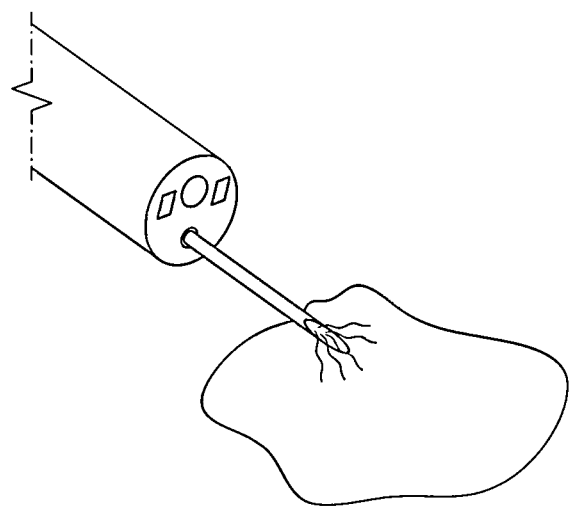
FIG. 32 shows an example of monopolar treatment methods, such as using the device to inject a drug into a cancerous tumor.

FIG. 32 shows an example of monopolar therapy methods (here defined as providing therapy using only one probe), such as using the device to inject a drug into a cancerous tumor.

Figure 33:
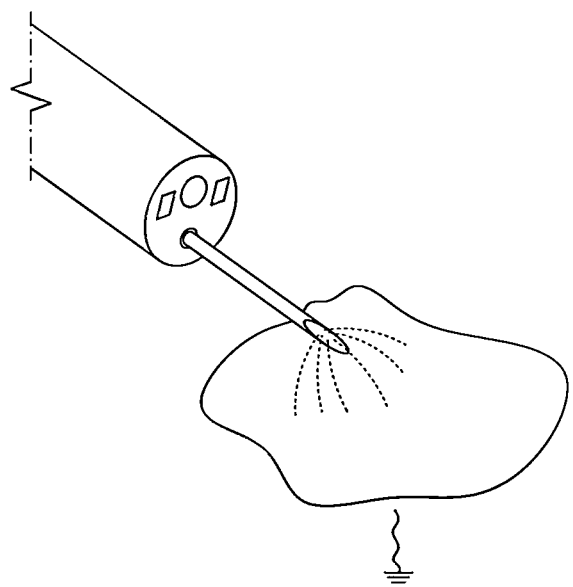
FIG. 33 shows another example of monopolar methods, here treating a cancerous tumor with radiofrequency (RF) mono-polar energy to either treat or activate a drug.

FIG. 33 shows another example of monopolar therapy methods, here treating a cancerous tumor with radiofrequency (RF) mono-polar energy from a single electrode to either treat the tumor directly, or activate a drug that in turn attacks the tumor.

Figure 34:
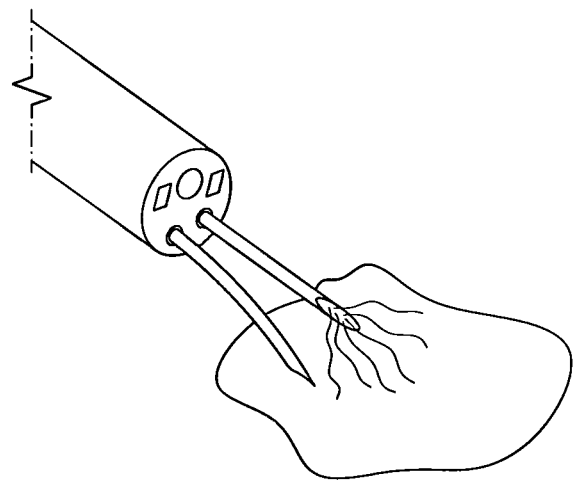
FIG. 34 shows an example of a Bi-polar method. Here a drug can be injected into a cancerous tumor. There is a return needle that is also injected into the tumor.

FIG. 34 shows an example of a bi-polar therapy method, here defined as providing therapy using two probes). Here a drug can be injected into a cancerous tumor using a first probe or needle. There is a return needle that is also injected into the tumor, which may either be used to deliver a second drug, more of the first drug, or return excess drug from the tumor.

Figure 35:
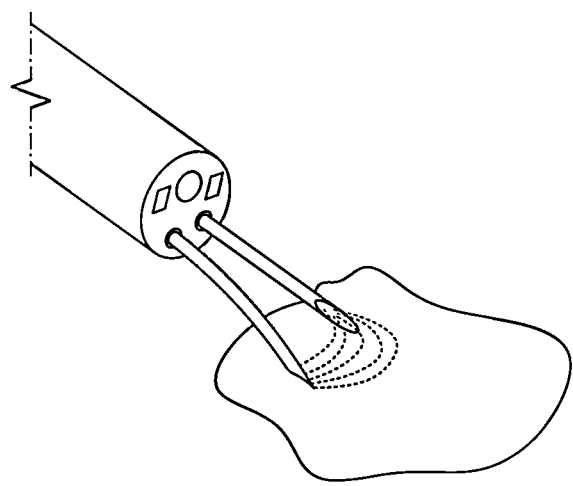
FIG. 35 shows another example of a Bi-polar method. Here the cancerous tumor can be treated with RF bi-polar energy to either treat or activate a drug.

FIG. 35 shows another example of a bi-polar therapy method. Here a cancerous tumor can be treated with RF (radiofrequency) energy between two electrodes to either treat the tumor directly, or activate a drug to in turn attack the tumor.

Figure 36:
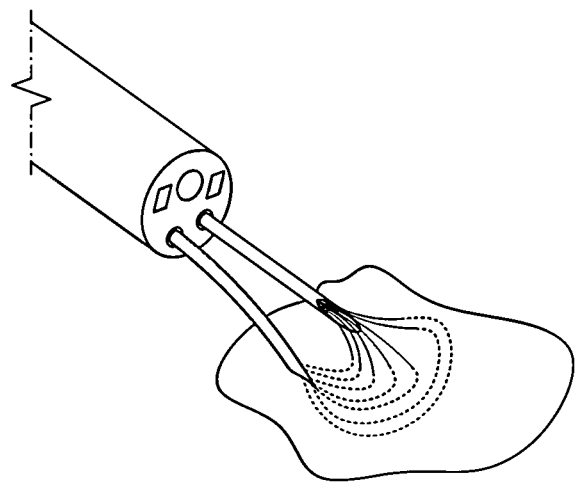
FIG. 36 shows an example of using bipolar RF energy to treat tumor by activating a payload comprising a therapeutic. In this case the plurality of needles are spread out in to the tumor

FIG. 36 shows an example of using bipolar RF energy to treat a tumor by activating a payload comprising a therapeutic. In this case two (or more) electrode needles are spread out into the tumor.

Figure 37:
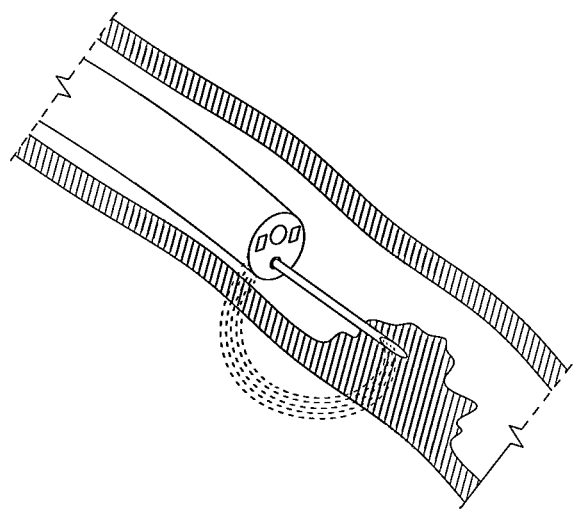
FIG. 37 shows that a tumor can be injected with a payload comprising a single needle and bi-polar RF energy can return through the body of the catheter where an electrode can be exposed at the front of the catheter.

FIG. 37 shows that a tumor can be injected with a single needle, and this same needle can act as a first electrode to deliver RF energy. Here, the head plate (109) or the body of the catheter (108) can act as a second electrode. Thus, with this arrangement, an electrode can be exposed at the front of the catheter, and bi-polar RF energy can return through the body of the catheter.

Drive Methods, Crawling

In some embodiments, the catheter can be made to crawl through tissue (see FIG. 1-3 as an example) with an undulating wave which can be set up between the distal (108) and proximal (106) flexing stages. This motion, along with the rotation of the distal stage (induced by hollow shaft 200) can produce a crawling or serpentine like movement. With the spinning distal stage while also flexing, the stage can drive further into a body lumen (such as a vessel or bronchi) towards the desired target. This is shown in FIG. 38A and FIG. 38B.

FIG. 38B shows an example of a robotic drive motion in schematic form that, usually in conjunction with one or more processors, drives the actuators/motors (often in a control head) to create this type of wave between the distal (108) and proximal stages (106). While this is happening, the hollow shaft (200) can also cause the distal stage (108) to rotate about the hollow rotatable coupler (107*b*) and transition housing (107*a*), causing the distal stage (108) to both rotate and thread itself into the bronchus or other body lumen.

1. In some embodiments, the two-stage robotic catheter can be made to crawl based on an algorithm that is driven by a known pre-operation 3D-map of the patient's pathway anatomy and the real-time position based on CT or MRI data.
2. In some embodiments, the algorithm can be configured to drive the previously discussed two-stage catheter where the proximal stage (106) is configured to bend (using proximal stage steering cables such as 210) and also to be pushed by a driving robot (see FIG. 21), and the distal (108) stage both bends (using distal stage steering cables such as 220) and rotates (due to hollow torque shaft 200, the rotatable coupler 107*b*, and the transition housing 107*a*) in the opposite direction of the proximal stage.
3. In some embodiments, the catheter device can be made to crawl by creating an undulating wave. This can be done by configuring the appropriate actuators to flex the distal (108) and proximal stages (106) out of phase with one another, thus producing a serpentine movement. In addition, as discussed above, the distal stage (108) can also be driven to rotate while flexing. With the distal stage rotating while at the same time flexing, the stage can drive further into the vessel, bronchi, or other body lumen.

Further Discussion

Any of the following instruments may pass through the device to a distal end effector at the device's distal end: cameras and lighting; needle biopsy devices; brush biopsy devices; forceps biopsy devices; debrider biopsy devices; RF coagulation/cutting devices (monopolar, bipolar); probes; sealing devices; and the like. Similarly, the joints and devices described herein may be used or adapted for use in any suitable medical or surgical procedure, including but not limited to: debrider tumor resection, shears tumor resection, delivery of biologics and medications, neural tumor resection, polyp resection or biopsy, breast biopsy, lung biopsy, minimal portal access heart bypass, endoscopic submucosal dissection, transurethral procedures (TURP, bladder tumors) prostatectomy, hysterectomy, stem cell delivery, delivery of arthroscopic tools, knees and hips, and transnasal procedures (frontal sinus tissue removal, functional endoscopic sinus surgery, etc.). These are only examples, however, and any other end effectors and procedures may be used in various alternative embodiments.

Further Discussion of Various Systems and Methods for Driving the Catheter

As will be discussed, in some embodiments, the invention may be a device, system, or method of actuator-assisted or robotically driving a multi-stage catheter device for traversing internal body passages. As previously discussed, this multi-stage catheter device will typically comprise a distal stage hollow catheter (108) and a different proximal stage hollow catheter (106). This distal stage hollow catheter will typically be a rotating distal stage hollow catheter with a distal stage axis. This distal stage hollow catheter is configured to rotate about a proximal stage axis of the different proximal stage hollow catheter. In this configuration, one end of the rotating distal stage hollow catheter is typically affixed to the end of the different proximal stage hollow catheter by a transition point coupler (107a, 107b).

This transition point coupler is configured to traverse an internal body passage. It typically comprises a transition housing (107a) that includes a hollow rotatable coupler (107b). This hollow rotatable coupler is usually configured as a rotary joint, and is configured to enable one end of the rotating distal stage hollow catheter to rotate about the end of the different proximal stage hollow catheter.

The catheter device will further comprise a hollow torque shaft (200) mounted inside the proximal stage hollow catheter (108). The hollow torque shaft is attached to the hollow rotatable coupler (107b). This hollow torque shaft is configured to convey torque to the rotatable coupler and the rotating distal stage hollow catheter (108).

The catheter device will further comprise at least one proximal stage steering cable (210). This cable is connected to the transition housing (107a). This at least one proximal stage steering cable is disposed inside the proximal stage hollow catheter (106), outside of the hollow torque shaft (200). The at least one proximal stage steering cable (210) is configured to convey proximal stage steering force to said transition housing (107a), causing the transition housing and the distal stage hollow catheter (108) to move (e.g. flex) according to the proximal stage steering force.

The hollow torque shaft (200), distal stage hollow catheter (108), hollow rotatable coupler (107b) and said transition housing (107a) typically further comprise a working channel (See FIG. 16, 228) configured to convey a plurality of conduits through the proximal stage hollow catheter and the distal stage hollow catheter to at least a distal tool plate (109) mounted on a distal end of the distal stage hollow catheter (108).

In a preferred embodiment, at least some of said conduits comprise at least one distal stage steering cable (220) that is connected to the distal tool plate (109) on the distal end of the distal stage hollow catheter. This at least one distal stage steering cable (220) is configured to convey distal stage steering force on the distal tool plate (109). This causes the distal tool plate and the distal stage catheter to further move (e.g. flex or unflex) according to the distal stage steering force.

In terms of a device, system, or method of driving the above catheter, expressing the invention in methods format, the invention will typically comprise flexing and unflexing the end of the distal stage hollow catheter. This can be done by using at least one distal stage tensioning actuator (for example, any of 350f1, 350af1), to create and release tension on at least one of the distal stage steering cables (220). This is typically one while also rotating the at least one distal stage steering cable in a 1:1 ratio with any rotation of at least the distal stage hollow catheter (108).

Figure 39:
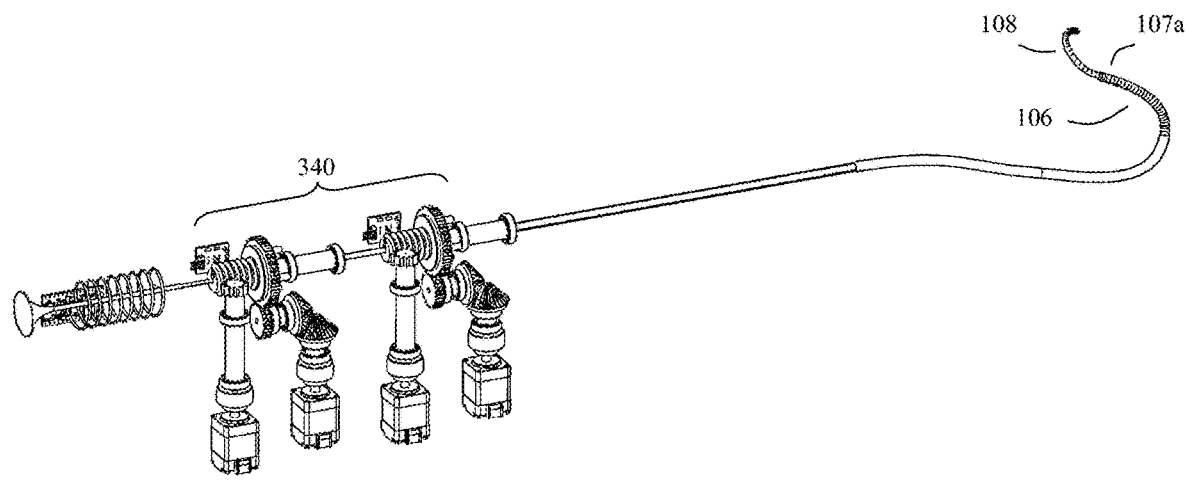
FIG. 39 shows how the multi-stage catheter device may be robotically driven.
Figure 40:
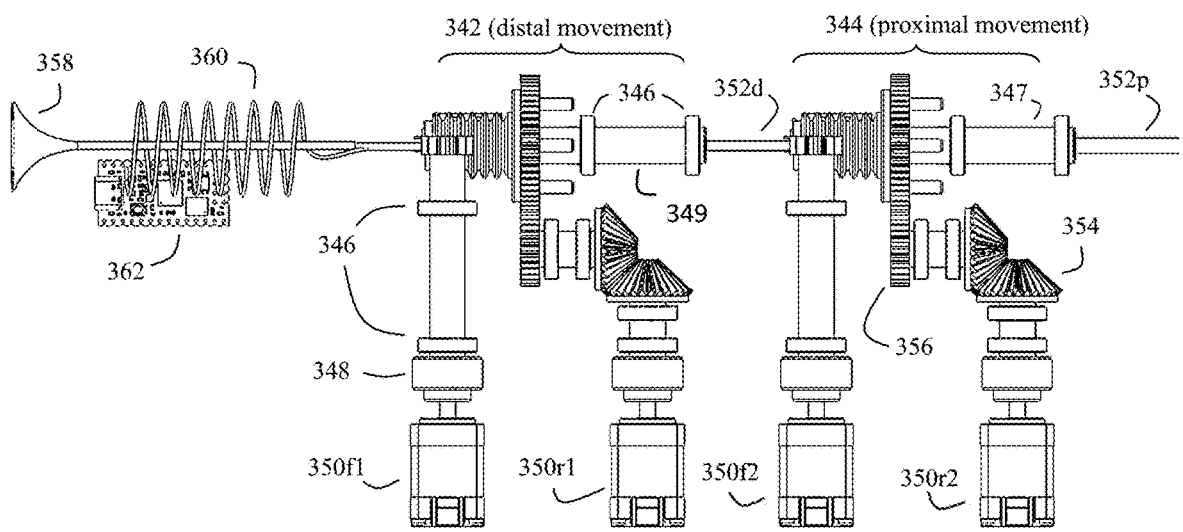
FIG. 40 shows further details showing how this robotic drive system can operate.

FIG. 39 and FIG. 40 show another example of how the previously described multi-stage (such as a proximal stage 106, transition point coupler (107a), and distal stage 108) catheter device can be driven. In this embodiment, the robotic system uses both rotary torque mechanisms and linear actuation mechanisms. These two types of mechanisms (340) are coupled together to produce both rotary motion and linear motion at the same time.

FIG. 39 shows how the multi-stage catheter device may be robotically driven.

In some embodiments, the invention may further comprise moving (flexing) the transition point coupler (107a, 107b) by using at least one proximal stage tensioning actuator (350r1) to create and release tension on at least one of said at least one proximal stage steering cables. Again, this is done while also rotating the at least one proximal stage steering cable (210) (often using 350r2) in a 1:1 ratio with any rotation of said proximal stage hollow catheter and said distal stage hollow catheter.

FIG. 40 shows further details showing how this robotic drive system (340) can operate. This includes the distal drive section (342) and the proximal drive section (344). Each drive section may further comprise bearings (346), distal and proximal drive body shafts (349, 347) optional motor drive couplers (348), and motors/actuators. In some embodiments, these motors/actuators are electromagnetic motors/actuators, often controlled by suitable processors and sensors.

These motors/actuators include "tensioning motors/actuators" (350f1, 350f2) and "rotate motors/actuators" (350r1, 350r2). Other components can include torque shafts (200), potentially the outside of the proximal portion of the catheter (106), miter gears (354), and other types of gear arrangements (356). Additional components may include an insertion funnel or lure lock device (358), optional electrical wire coils for camera or therapy devices (360), and other electronic components such as sensors and drive circuitry (362).

As will be discussed shortly, the "tensioning motors/actuators" (350f1, 350f2) are generally configured (often with suitable gear assemblies) to "flex" or "bend" or "steer" a given stage of the multi-stage catheter, usually by controlling tension on a suitable steering cable. By contrast, the "rotate motors/actuators (350r1, 350r2) are generally configured (again with suitable gear assemblies) to rotate that particular steering cable, usually in conjunction with other rotations of the multi-stage catheter device, to prevent the various cables from tangling with each as portions of the catheter device rotate (as required to traverse various body passages).

Definition: These mechanisms convert the force between various processor-controlled electromagnetic actuators into a desired mechanical movement are here generally defined as "contacting mechanisms" Here, a "gear assembly" can be a specific type of contacting mechanisms, but other contacting mechanisms that don't use gears will also be taught.

In some embodiments, the invention may also comprise using at least one distal stage tensioning actuator (350f1) and at least one proximal stage tensioning actuator (350f2), as well as at least one contacting mechanism. These actuators often comprise at least one processor-controlled (410) electromagnetic actuator. To assist in precise movement, often at least a motion or position sensor (e.g. 412, 376a, 376b) may be analyzed by this least one processor during this process to control one or more actuators. In some embodiments, the actuator(s) may have built-in motion or position sensing ability, in which case the sensor(s) may further comprise such built-in sensors as well.

Figure 41:
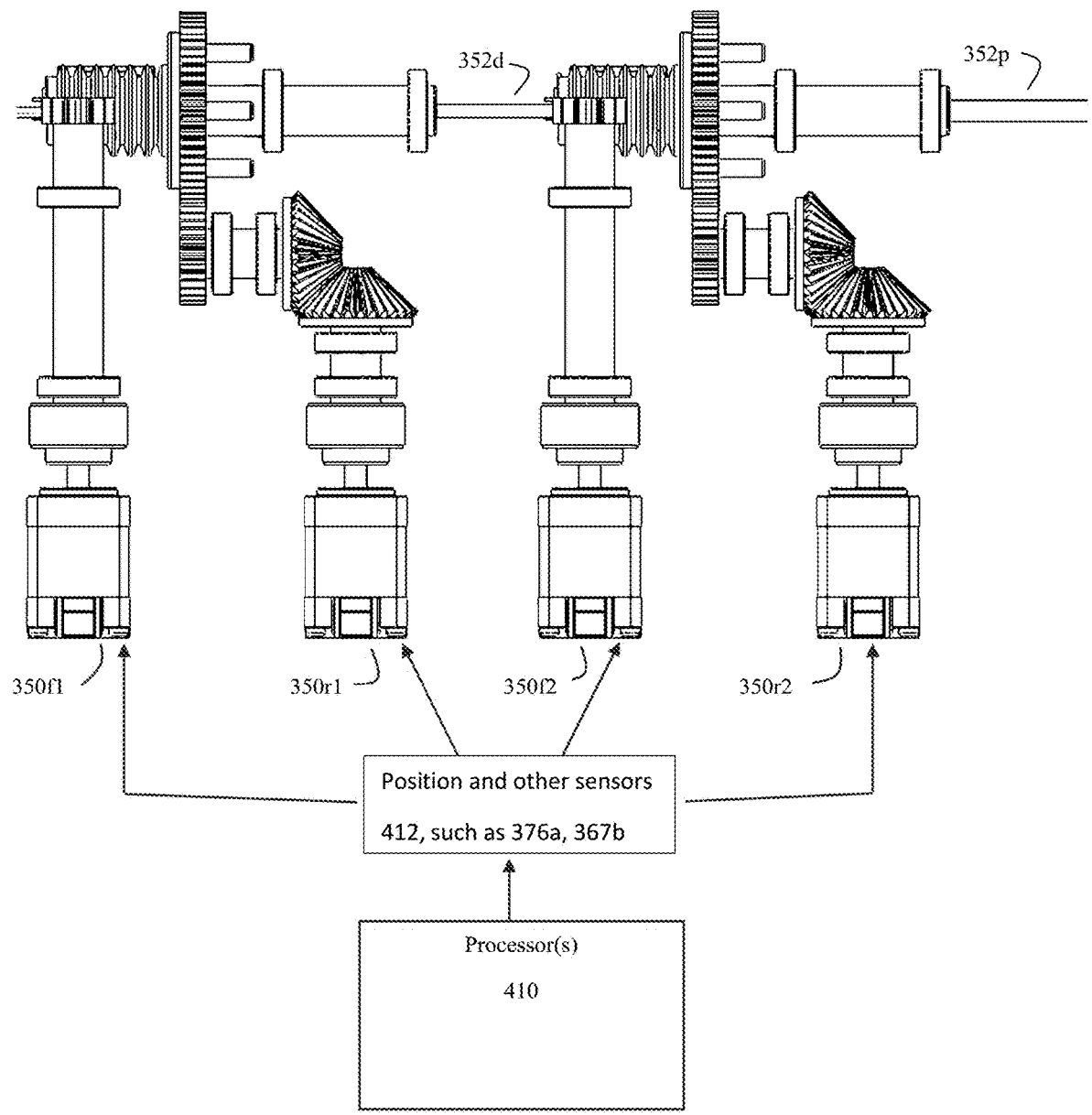
FIG. 41 shows more details of how the mechanical drive system can operate to rotate various sections of the multi-stage catheter device.

As shown in more detail in FIG. 41, the Axis of Rotation (352d, 352p) for all catheter stages is defined at the motor drive axis where the mechanical drive system rotates at least one or more catheter stages.

FIG. 41 shows more details of how the mechanical drive system can operate to rotate various sections of the multi-stage catheter device.

As previously discussed, in a typical embodiment, at least some, and often all, of the various actuators (such as 350f1, 350r1, 350f2, 350r2) will be electromechanical actuators. These will typically be driven under processor control by one or more processors (usually one or more microprocessors (410). The microprocessors, in turn, will usually receive input from one or more sensors (412), such as the various sensors (376a, 376b), which will be discussed shortly.

Although electromagnetic actuators are often given as a specific example, other types of actuators, such as electroactive nitinol and polymers, air-driven actuators (pneumatic actuators) or fluid drive actuators are not disclaimed.

Figure 42:
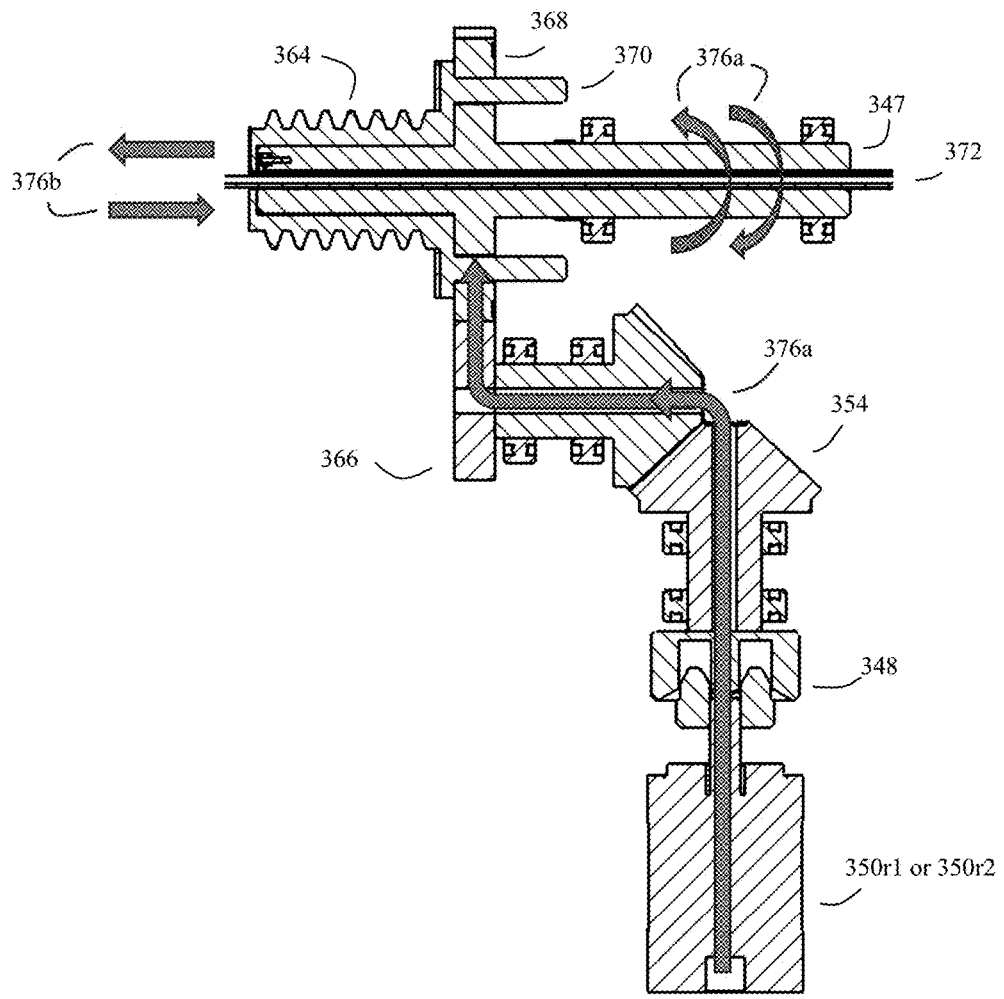
FIG. 42 shows a cross-section of the device previously shown in FIG. 41.
Figure 43:
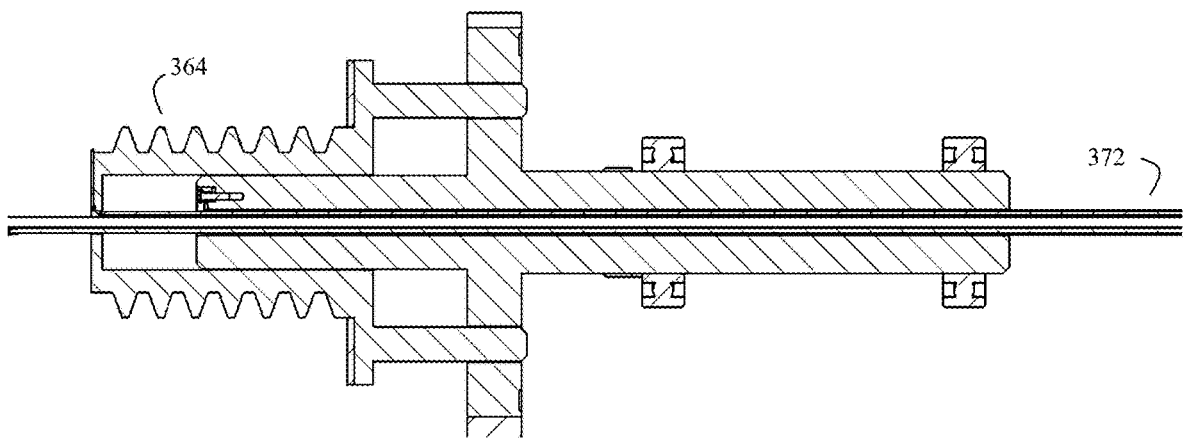
FIG. 43 shows a close-up cross-section of the drive rack, transfer gear, rotary drive gear and sliding drive pins portions of the device previously shown in FIGS. 41 and 42.

FIG. 42 and FIG. 43 show how the Distal or Proximal Linear Circular Gear Rack (364) slides along the Drive Body Shaft. These figures also show how the Distal or Proximal Circular Gear Rack is driven by the Distal or Proximal Rotary Drive Gear which is solidly connected to the Drive Body Shaft, which in turn is adhered to the Distal or Proximal Torque Shaft of the catheters. In this embodiment, the Linear Circular Gear Rack slides along the Drive Body Shaft while coupled to drive pins sliding through the Distal or Proximal Rotary Drive Gear. This coupling keeps the Flex Cable from becoming twisted while being actuated by the Linear Circular Gear Rack while rotating 1:1 with the Drive Body Shaft. There are many other ways to slidably mate the Linear Circular Gear Rack to the Drive Body Shaft for transferring torque such as keyway devices, flats (single, double . . . hex, etc.), pins, splines, or other mechanisms. The slidable mate (e.g., pins 370 or another mechanism) allows transverse movement along the rotating member or catheter axis while constraining movement radially from the rotating member or catheter axis.

FIG. 42 shows a cross-section of the device previously shown in FIG. 41. This shows a linear circular drive rack (364), transfer gear (366), rotary drive gear (368), optional sliding drive pins (370) and a suitable steering cable (372), such as the proximal stage steering cable (210) or distal stage steering cable (220) previously discussed. Note that, as shown in FIG. 40, there are usually at least two versions of this device, one (344) configured to operate the proximal section of the catheter, and another (342) configured to operate the distal portion of the catheter. Otherwise, as can be seen in FIG. 41, the two portions are relatively similar. The large arrows show the various directions of motion of the respective components during operation. As can be seen, the device both rotates (376a) about its axis (along 372), and also can be commanded to have an axial in and out motion as well (376b). The power transmission path from the actuator (350r1 or 350r2), through various optional intermediary gears such as (354) and (366), to the rotary drive gear (368) is shown as (376c).

Again, the "in and out" motion (376b) is used to apply or release tension to a given steering cable (such as 210, 220) that is used to flex or unflex or "steer" various stages of the multi-stage catheter. The rotary motion is designed to prevent the steering cables from getting tangled while, for example, various portions of the catheter are rotated to traverse various body lumens, such as by using the previously discussed hollow torque shaft (200).

Put alternatively, in some embodiments, the rotary drive gear (368) rotates the drive body shaft (349, 347), which in turn may be connected (depending on this is driving the proximal segment or the distal segment of the catheter) to either the distal torque shaft (e.g. 349 to 200), or the outer proximal tube body (e.g. 347 to 106).

In some embodiments, both the distal and proximal linear circular gear racks (364) (distal 342, proximal 344) rotate while also coupling their rotation to the sliding drive pins (370). These gear racks are driven to rotate 1:1 by their respective rotary drive gears (368). While any given linear circular gear rack (364) (distal 342, proximal 344) is rotating, it can be actuated for "in and out motion" or "tensioning motion" (376b) along the axial direction (372) by a linear circular pinion gear, (see FIG. 44, 374), which is allowed to slide in the grooves cut in (364) while (364) is rotating and be driving by sliding drive pins (370) on the appropriate drive body shaft.

In this embodiment, rotary motion is directed from the motor/actuator (350r1 or 350r2) through a contacting mechanism comprising a motor coupler (348) to miter gears (354), then to the transfer gear (366), and finally to the rotary drive gear (368). In some embodiments, one or more contacting gears such as these may also be termed a "gear assembly."

Note that in some embodiments, the proximal outer tube body (106) may be glued, mounted, or otherwise adhered to its respective (proximal 344) drive body shaft (347). In this embodiment, the proximal drive body shaft (347) may be used to directly to turn the proximal outer tube body (106). This controls the rotation of the transition point housing (107a). Here, steering cables (210) cause the proximal outer tube body (106) to flex or curve at any rotation of (347). In some embodiments, the distal version (342) of this drive body shaft (349) may be used to control torque on the torque shaft (200). This torque shaft, in turn, controls the rotation of the rotatable coupler/rotary joint (107b) and the distal portion of the catheter (108). Steering cables (220) can cause the distal portion of the catheter (108) to flex or curve in any rotational position. Catheter (108) and (106) can rotate or flex at any angle of rotation relative to respective drive body shafts (349) and (347).

FIG. 43 shows a close-up cross-section of the drive rack (364), transfer gear (366), rotary drive gear (368), and sliding drive pins (370) portions of the device previously shown in FIGS. 41 and 42. This shows more details of how this device accomplishes both rotation and in-and-out steering cable sliding motion. Here the linear circular gear rack (or drive rack) (364) is shown fully extended. The drive rack (364) has pulled the steering cable (220, 210) to a fully flexed state in this configuration.

Figure 44:
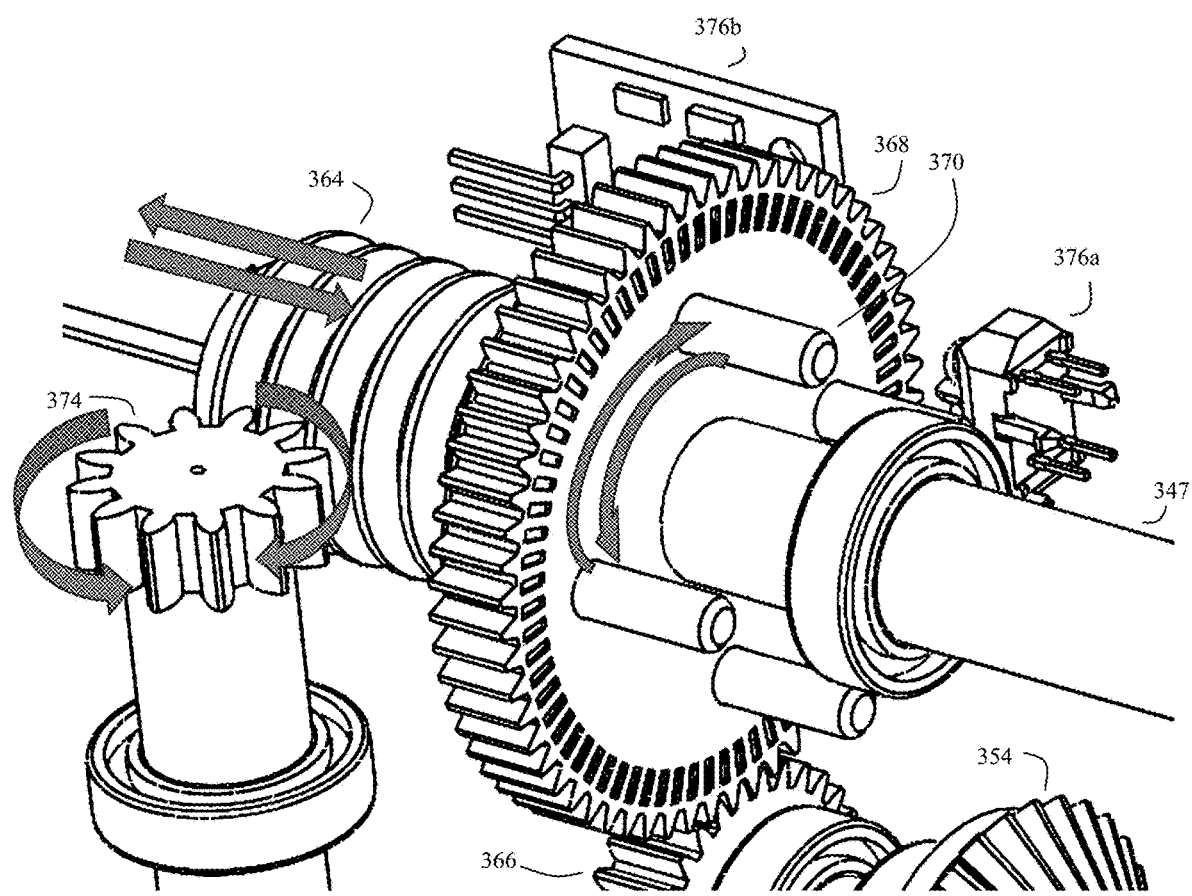
FIG. 44 shows a close-up view of the drive rack, transfer gear, and rotary gear system, as well as an example of how various sensors may be used to control and monitor the position of the drive.

FIG. 44 shows an alternative view showing a non-cross-sectional view of this portion of the system. Optional sensors (376a) and sensor electronics (376b) are also shown.

FIG. 44 shows a close-up view of the drive rack, transfer gear, and rotary gear system, as well as an example of how various sensors (376a, 376b) may be used to control and monitor the position of the drive.

Figure 45:
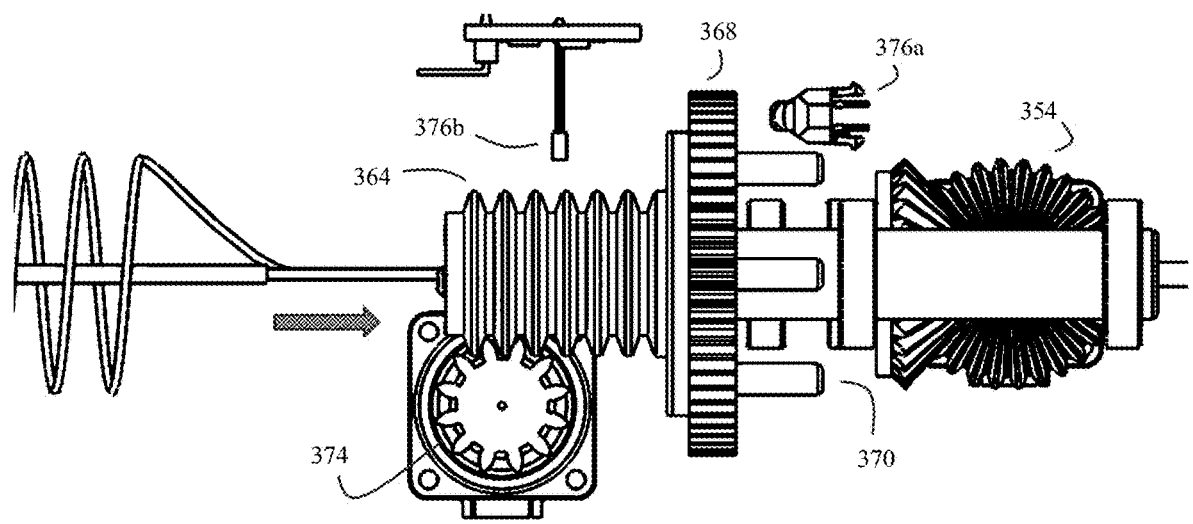
FIG. 45 shows one extreme position of the device's linear circular gear rack.
Figure 46:
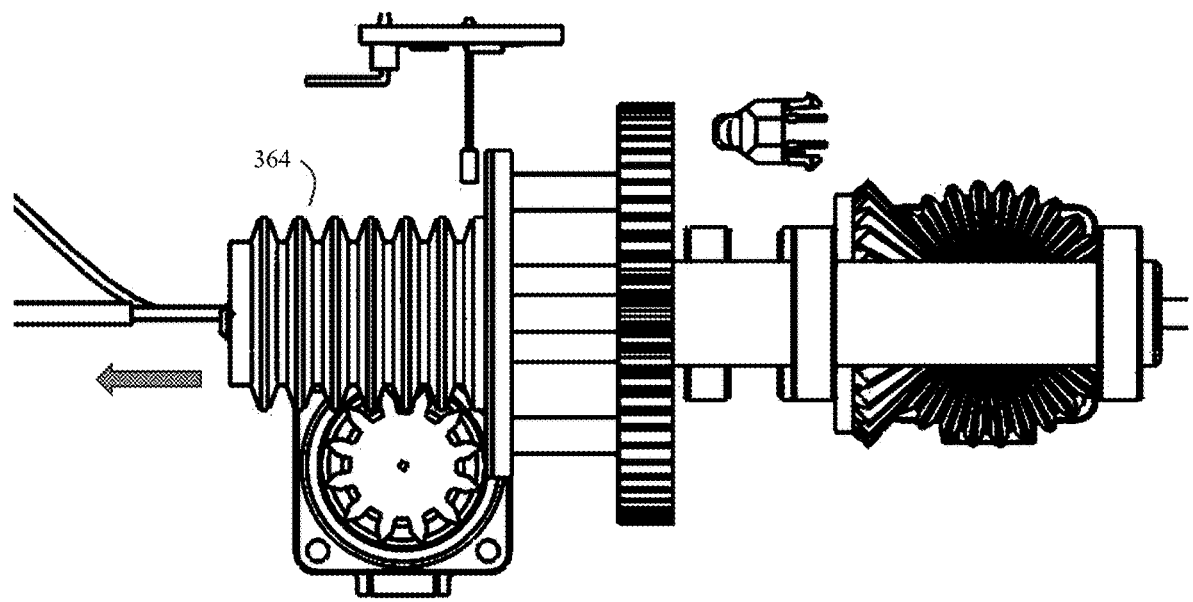
FIG. 46 shows a different extreme position of the device's linear circular gear rack.

FIG. 45 and FIG. 46 show how the rotary position for the Distal or Proximal Rotary Drive Gear may be tracked with sensors such as optical emitter/detector pairs and edge markings on the face of the gear. The closed loop linear position of the Distal or Proximal Linear Circular Gear Rack may be sensed by hall-effect sensors or other optical emitter/detector pairs in conjunction with a magnetic or reflective surface. Other types of sensors may also be used.

FIG. 45 and FIG. 46 show the extreme positions of the Linear Circular Gear Rack (364) for a single stage (e.g. any of 342 or 344). It is important to understand this rotary-linear drive in a simplified one-stage/one-catheter situation where the linear actuation rotates directly or 1:1 with the rotary stage. This rotation can go beyond 360 degrees in either direction without limitation and without the linear actuation mechanism causing the pull cables to become twisted. This is an important point, because a key objective of the invention is to prevent cable twisting, which can interfere with the function of the catheter device.

FIG. 45 shows the relaxed position where there is no cable tension. FIG. 46 shows the full flexed state where the cable is fully tensioned by the Linear Pinion Gear (374) engaging and driving the Linear Circular Gear Rack (364) with the output flexing the catheter. This can then return again to the relaxed state previously shown in FIG. 45.

FIG. 45 shows one extreme position of the device's linear circular gear rack (374) (for a single stage such as any of 342 or 344). Here, the linear circular pinion gear (374) has rotated clockwise and, by engaging with a ridge or ridges formed in the drive rack (364), has pushed the drive rack (364) and pins 370 to one furthest extent up against the rotary drive gear (368), thus releasing tension on one of the distal or proximal stage steering cables.

FIG. 46 shows a different extreme position of the device's linear circular gear rack (for the same stage as above). Here the linear, circular pinion gear (374) has rotated counter-clockwise and, again by engaging with a ridge or ridges formed in the drive rack (364), has pulled the drive rack (364) and pins 370 to the other furthest extent, thus creating tension on one of the distal or proximal stage steering cables. Here, the system's one or more sensors (378a, 378b) and processors (410) can again be used to adjust this tension to a desired extent.

Figure 47A:
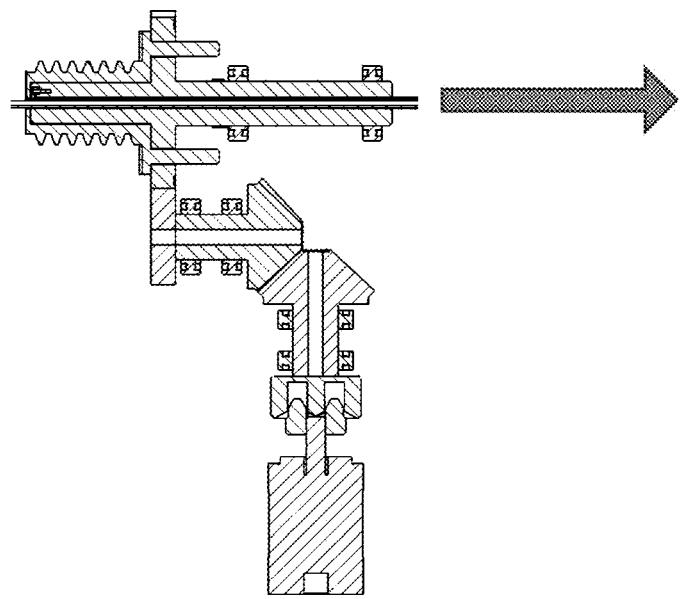
FIG. 47A shows a cross-sectional view of the rotary and linear drive system.
Figure 47B:
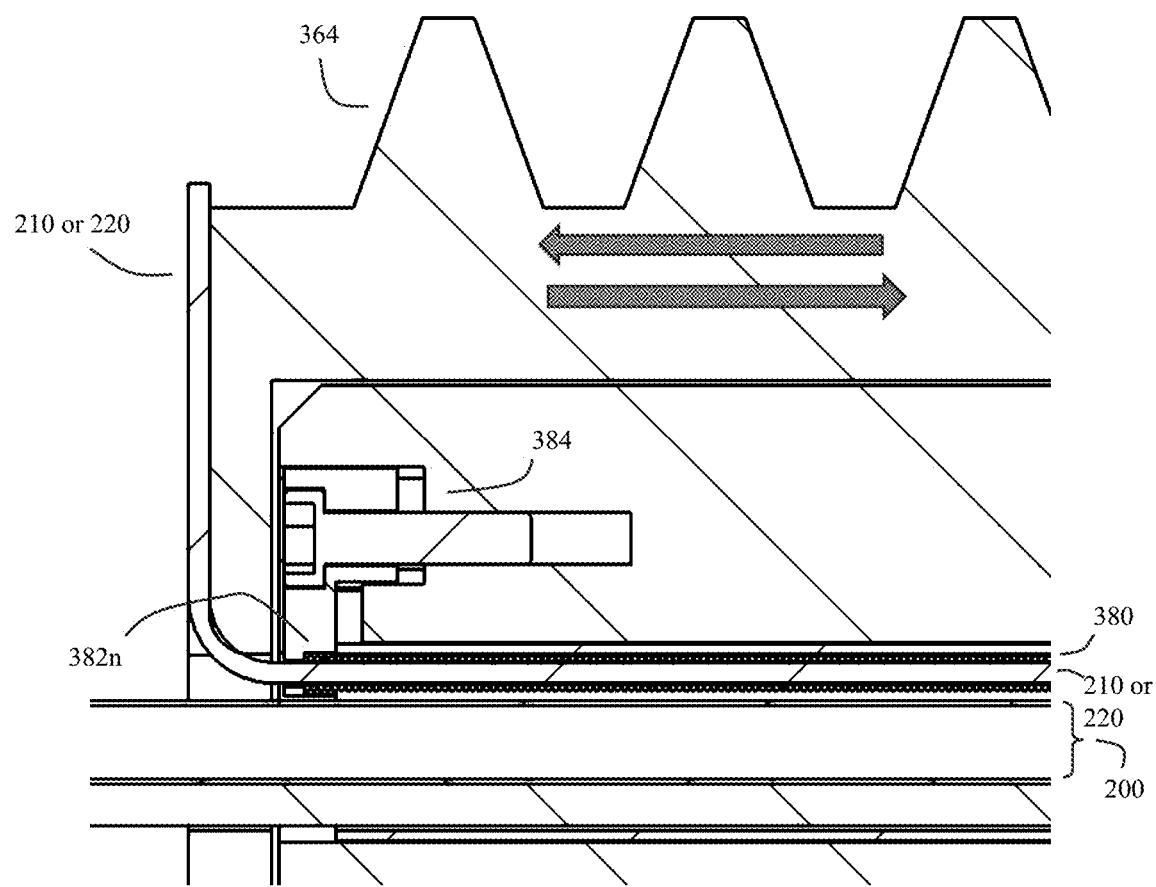
FIG. 47B shows further details of the drive rack previously shown in FIG. 47A.

FIG. 47A shows a cross-section of the rotary and linear drive system. FIG. 47B expands on a portion of FIG. 47A, and shows the position of the drive rack (364) and how the steering cable (220 or 210) is positioned as a result of movement of the linear circular pinion gear (374). This figure also shows a tightly wound isolation coil (380) that generally surrounds (and shields) nearly all its respective steering cable (220 or 210). This isolation coil (380) is often configured so that it has some extra length between the two isolation-coil-stops, such as (382n) and (386d). This means that the isolation coil has an uncompressed length that is a bit greater than the neutral axis of the catheter that it resides inside of. This isolation coil helps isolates the steering cable (210 or 220) tension such that the tension of the steering cable (flex cable) does not create tension force along the entire length of the catheter. Instead, due to the shielding or force-isolation property of the isolation coil, the tension force in the steering cable (210 or 220) is directed to only the flexible section that this steering cable is designed to flex or curve substantially.

The underlying idea is similar to the principle used on cable-operated hand brakes on bicycles and motorcycles. Mechanically, each isolation coil works by applying an equal but opposite force to its internal steering cable (210), (220), so that until the steering cable force reaches its destination at the far distal end isolation stop (386d) where it protrudes beyond the isolation stop. The cable force is isolated and directed on the section catheter beyond (386d) causing the catheter to flex from the point of where the cable is attached (tooling plate, transition housing, or near far distal edge of catheter tubing) to the isolation stop (386d).

Note that in FIG. 47A and FIG. 47B, the Linear Circular Gear Rack is not actuated, and the end of the catheter system controlled by that particular steering cable is in a relaxed state (large gray arrow straight).

FIG. 47A shows a cross-sectional view of the rotary and linear drive system. Here the drive system is in a first, "relaxed" state, similar to that shown in FIG. 45. In this configuration, there is lower tension on the distal (or proximal) steering cable, such as (220) or (210), and as a result, the relevant distal (108) or proximal (106) portion of the catheter tends to be straight (not flexed).

FIG. 47B shows further details of the drive rack (364) previously shown in FIG. 47A. Note that depending on which drive section (distal 342 or proximal 344) is involved, then often the proximal portion of the distal steering cable (220) or proximal steering cable (210) is affixed to the end of the dive rack. To help prevent mechanical cross-talk between the steering cables and other parts of the apparatus, either the steering cable may optionally pass through or traverse an isolation coil (380). This isolation coil is hollow, and the interior has sufficient diameter so that the steering cable can pass through this hollow interior freely. At the same time, the isolation coil helps to shield or "isolate" the movement of the steering cable (210 or 220) from the rest of the catheter device, at least while the steering cable (210 or 220) is inside the isolation coil. This isolation coil generally runs the entire length of the catheter up to a short distance before its particular steering cable reaches its destination (usually at or near the transition point coupler 107a or distal tool plate 109 depending on the type of steering cable).

Figure 53A:
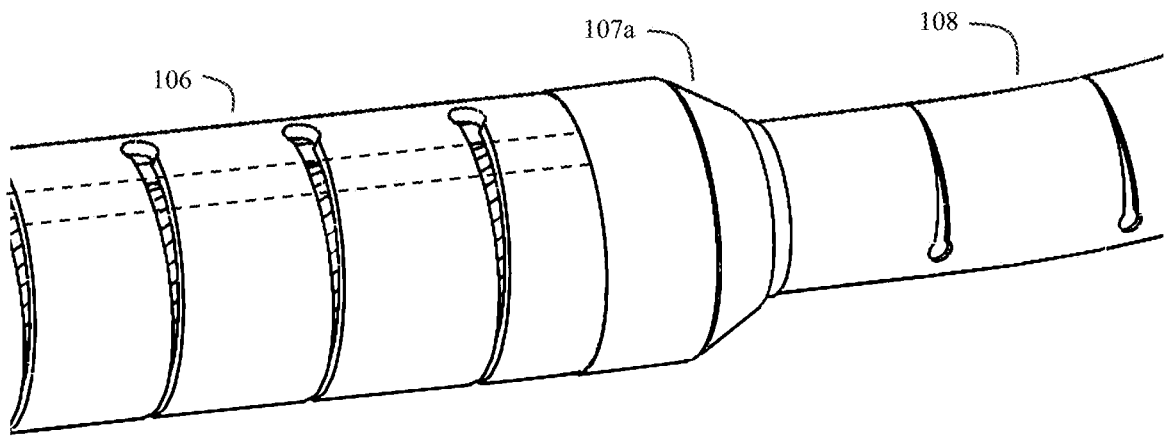
FIG. 53A shows an exterior portion of the multi-stage catheter near the transition housing between the proximal and distal stages.
Figure 53B:
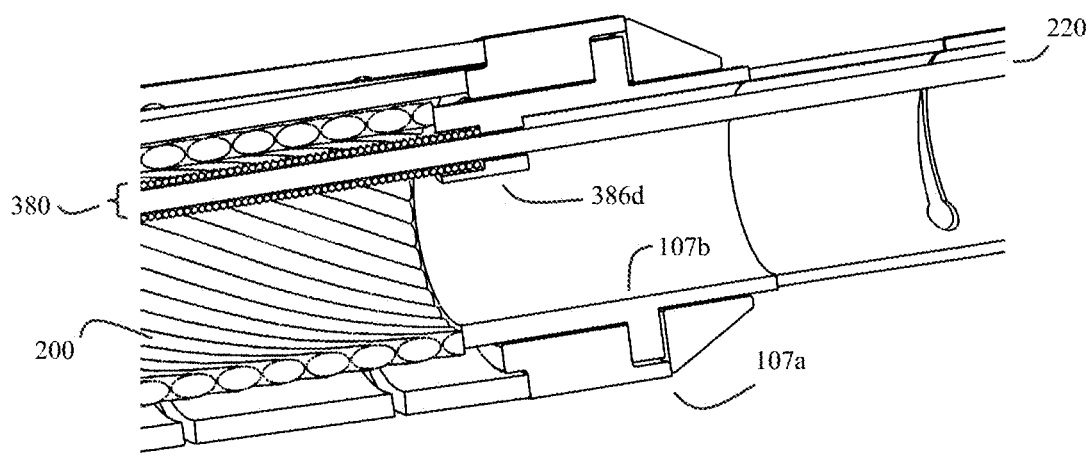
FIG. 53B shows a cross-section of the region shown in FIG. 53A, showing a detail of a distal stage steering cable and isolation coil.

The isolation coil has a near end (382n) and a far end (see FIG. 53B, 386d). The near (e.g. proximal) portion of the steering cable is attached (for example, clamped) to the flexing actuator (here the end of 364). The near end of the isolation cable (382n) is also attached in a manner that allows the steering cable to movably protrude past the near isolation coil end (382n), while blocking axial movement of the isolation coil this end. This isolation coil attachment can be done by various methods, such as by an adjustable isolation coil stop screw (384) which can also be used for setting the isolation coil compression. This compression setting can be a very fine adjustment for an isolation coil is tightly wound.

In FIG. 47B, a detail of the distal drive section (342) is shown, and thus, a portion of the hollow torque shaft (200) is also shown. If a proximal driver section (344) was shown, this torque shaft (200) might either be another type of torque shaft, such as a proximal torque shaft, or the exterior of the proximal catheter (106).

In some embodiments, according to the invention, at least one torque shaft actuator, such as (350r2) may be used to apply torque to the hollow torque shaft (200).

Figure 48A:
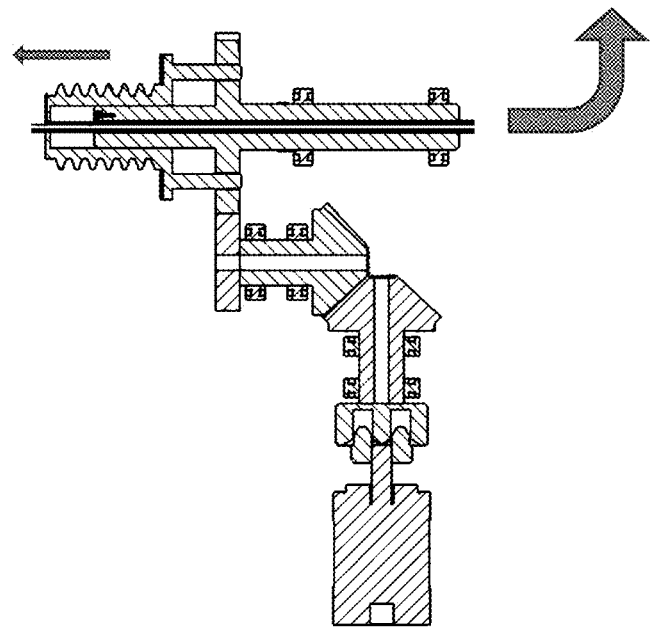
FIG. 48A shows a cross-sectional view of the rotary and linear drive system.
Figure 48B:
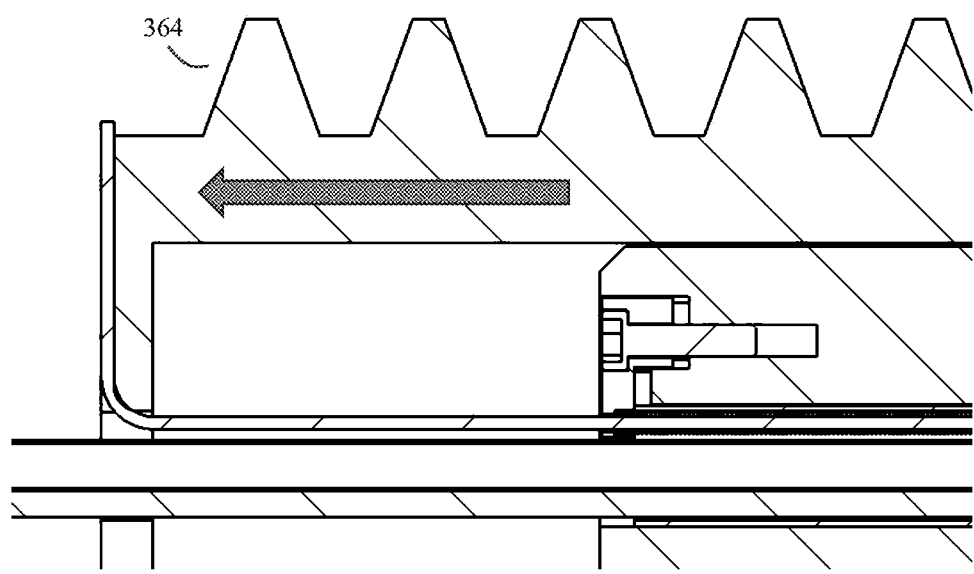
FIG. 48B shows further details of FIG. 48A.

By contrast, in FIG. 48A and FIG. 48B, the Linear Circular Gear Rack is actuated, and the catheter system is in the flexed state (large gray arrow turned up)

FIG. 48A shows a cross-sectional view of the rotary and linear drive system. Here the drive is in a second "actuated or flexed" state. Here the relative motion of the flexing actuator (364) has moved the distal or proximal steering cable (220 or 210) moved towards full tension. As a result, this steering cable tugs on its respective other end of the catheter, causing either the outer distal (108) or proximal (106) catheter tubes to become fully flexed or curved.

FIG. 48B shows further details of FIG. 48A. In the relaxed state shown in FIG. 47A/47B or flexed state shown in FIG. 48A/48B, the distal drive section (342) and proximal drive section (344) can be rotating along with the respective distal or proximal catheters at any rotational position independent of one another.

Figure 49A:
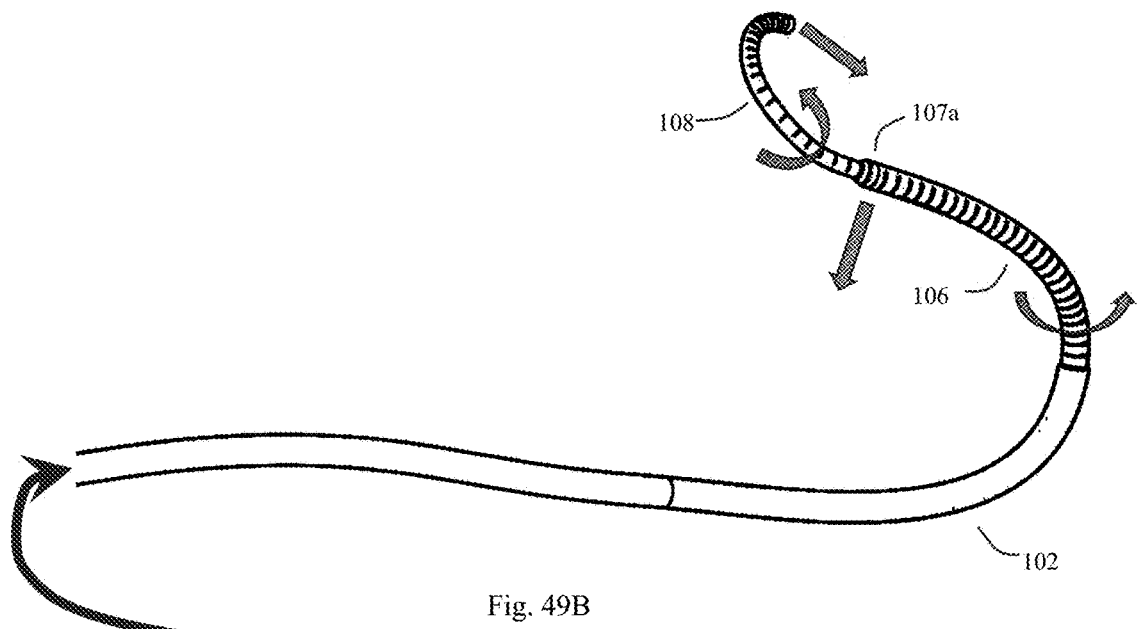
FIG. 49A shows how the rotary and linear drive system can drive the proximal and distal stages of the multi-stage catheter.
Figure 49B:
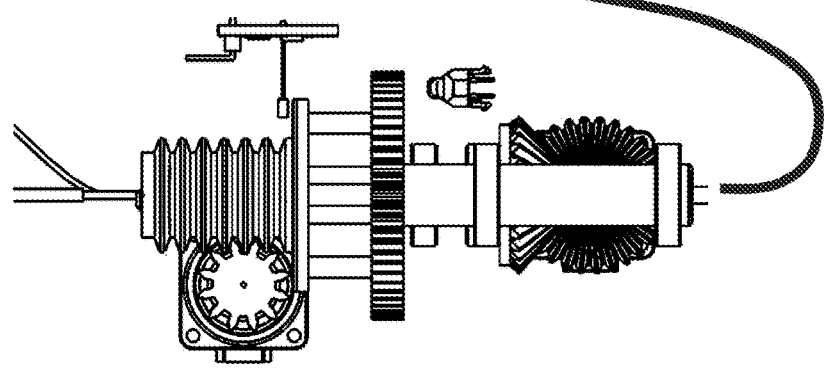
FIG. 49B shows a close-up of a portion of the rotary and linear drive.

FIG. 49A and FIG. 49B shows the actuation of the Distal or Proximal drive stage in the flexed position and rotating. For this example, only one drive stage is shown. This basic design can work for either Proximal or Distal catheter stages for both rotate and flex operations.

FIG. 49A shows how the rotary and linear drive system can drive the proximal and distal stages of the multi-stage catheter. Here the distal stage (108) is flexed and rotating counter clock wise. The distal flexion can be by tension transmitted by distal stage steering cable (220) to the distal tool plate (108). The distal stage rotation can be transmitted by the (distal) torque shaft (200). At the same time, the proximal stage (106) is also flexed and rotating counter clock wise as well. The proximal stage flexion can be by tension applied to a proximal stage steering cable (210) to the transition housing (107a). The proximal stage rotation can be transmitted by either rotation of a different proximal torque shaft (not shown), or by rotation of the outer portion of the proximal catheter (106) which may be transmitted through a hollow sheath (102) or other device.

FIG. 49B shows a close-up of a portion of the rotary and linear drive (here one of 342 or 344 is shown) system during the driving process of the multi-stage catheter shown above in FIG. 49A.

Assume here that both drives 342 and 344 are operating, even though only one of the drives is shown.

Here, the Circular Linear Gear Rack (drive rack 364), has been extended by the driving force of the Linear Circular Pinion Gear (374). This controls tension in the distal (and in this case also) proximal steering cables (220 and 210), causing the outer distal (108) and proximal (106) portions of the catheter to bend. At the same time, the distal and proximal rotary drive gear (368) can also rotate the outer tubes for the distal (108) and proximal (106) stages. This rotation can be done using the torque shaft (200) for the distal stage (108), and by rotating the outer casing of the proximal stage (108) either directly, or by way of a different proximal stage torque shaft (not shown).

Figure 50:
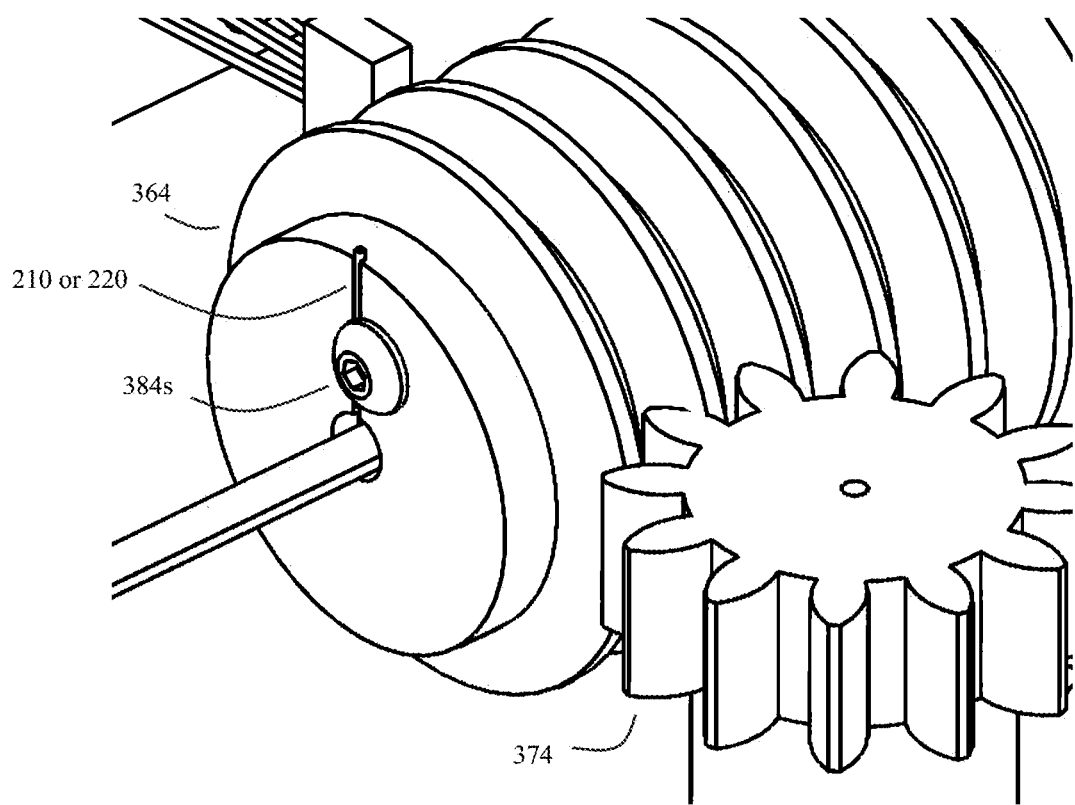
FIG. 50 details how the multi-stage catheter's steering cable(s) may be attached to a circular-linear gear rack on the driving mechanism.
Figure 51:
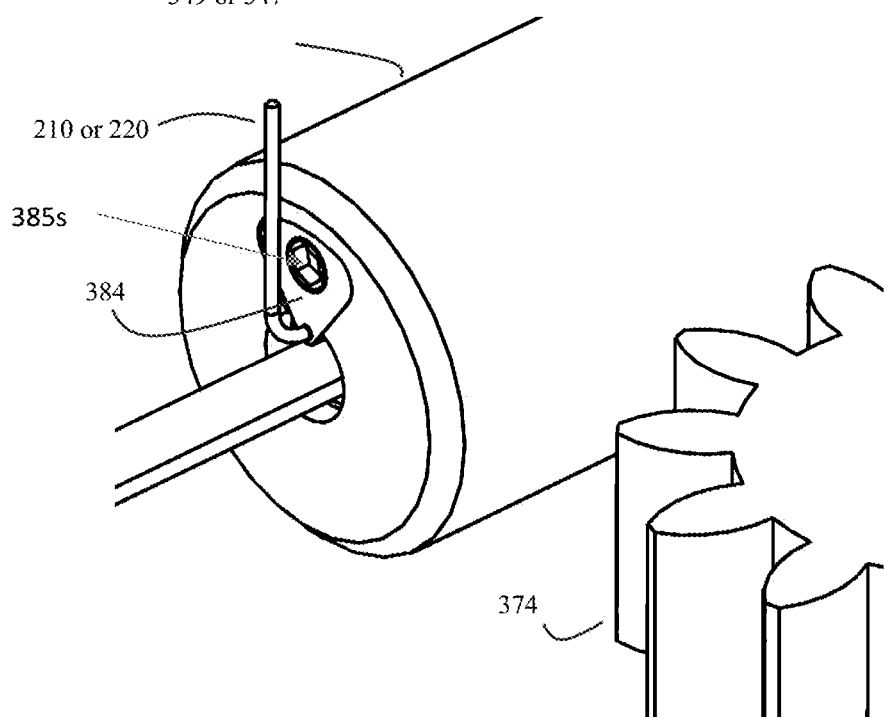
FIG. 51 shows the interior of the mechanism previously shown in FIG. 50.

FIG. 50 shows a detail of how the Flex Cable may be attached to the Circular Linear Gear Rack. By contrast, FIG. 51 shows a detail of this design with the Circular Linear Gear Rack removed, thus exposing the Drive Body Shaft with the Flex Cable protruding from the Adjustable Isolation Coil Stop. Again, The Circular Linear Gear Rack slides and rotates about the Drive Body Shaft.

FIG. 50 details how the multi-stage catheter's steering cable(s) (210 or 220) may be attached to a circular-linear gear rack on the driving mechanism. This can be done by a distal or proximal steering cable retaining clamp screw (384s) or other mechanism.

FIG. 51 shows the interior of the mechanism previously shown in FIG. 50. Here the circular-linear gear rack (364) has been removed, exposing the multi-stage catheter's drive body shaft (349 or 347) with a steering cable (210 or 220) protruding from the adjustable isolation coil stop (384). This later shows a screw (385s) for setting coil compression along the isolation coil (380).

FIG. 52 shows a cut view through the Drive Body Shaft, Torque Shaft, exposing the Adjustable isolation Coil Stop and Screw (385s), Flex Cable and Isolation Coil at the proximal drive end.

FIG. 52 shows a more detailed cross-section of the device previously shown in FIG. 51. This cross-section of the distal or proximal linear circular gear rack shows the distal or proximal torque shaft (200) and exposes the adjustable isolation coil stop (384).

Here the adjustable isolation coil-stop and screw (384) compresses the isolation coil (380), and isolates steering cable tension to the isolation coil. As a result, any tensioning forces are only transmitted after the cable leaves the isolation coil. This isolation eliminates the cross-transmission of tensioning forces between multiple stages that work through these rotary couplers. More specifically, the adjustable isolation coil stop (384) compresses the isolation coil (380) along the cable's length so that the steering cable (220) that transmits tension through to the distal stage (106) (such as to the distal tool plate 109) does not also transmit forces to the proximal stage (108) by applying unwanted force to the hollow rotatable coupler (107a). This helps keep the various steering cables from interfering with each other.

In some embodiments, according to the invention, any of the at least one proximal stage steering cable (210) and at least one distal stage steering cable (220) may be each further disposed inside their own isolation coil (380). This isolation coil will further comprise a far-isolation-coil-end and a near-isolation-coil-end.

For each isolation coil, the far-isolation-coil-end is attached proximate to a distal terminus of its corresponding steering cable (such as 210, 220) in a manner that allows the corresponding steering cable to movably protrude past the far-isolation-coil-end, while also blocking axial movement of the far-isolation-coil-end. In other words, the end of the isolation coil is held in place, but the steering cable inside protrudes out and can slide back and forth as it retracts in the flexible portion of the catheter.

Similarly, each near-isolation-coil-end is attached proximate to its respective flexing actuator in a manner that allows the corresponding steering cable to movably protrude past the near-isolation coil end while blocking axial movement of the near-isolation-coil-end. In other words, the other end of the isolation coil is also held in place, but the opposite end of the steering cable inside protrudes out and can also slide back and forth.

As before, to prevent tangling and jamming the system will further rotate each of the isolation coils in a 1:1 ratio with any rotation of its respective steering cable and any of its respective proximal stage and distal stage. This enables variable tension applied by each said respective flexing actuator to be isolated to its respective steering cable while the cable is inside its respective isolation coil.

Figure 53C:
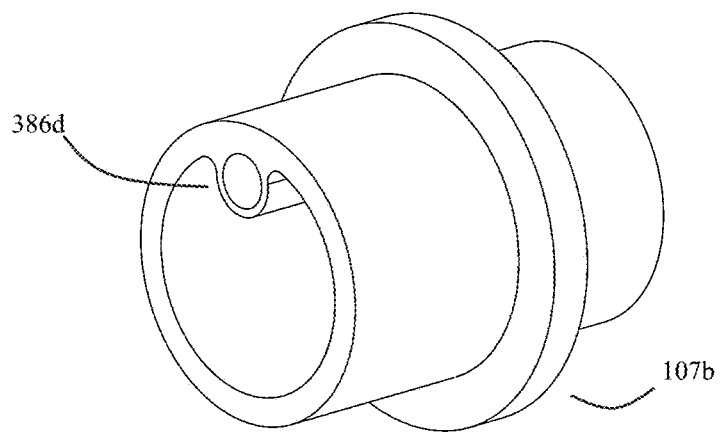
FIG. 53C shows a detail of the hollow rotatable coupler part of the transition housing.

FIG. 53A, FIG. 53B, and FIG. 53C show how the Isolation Coil typically traverses the length of the Proximal Stage catheter, and is often terminated at a Distal Isolation Coil Stop. This allows the Distal Flex Cable to transmit tension to only the Distal Stage. This can be used to independently transmit force to an attachment at the far distal end of the catheter. This can be to a tool plate, or through a hole in the wall of the catheter where the cable is then terminated and attached (e.g. by glue, welding, or crimp). Therefore, the Isolation Coil enables transmission of mechanical tension to be focused and distributed to only the portion of the catheter that is designed to flex.

FIG. 53A shows an exterior portion of the multi-stage catheter near the transition housing (107a) between the proximal (106) and distal (108) stages.

FIG. 53B shows a cross-section of the region shown in FIG. 53A, showing a detail of a distal stage steering cable (220) and isolation coil (380). The far isolation coil end of this isolation coil is attached to a distal coil stop (386d) on the hollow rotatable coupler (107b) part of the transition housing (107a), while the distal stage steering cable (220) protrudes past this region and into the distal end (108) of the multi-stage catheter.

FIG. 53C shows a detail of the hollow rotatable coupler (107b) part of the transition housing (107a), showing that in this embodiment the hollow rotatable coupler has been modified to further comprise a distal isolation coil stop (386d) that attaches to the distal end of the isolation coil (380), and prevents movement of the isolation coil. However, the distal steering cable (220) protrudes past this stop (386d) and into the distal end of the multi-stage catheter.

In some embodiments, according to the invention, isolation coil may have an isolation coil compression. Here, at least the near-isolation-coil end is attached proximate to its respective flexing actuator in a manner which further enables this isolation coil compression to be adjusted by any of a manual isolation coil compression adjuster and and/or compression actuator (such as a processor activated compression actuator).

Figure 54A:
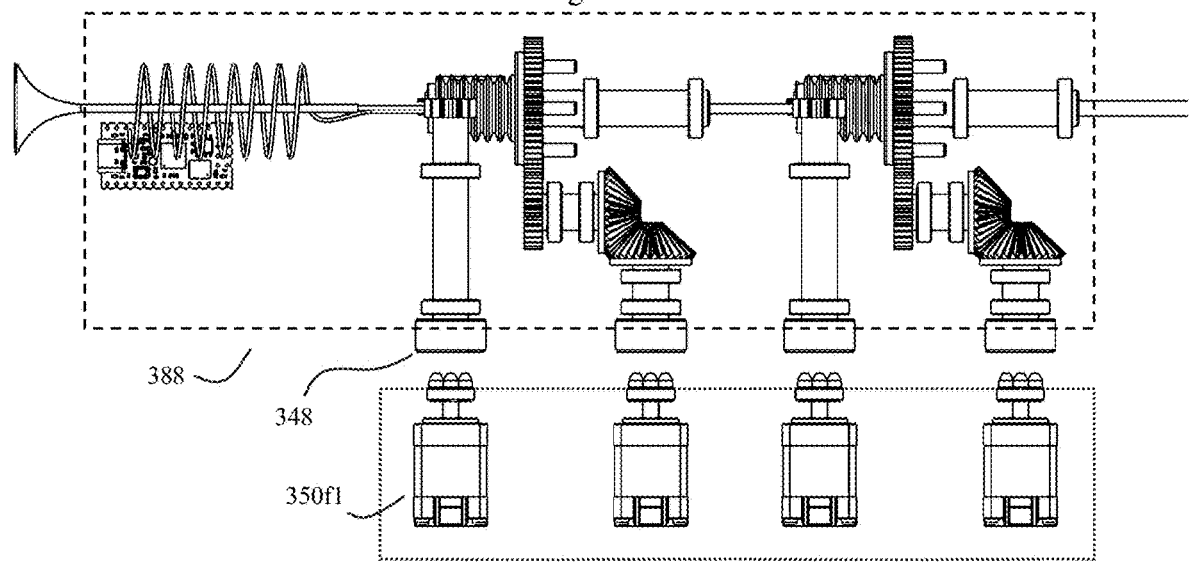
FIG. 54A shows how a disposable housing or cartridge may contain the proximal drive side (or gear train) of the multi-stage catheter driving assembly.
Figure 54B:
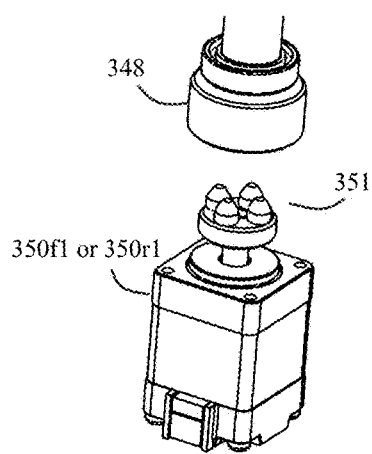
FIG. 54B shows a detail of how a motor coupler from a gear train from the disposable housing/cartridge may interact with the drive pins of an actuator.
Figure 54C:
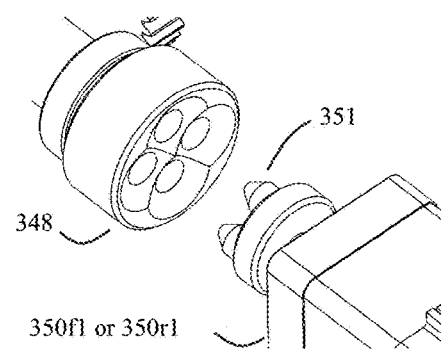
FIG. 54C shows another view of how a coupler from a gear train from the disposable housing/cartridge may interact with the drive pins of an actuator.

FIG. 54A, FIG. 54B, and FIG. 54C show how the proximal drive side of the catheter can be contained in a disposable housing. The disposable housing can be coupled to an array of drive motors that are attached to a fixed platform such as the robotic arm. The motors have a drive hub with protruding pins attached to the output shaft. The motor hubs drive pins engage with a coupler that is directly connected to the drive train gears of the cartridge.

FIG. 54A shows how a disposable housing (388) may contain the proximal drive side (or gear train) of the multi-stage catheter driving assembly. This in turn may interact with the various actuators (e.g. electric motors) disposed on a robotic arm or other platform.

FIG. 54B shows a detail of how a motor coupler (348) from a gear train from the disposable housing (388) may interact with the drive pins (351) of an actuator (such as 350/1, 350/2 or 350r1, 350r2).

FIG. 54C shows another view of how a coupler (348) from a gear train from the disposable housing (388) may interact with the drive pins (351) of an actuator (such as 350/1 or 350r1).

In some embodiments, the at least one contacting mechanism may comprise at least one gear assembly (for example, any of 354, 364, 366, 368, 370, 374 or other gears that conduct force from one or more actuators to various parts of the catheter). Here, at least portions of this gear assembly may be configured in a disposable or reposable cartridge (388) that can be reversibly coupled and decoupled from the various one processor-controlled electromagnetic actuators (such as any of 350/1, 350/2, 350r1, 350r2). Thus, the electromagnetic actuators may be more permanently mounted on a robotic arm, while the disposable and preferably sterilized gears in the cartridge (388) can be mounted and either discarded or refurbished for subsequent use.

Note that in some embodiments, the contacting mechanism may alternatively comprise a lever/finger or fork with a fulcrum connected to an actuator that rests inside of a groove or over a protruding ring of the rotatable slidable element. This lever/finger or fork can push or pull against either edge in the groove or over the ring with two edges.

Figure 55:
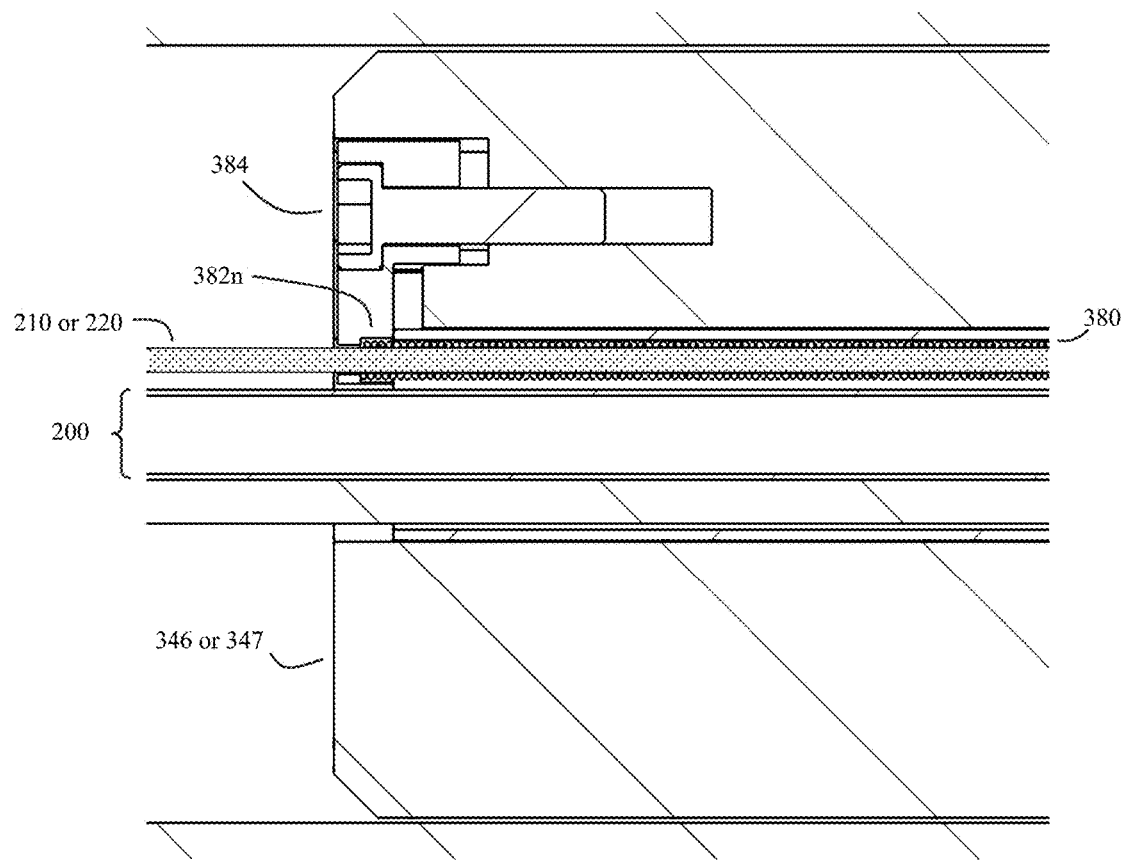
FIG. 55 shows a detail of how a hollow torque shaft, proximal or distal steering cable, and isolation coil may be configured.

FIG. 55 shows how the Distal or Proximal Torque shafts may be fitted and adhered inside of the Drive Body Shaft.

FIG. 55 shows a detail of how a hollow torque shaft (200), proximal or distal steering cable (210, 220), and isolation coil (380) may be configured. This shows a clearer view of the proximal isolation coil stop (382n) that acts to constrain the motion of the proximal end of the isolation coil (380). Note that in FIG. 55, in some embodiments, the outer tube body for the proximal end of the catheter 106) or an equivalent proximal torque shaft may be glued or otherwise adhered or affixed to the drive body shaft (e.g. 347).

An important aspect of this invention is the combination of independent linear actuation while rotating the two or more stages. This is how the stages may be rotated, while the various cables and flexing cables located internal to the stages can maintain their proper orientation with respect to each other. This helps prevent cables from twisting and tangling with each other.

Figure 56:
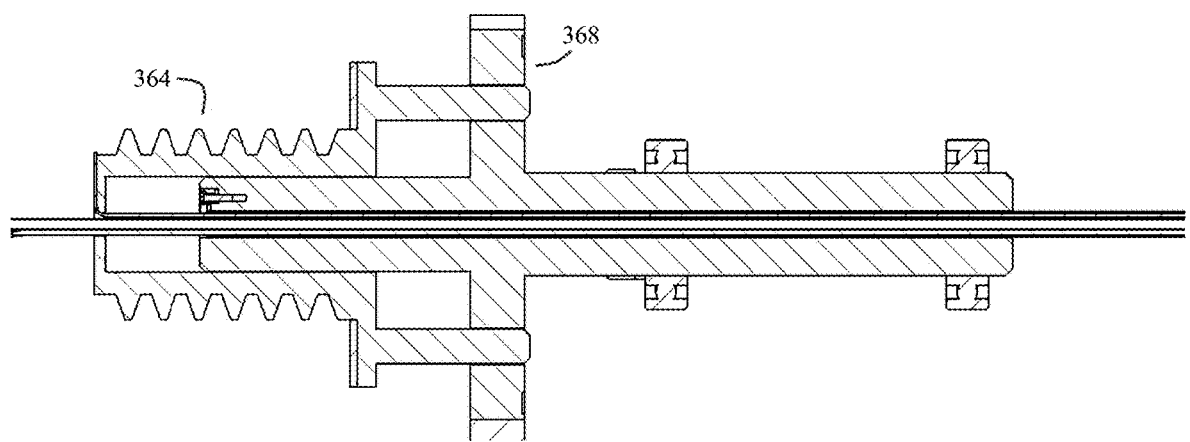
FIG. 56 shows a further detail of how the components that tension the steering cable(s) must be directly synchronized 1:1 with the components that rotate the multi-stage catheter.

FIG. 56 shows the basic principle. The elements that tension the cable must be directly synchronized (mechanically or magnetically) with the elements that rotate the entire catheter. Stated another way the tensioning elements rotate along with the rotating torque drive elements. Thus, if the rotating torque drive rotates 15 degrees, the tensioning elements also rotate 15 degrees in the same direction. Here, this coupled rotation between the tensioning elements (such as the steering cables 210, 220 used to flex or steer the catheter), and the rotation of the catheter torque shaft (200) or the outside proximal catheter (106) is termed a "1:1 rotation." In the event of conflicts, the system processor (410) will couple the rotation to avoid twisting the steering cables and/or jamming the system. Thus, an alternate definition of "1:1 rotation" is "to rotate the steering cables/tensioning elements in synchronization with any rotation of at least the distal (108) and proximal (106) portions of the catheter to minimize twisting or jamming of the steering cables (210, 220)."

FIG. 56 shows a further detail of how the components that tension the steering cable(s) must be directly synchronized with the components that rotate the multi-stage catheter.

Further Methods of Actuating a Rotary Robotic Catheter

To generalize the concepts above for the purposes of writing broader claims, methods actuation not using gears are described below for other types of actuation of a Rotary-Linear drive stage.

The rotary or linear actuation can be driven by electromagnetic, shape memory alloy actuator, air power, vacuum, etc.

Figure 57A:
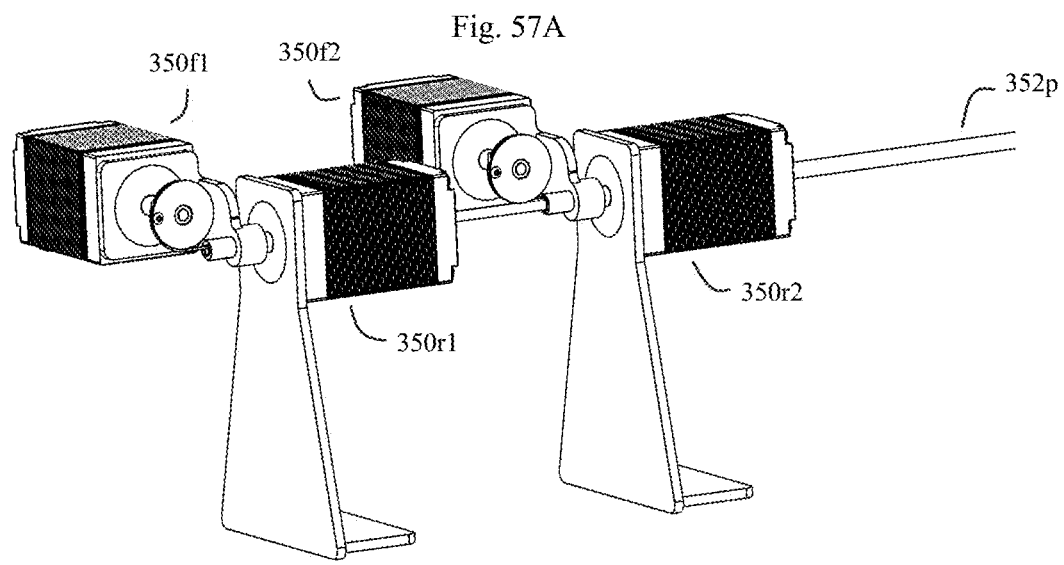
FIG. 57A shows an alternative configuration where two flexing actuators are configured to rotate about two rotary actuators without gears.
Figure 57B:
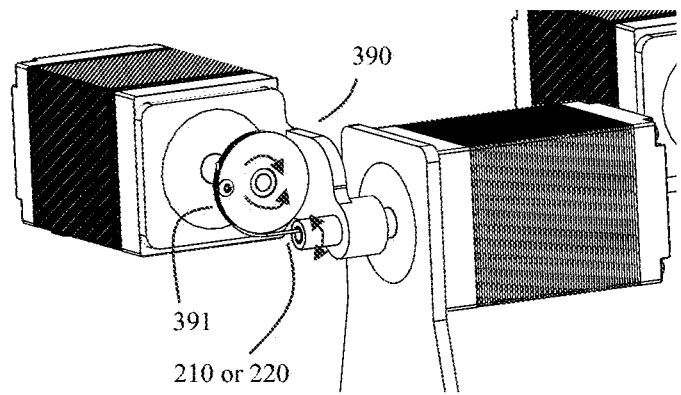
FIG. 57B shows a detail of the device previously shown in FIG. 57A.

As shown in FIG. 57A and FIG. 57B, in this alternative embodiment, the electromagnetic linear actuator (motor) rotates about the rotary drive motors axis. This embodiment does not use drive pins for keeping the linear actuators synchronized with the rotary actuators. Instead, a rigid mount fixes the linear actuator to the rotary actuator. These motors can be open loop or closed loop DC or AC type motors. The electrical wires for the spinning motors are managed by providing extra length such that the motors can rotate beyond 360 degrees in either direction depending on the wire coil loop size. These examples can be used for one catheter or two or more catheters connected by a transition housing and rotational coupler.

FIG. 57A shows an alternative configuration where two flexing actuators (350/1, 350/2) are configured to rotate about two rotary shaft actuators (350r1, 350r2) without the use of gears. These can in turn be affixed to bases that are rigidly fastened together on translation slide of a robotic arm or other support. Note that in this embodiment, the linear or "flex" actuators (350f1, 350f2) are rigid and can be fixed mechanically to the rotary actuators (350r1, 350r2) by a mounting plate (390). This mounting plate (390) can be considered to be another type of contacting mechanism.

FIG. 57B shows a detail of the device previously shown in FIG. 57A. This also shows further details of a linear steering cable and actuator pulley (391) that may be used to apply tension to the steering cables such as (210 and 220).

Figure 58A:
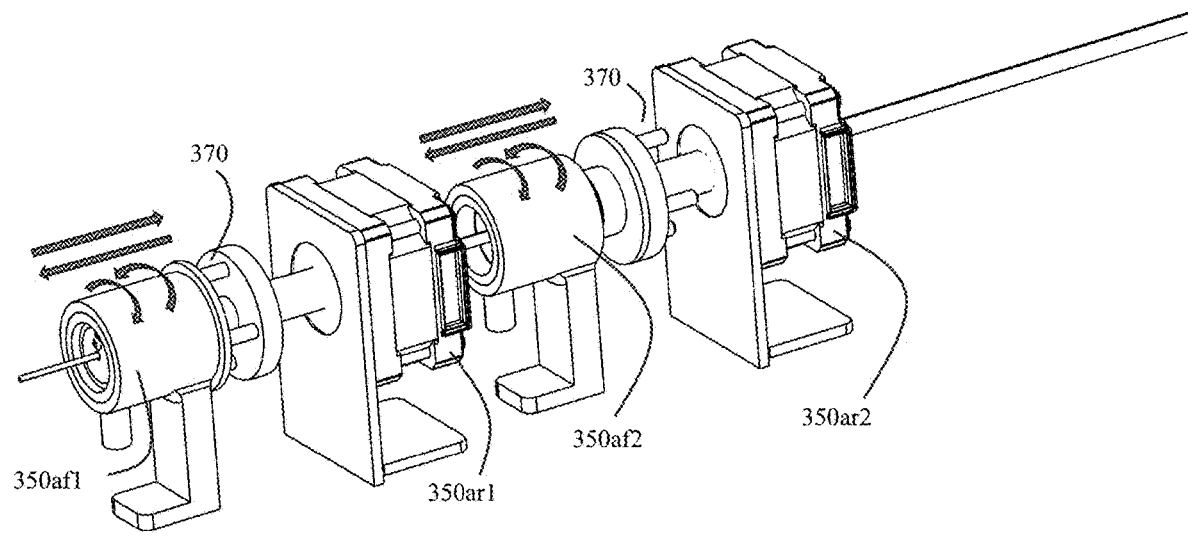
FIG. 58A shows another alternative configuration where the distal and proximal stages of the multi-stage catheter are driven by alternative types of electromagnetic actuator systems.
Figure 58B:
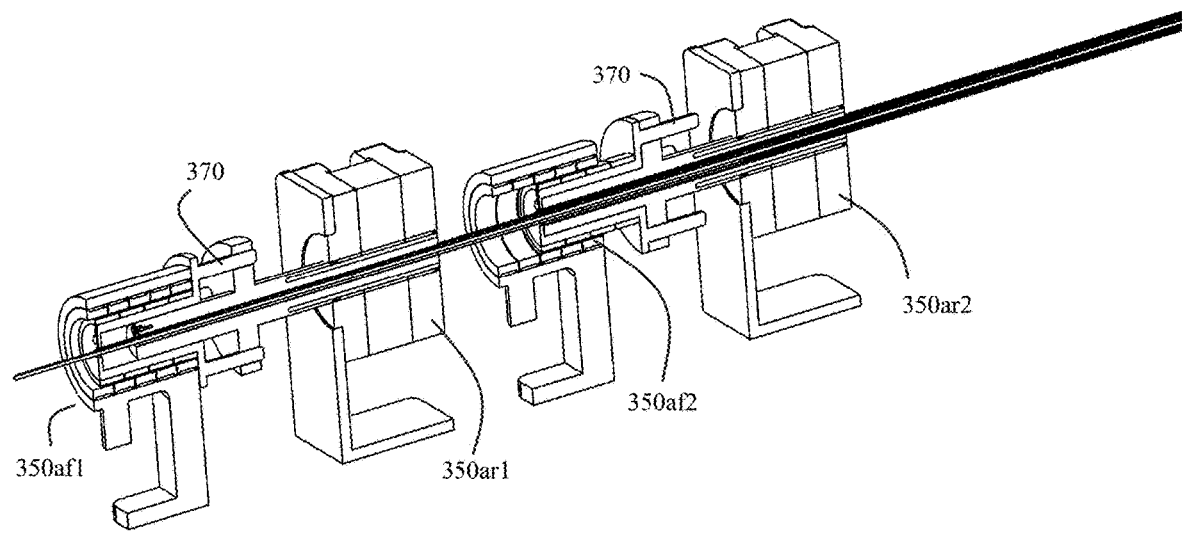
FIG. 58B shows a cross-section of the system previously shown in FIG. 58A.

FIG. 58A and FIG. 58B show another alternative embodiment where the Distal and Proximal stages are coupled stages that are driven by alternative electromagnetic actuator systems. Here the rotational actuation is powered by through-shaft motors, and the linear actuation is powered by linear electro-magnetic motors that pull the flex cables. In this embodiment, electrical motor wire management is not necessary since both the rotary and linear motors can be of a through-hole type design.

FIG. 58A shows another alternative configuration where the distal and proximal stages of the multi-stage catheter are driven by alternative types of electromagnetic actuator systems (350af1, 350af2, and 350ar1, 350ar2). Here, the 350af1 and 350af2 actuators are linear motors, such as solenoids, creating and releasing tension on their respective steering cables. By contrast, 350ar1 and 350ar2 actuators can be through-hole shaft motors. As before, the apparatus uses sliding drive pins (370) to ensure that the system creates and releases tension on the steering cables in a 1:1 ratio with any rotation.

In FIG. 58A, the proximal steering cable is not under tension by 350af2, while the distal steering cable is under tension by 350af1.

FIG. 58B shows a cross section of the system previously shown in FIG. 58A. Here actuators (350af1 and 350af2) are shown placed on a stator platform. Actuators 350ar1 and 350ar2 have a drive body shaft that is bonded to the motor shaft.

Figure 59A:
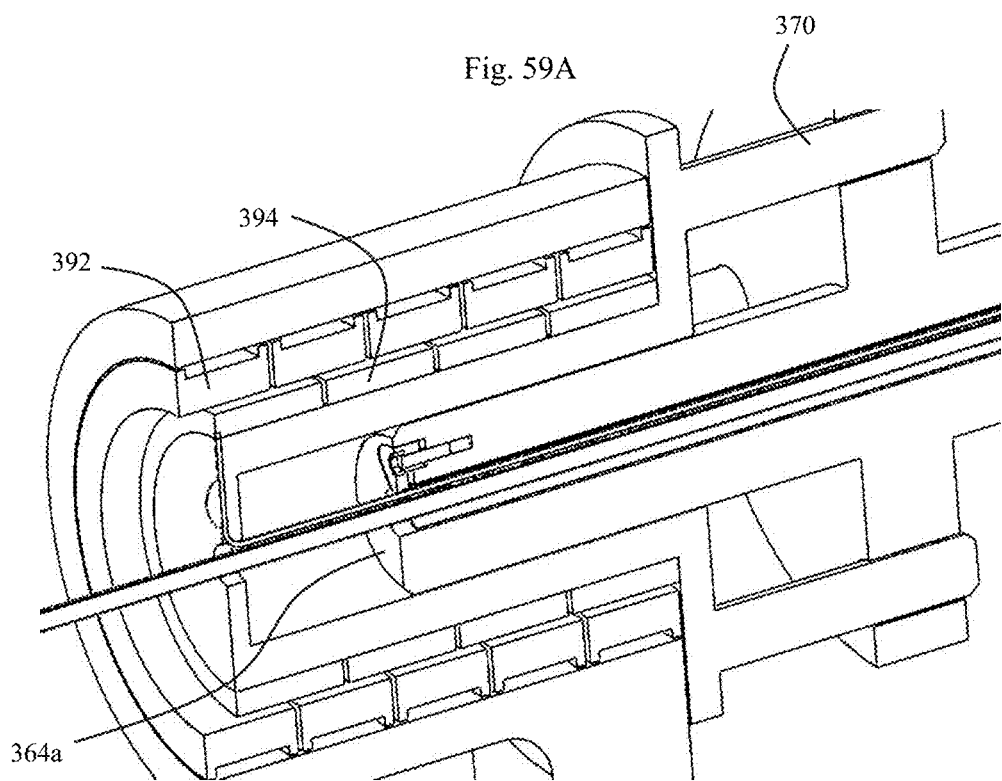
FIG. 59A shows a detail of the alternative configuration previously shown in FIG. 58A and FIG. 58B.

FIG. 59A shows a detail of this alternative embodiment.

FIG. 59A shows a detail of the alternative configuration previously shown in FIG. 58A and FIG. 58B. Here, the processor-controlled stator windings (392), which can be bonded to the stator platform, can actuate one or more magnetic sliders, such as neodymium slider ring magnets (394), which in turn can be bonded to a linear steering cable slider element (364a). This arrangement acts much like an alternate version of the previously discussed circular-linear gear rack (364) previously discussed. Hence, this is designated (364a).

Figure 59B:
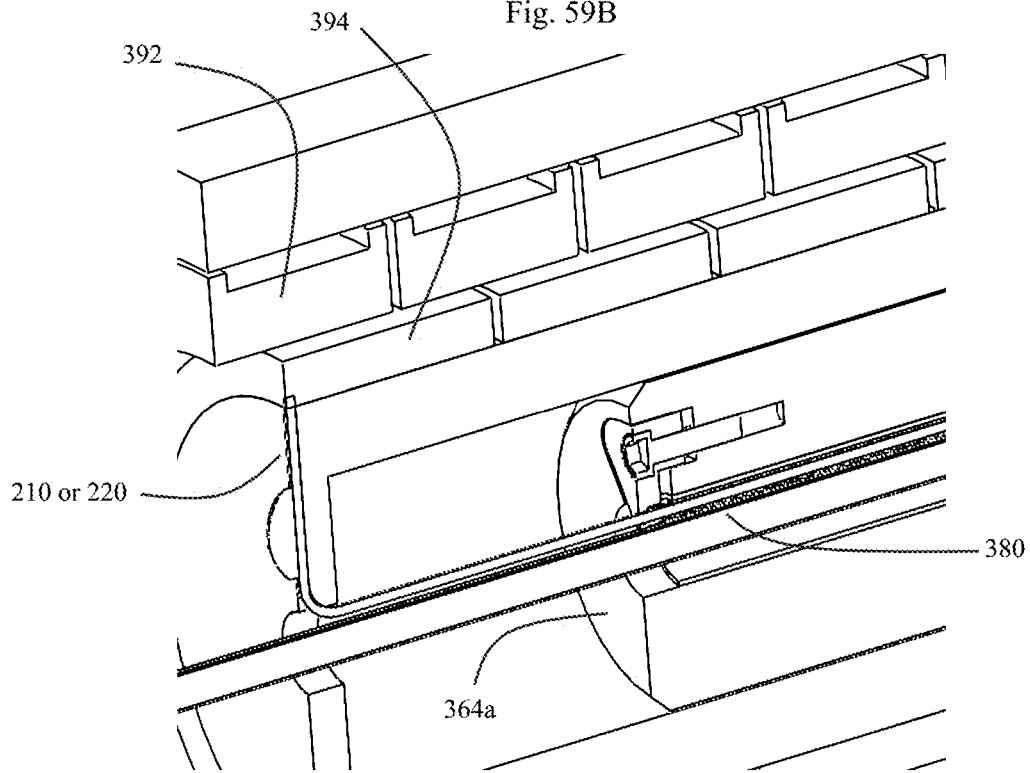
FIG. 59B shows another detail of the alternative configuration previously shown in FIG. 58A and FIG. 58B.

FIG. 59B shows another detail of this alternative embodiment.

FIG. 59B shows another detail of the alternative configuration previously shown in FIG. 58A and FIG. 58B. Other parts of this system are generally as previously described.

Rotary-Linear Robotic Cather System with Independently Rotatable, Flexing, and Slidable Catheters Using the simplified method of linear actuator motor with a pulley spinning about a through-hole motor, the concept of a system of catheters is described where each catheter stage motor can also linearly traverse along a linear translation stage. This concept works well for schematically describing the Rotary-Linear Robotic Cather System with Independently Rotatable, Flexing, and Slidable Catheters.

Figure 60:
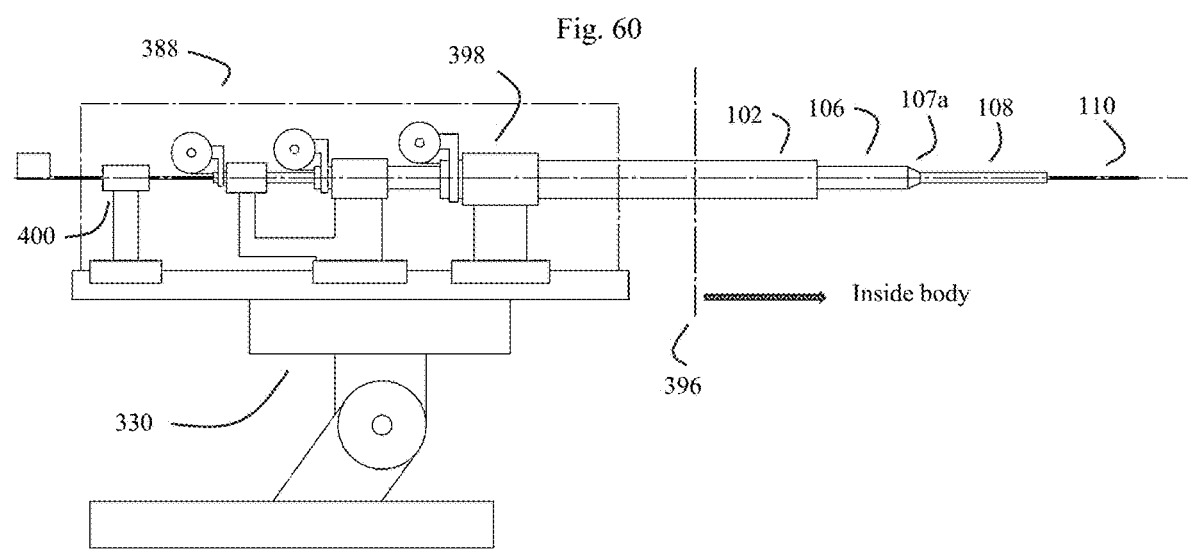
FIG. 60 shows an alternate view of the rotary-linear robotic catheter system with independently rotatable, flexing, and slidable catheters.

FIG. 60 shows an example of an architecture for a Rotary-Linear Robotic Cather System with Independently Rotatable, Flexing, and Slidable Catheters The Distal and Proximal stage are coupled at the transition housing and at the slide of the Linear Transitional Stage. The Therapy and the Steerable Robotic Sheath translate along the Linear Translation Stage independently. The motorized linear translation stages drive the sheath, catheters, and therapy device into the patient's internal body pathways.

FIG. 60 shows an alternate view of the rotary-linear robotic catheter system with independently rotatable, flexing, and slidable catheters. Note that while operating on a patient, often at least the distal portion of sheath (102), and the remaining distal components (e.g. 106, 107a, 108, 110, etc.) be inserted into the patient (e.g. catheter components to the right of the dividing line 396). By contrast, the various actuators, gears, robotic arms, and other portions of the system to the left of diving line 396 will remain outside of the patient. These later systems may be mounted on a robotic arm, such as previously described (330).

Note that in some embodiments, a similar type 1:1 synchronized linear and rotary drive system, and optional sheath steering cable(s), may also be used to control the movement of the sheath (102) while inside the body. This optional sheath system is shown as (398). Additionally, other actuator systems, such as therapy payload conduit dispensing system (400) may also be used. Here the therapy delivery or producing unit itself is shown as (401).

In some embodiments, according to the invention, at least the proximal portions of the proximal stage hollow catheter (106) may be disposed within at least one hollow sheath (102). This at least one hollow sheath may be configured to enable at least portions of the multi-stage catheter device to (axially) protrude or retreat inside and outside of said at least one hollow sheath, depending on forces applied to said at least one hollow sheath (102) and at least said proximal stage hollow catheter (106). Here, the axial movement of this said hollow sheath may be controlled according to a sheath translation stage actuator (402s) and optionally by processor (410) or another controller as well.

Figure 61A:
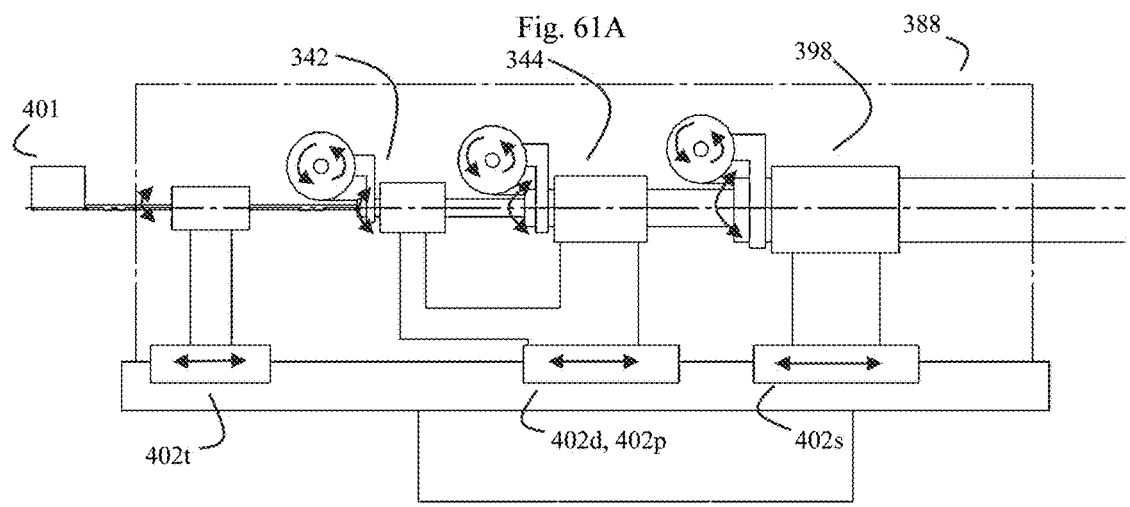
FIG. 61A shows further details of the drive system previously shown in FIG. 60.
Figure 61B:
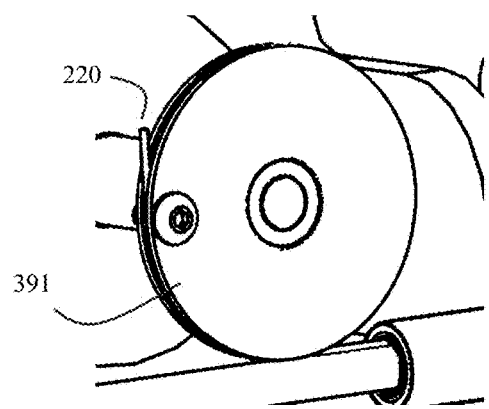
FIG. 61B shows a further detail of a distal steering cable actuator previously shown in FIG. 60 and FIG. 61A.

FIG. 61A shows further details of this drive system, while FIG. 61B shows a detail of the distal flex cable actuator.

In some embodiments, the device further comprises at least one sheath steering cable (FIG. 16, 102b) connected to a distal end of the sheath (102). This at least one sheath steering cable is disposed inside the sheath, and outside of (at least the proximal and distal portions of the) multi-stage catheter device.

Figure 62:
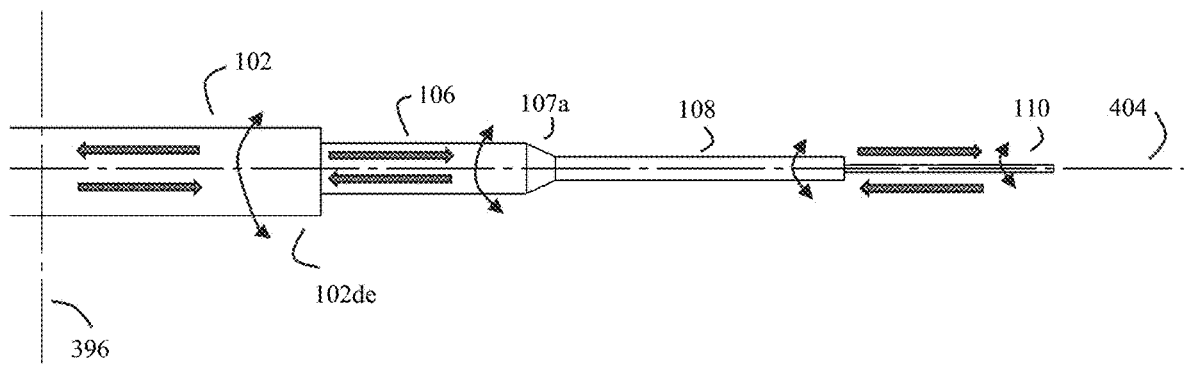
FIG. 62 is a close up of the right side of FIG. 60, showing in more detail how the robotic drive system enables the sheath, proximal and distal catheter sections, and the therapeutic payload conduit, to slide in-and out and rotate independently.

According to the invention, this at least one sheath steering cable (102) can be configured to convey sheath off-axis steering force on the distal end of said sheath (see FIG. 62, 102de). This causes the distal end of the sheath and the rest of the multi-stage catheter device to move off-axis according to this sheath off-axis steering force.

Here, as per the proximal and distal sections, this sheath off-axis steering force can be further controlled by using by a sheath steering cable actuator (398) to create and release tension on this at least one sheath steering cable.

FIG. 61A shows further details of the drive system previously shown in FIG. 60. The various actuator systems can include a distal steering cable and rotary actuator (such as 342), a proximal steering cable and rotary actuator (such as 344), a sheath steering cable and rotary actuator (398), and a therapy payload insertion/removal actuator (400). Each of these actuators in turn can be mounted on various translation stage motors (e.g. 402t, 402d, 402p, 402s) to control how far the payload conduit, distal stage, proximal stage, or sheath is inserted or removed into the patient. This allows each individual catheter section (110), (108), (106), (102) to be independently extended or contracted as needed.

In some embodiments, according to the invention, at least one payload (401) may be moved along the working channel by using at least one payload dispensing actuator (402t) to advance or retract a payload dispensing conduit along this working channel (FIG. 16, 228).

FIG. 61B shows a further detail of a distal steering cable actuator previously shown in FIG. 60 and FIG. 61A. Note the steering cable (220) which, in this embodiment, is attached to a pulley around an actuator motor shaft. See FIG. 57B for more detail.

FIG. 62 shows how this drive system enables the proximal and distal catheter sections to slide and rotate independently of any steerable sheath (such as an optional steerable robotic sheath).

FIG. 62 is a close up of the right side of FIG. 60, showing in more detail of how the robotic drive system enables the sheath, proximal and distal catheter sections, and the therapeutic payload conduit, to slide in-and out independently. The sheath, proximal section, and distal sections, and optionally the therapeutic payload conduit can also rotate independently, as well as bend or flex independently, all while being positioned inside the patient (to the right of 396). These movements are shown by the various arrows. The axis of rotation is also shown (404).

Materials: all the catheters above can be constructed from polymers of one more durometer or a mix of metal components and polymers of varying durometers. This includes the proximal and at least one distal concentric stage, connected by a transition housing and rotational coupler.

Tracking the System of Catheters

For the Rotary-Linear Robotic Cather System with Independently Rotatable, Flexing, and Slidable Catheters, a method of tracking catheters in real-time while in the patient is described.

Figure 63:
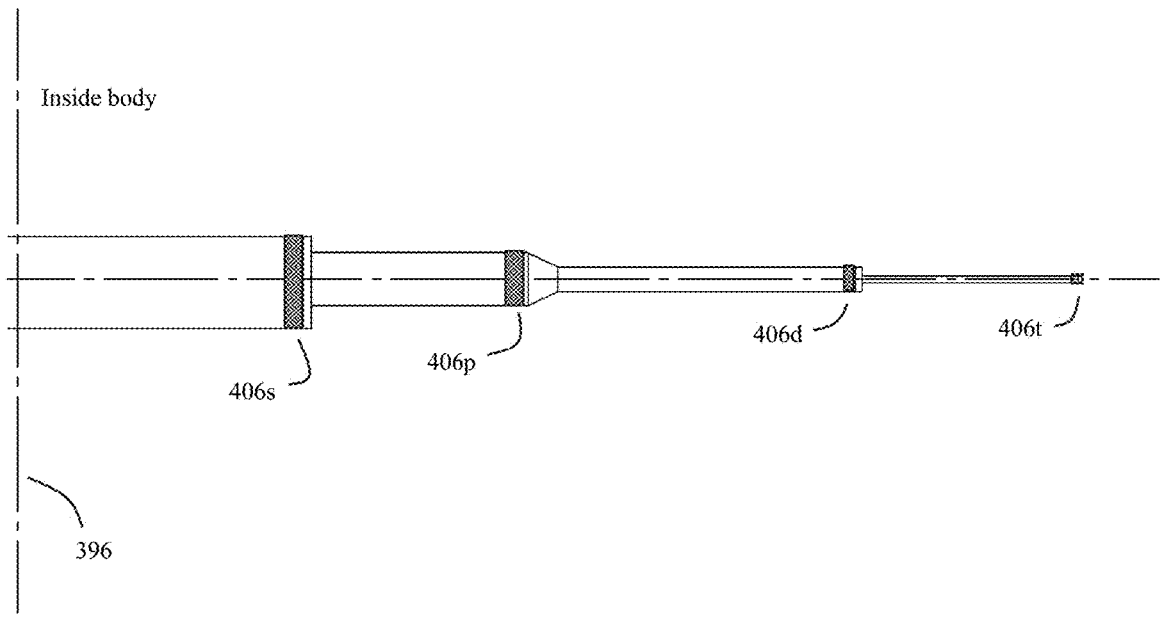
FIG. 63 shows that in some embodiments, portions of the multi-stage catheter may comprise radio-opaque material.

FIG. 63 shows how in some embodiments, each catheter stage may further include a radio-opaque component, such as a Platinum ring. When used with an imaging system, such as Real time CT, these radio-opaque elements enable the position of each catheter tip to be tracked. Thus, each far distal catheter axis is defined by two points at any time. This enables the far distal ring of the catheter section and the next proximal ring to be determined.

FIG. 63 shows that in some embodiments, portions of the multi-stage catheter may comprise radio-opaque material. Here, for example, radio-opaque materials, such as platinum rings, can be used to facilitate real-time position sensing and provide full path geometric trajectory under various imaging techniques, such as C-arm fluoroscopy (previously shown in FIG. 23). These radio-opaque materials (406s, 406p, 406d, 406t) may be positioned at key points on the catheter, such as at or near distal end of the sheath, the distal end of the proximal catheter, the distal end of the distal catheter, and on any probe or needle tip as well.

Figure 64:
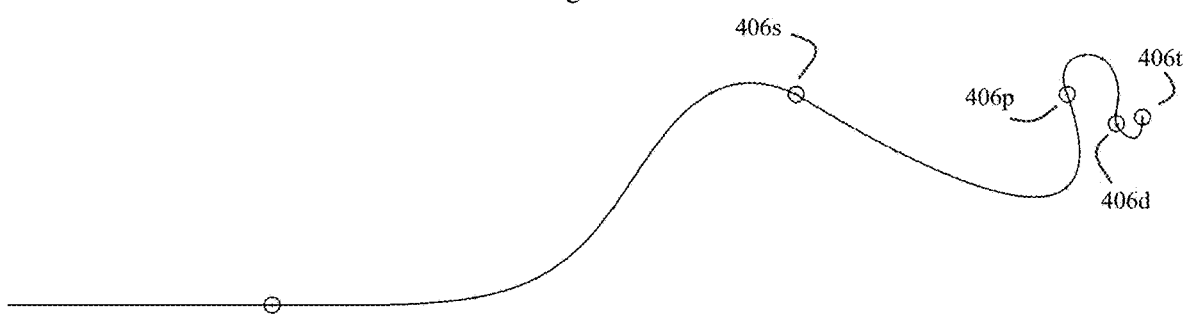
FIG. 64 shows that in some embodiments, an imaging system and the radio-opaque materials from FIG. 63 may be used to track the position and trajectory of the multi-stage catheter.

FIG. 64 shows an example of a curved trajectory path in flat 2D (3D is not shown to simplify the description). The circles represent the platinum markers, providing a minimum number of points to show a trajectory path under fluoroscopy. Additional markers could be added to more precisely define the true path for further computational requirements.

FIG. 64 shows that in some embodiments, an imaging system and the radio-opaque materials from FIG. 63 may be used to track the position and trajectory of the multi-stage catheter. In this example, (408) can correspond to the sheath position at the point where it is fixed to the rotary stage. This is a known reference point that is typically out of the view of the imaging system. Additional radio-opaque markers may also be used for higher precision trajectory path definition.

The invention claimed is:

1. A method of driving a multi-stage catheter device for traversing internal body passages, said multi-stage catheter device comprising:
    a distal stage hollow catheter and a different proximal stage hollow catheter;
    said distal stage hollow catheter being a rotating distal stage hollow catheter with a distal stage axis that is configured to rotate about a proximal stage axis of said different proximal stage hollow catheter;
    one end of said rotating distal stage hollow catheter affixed to an end of said different proximal stage hollow catheter by a transition point coupler;
    said transition point coupler configured to traverse an internal body passage;
    said transition point coupler comprising a transition housing that includes a hollow rotatable coupler, said hollow rotatable coupler configured as a rotary joint to enable said one end of said rotating distal stage hollow catheter to rotate about said end of said different proximal stage hollow catheter;
    said device further comprising a hollow torque shaft mounted inside said proximal stage hollow catheter and attached to said hollow rotatable coupler, said hollow torque shaft configured to convey torque to said rotatable coupler and said rotating distal stage hollow catheter;
    said device further comprising at least one proximal stage steering cable connected to said transition housing, said at least one proximal stage steering cable disposed inside said proximal stage hollow catheter, outside said hollow torque shaft, said at least one proximal stage steering cable enabled to convey proximal stage steering force on said transition housing, causing said transition housing and said distal stage hollow catheter to move according to said proximal stage steering force;
    said hollow torque shaft, distal stage hollow catheter, hollow rotatable coupler and said transition housing further comprising a working channel configured to convey a plurality of conduits through said proximal stage hollow catheter and said distal stage hollow catheter to at least a distal tool plate mounted on a distal end of said distal stage hollow catheter;
    wherein at least some of said conduits comprise at least one distal stage steering cable configured to convey distal stage steering force to said distal tool plate on said distal end of said distal stage hollow catheter;
    said at least one distal stage steering cable enabled to cause said distal tool plate and said distal stage catheter to further move according to said distal stage steering force;
    said method comprising:
    flexing and unflexing said end of said distal stage hollow catheter by using at least one distal stage tensioning actuator to create and release tension on at least one of said at least one distal stage steering cables while rotating said at least one distal stage steering cable in a 1:1 ratio with any rotation of at least said distal stage hollow catheter.

2. The method of claim 1, further comprising:
    moving said transition point coupler by using at least one proximal stage tensioning actuator to create and release tension on at least one of said at least one proximal stage steering cables while rotating said at least one proximal stage steering cable in a 1:1 ratio with any rotation of said proximal stage hollow catheter and said distal stage hollow catheter.

3. The method of claim 2, wherein any of said at least one distal stage tensioning actuator and said at least one proximal stage tensioning actuator comprises at least one contacting mechanism and at least one processor-controlled electromagnetic actuator; and further using at least one motion or position sensor to control said at least one processor.

4. The method of claim 3, wherein said at least one contacting mechanism comprises at least one gear assembly; and wherein at least portions of said gear assembly are configured in a disposable or reposable cartridge that can be reversibly coupled and decoupled from said at least one processor-controlled electromagnetic actuator.

5. The method of claim 1, further comprising:

moving at least one payload along said working channel by using at least one payload dispensing actuator to advance or retract a payload dispensing conduit along said working channel.

6. The method of claim 1, wherein any of said at least one proximal stage steering cable and at least one distal stage steering cable are further disposed inside an isolation coil comprising a far-isolation-coil-end and a near-isolation-coil-end;

each said far-isolation-coil-end is attached proximate to a distal terminus of its corresponding steering cable in a manner that allows said corresponding steering cable to movably protrude past said far-isolation-coil-end while blocking axial movement of said far-isolation-coil-end;

each said near-isolation-coil-end is attached proximate to its respective flexing actuator in a manner that allows said corresponding steering cable to movably protrude past said near-isolation coil end while blocking axial movement of said near-isolation-coil-end;

further rotating each said isolation coil in a 1:1 ratio with any rotation of its respective steering cable and any of its respective proximal stage and distal stage;

thus enabling variable tension applied by each said respective flexing actuator to be isolated to its respective steering cable while said cable is inside its respective isolation coil.

7. The method of claim 6, wherein each said isolation coil has an isolation coil compression;

at least said near-isolation-coil end is attached proximate to its respective flexing actuator in a manner which further enables said isolation coil compression to be adjusted by any of a manual isolation coil compression adjuster and a compression actuator.

8. The method of claim 1, further using a torque shaft actuator to apply torque to said hollow torque shaft.

9. The method of claim 1, wherein at least proximal portions of said proximal stage hollow catheter are disposed within at least one hollow sheath, at least one of said at least one hollow sheath configured to enable at least portions of said multi-stage catheter device to protrude or retreat inside and outside of said at least one hollow sheath, depending on forces applied to said at least one hollow sheath and at least said proximal stage hollow catheter;

further controlling axial movement of said hollow sheath according to any of manual force and a sheath translation stage actuator.

10. The method of claim 9, wherein said device further comprises at least one sheath steering cable connected to a distal end of said sheath, said at least one sheath steering cable disposed inside said sheath, outside said multi-stage catheter device;

said at least one sheath steering cable enabled to convey sheath off-axis steering force on said distal end of said sheath, causing said distal end of said sheath and said multi-stage catheter device to move off-axis according to said sheath off-axis steering force;

further controlling said sheath off-axis steering force by using any of manual force or a sheath steering cable actuator to create and release tension on said at least one sheath steering cable.

11. A multi-stage catheter device for traversing internal body passages, said multi-stage catheter device comprising:

a distal stage hollow catheter and a different proximal stage hollow catheter;

said distal stage hollow catheter being a rotating distal stage hollow catheter with a distal stage axis that is configured to rotate about a proximal stage axis of said different proximal stage hollow catheter;

one end of said rotating distal stage hollow catheter affixed to an end of said different proximal stage hollow catheter by a transition point coupler;

said transition point coupler configured to traverse an internal body passage;

said transition point coupler comprising a transition housing that includes a hollow rotatable coupler, said hollow rotatable coupler configured as a rotary joint to enable said one end of said rotating distal stage hollow catheter to rotate about said end of said different proximal stage hollow catheter;

said device further comprising a hollow torque shaft mounted inside said proximal stage hollow catheter and attached to said hollow rotatable coupler, said hollow torque shaft configured to convey torque to said rotatable coupler and said rotating distal stage hollow catheter;

said device further comprising at least one proximal stage steering cable connected to said transition housing, said at least one proximal stage steering cable disposed inside said proximal stage hollow catheter, outside said hollow torque shaft, said at least one proximal stage steering cable enabled to convey proximal stage steering force on said transition housing, causing said transition housing and said distal stage hollow catheter to move according to said proximal stage steering force;

said hollow torque shaft, distal stage hollow catheter, hollow rotatable coupler and said transition housing further comprising a working channel configured to convey a plurality of conduits through said proximal stage hollow catheter and said distal stage hollow catheter to at least a distal tool plate mounted on a distal end of said distal stage hollow catheter;

wherein at least some of said conduits comprise at least one distal stage steering cable configured to convey distal stage steering force to said distal tool plate on said distal end of said distal stage hollow catheter;

said at least one distal stage steering cable enabled to cause said distal tool plate and said distal stage catheter to further move according to said distal stage steering force;

said device further comprising:

at least one distal stage tensioning actuator configured to flex and unflex said end of said distal stage hollow catheter by creating and releasing tension on at least one of said at least one distal stage steering cables;

said at least one distal stage tensioning actuator further configured by a distal stage rotary shift actuator to rotate said at least one distal stage steering cable in a 1:1 ratio with any rotation of at least said distal stage hollow catheter.

12. The device of claim 11, further comprising:
at least one proximal stage tensioning actuator configured to move said transition point coupler by creating and releasing tension on at least one of said at least one proximal stage steering cables;
at least one proximal stage tensioning actuator and a proximal stage rotary shaft actuator further configured to rotate said at least one proximal stage steering cable in a 1:1 ratio with any rotation of said proximal stage hollow catheter and said distal stage hollow catheter.

13. The device of claim 12, wherein any of said at least one distal stage tensioning actuator and said at least one proximal stage tensioning actuator further comprises at least one contacting mechanism, at least one electromagnetic actuator, and at least one processor-configured to control said at least one electromagnetic actuator;
wherein said device further comprises at least one motion or position sensor; and
wherein said at least one processor is further configured to use input from said at least one motion or position sensor to control said at least one electromagnetic actuator.

14. The device of claim 13, wherein said at least one contacting mechanism comprises at least one gear assembly; and wherein at least portions of said gear assembly are configured in a disposable or reposable cartridge that can be reversibly coupled and decoupled from said at least one electromagnetic actuator.

15. The device of claim 11, further comprising:
at least one payload dispensing actuator configured to move at least one payload along said working channel by advancing or retracting a payload dispensing conduit along said working channel.

16. The device of claim 11, wherein any of said at least one proximal stage steering cable and at least one distal stage steering cable are further disposed inside an isolation coil comprising a far-isolation-coil-end and a near-isolation-coil-end;
each said far-isolation-coil-end is attached proximate to a distal terminus of its corresponding steering cable in a manner that allows said corresponding steering cable to movably protrude past said far-isolation-coil-end while blocking axial movement of said far-isolation-coil-end;
each said near-isolation-coil-end is attached proximate to its respective flexing actuator in a manner that allows said corresponding steering cable to movably protrude past said near-isolation coil end while blocking axial movement of said near-isolation-coil-end;
said device further configured to rotate each said isolation coil in a 1:1 ratio with any rotation of its respective steering cable and any of its respective proximal stage and distal stage;
thus enabling variable tension applied by each said respective flexing actuator to be isolated to its respective steering cable while said cable is inside its respective isolation coil.

17. The device of claim 16, wherein each said isolation coil has an isolation coil compression;
at least said near-isolation-coil end is attached proximate to its respective flexing actuator in a manner that further enables said isolation coil compression to be adjusted;
said device further configured to adjust said isolation coil compression by any of a manual isolation coil compression adjuster and a compression actuator.

18. The device of claim 11, wherein said distal stage rotary shaft actustor is configured to apply torque to said hollow torque shaft.

19. The device of claim 11, wherein said device is further configured with at least proximal portions of said proximal stage hollow catheter disposed within at least one hollow sheath;
at least one of said at least one hollow sheath configured to enable at least portions of said multi-stage catheter device to protrude or retreat inside and outside of said at least one hollow sheath, depending on forces applied to said at least one hollow sheath and at least said proximal stage hollow catheter;
wherein said device is further configured with a sheath translation stage actuator configured to further control axial movement of said hollow sheath.

20. The device of claim 19, wherein said device further comprises at least one sheath steering cable connected to a distal end of said sheath, said at least one sheath steering cable disposed inside said sheath, outside said multi-stage catheter device;
said at least one sheath steering cable configured to convey sheath off-axis steering force on said distal end of said sheath, causing said distal end of said sheath and said multi-stage catheter device to move off-axis according to said sheath off-axis steering force;
said device further comprising any of a sheath off axis manual force application fixture and a sheath steering cable actuator configured to further control said sheath off-axis steering force by creating and releasing tension on said at least one sheath steering cable.

* * * * *